US009290576B2

(12) United States Patent
Attinger et al.

(10) Patent No.: US 9,290,576 B2
(45) Date of Patent: Mar. 22, 2016

(54) ANTIBODIES THAT BIND TO TL1A AND THEIR USES

(71) Applicant: GLENMARK PHARMACEUTICALS S.A., La Chaux-de-Fonds (CH)

(72) Inventors: Antoine Attinger, La Chaux-de-Fonds (CH); Jonathan Albert Back, La Chaux-de-Fonds (CH); Stanislas Blein, La Chaux-de-Fonds (CH); Rami Lissilaa, La Cheux-de-Fonds (CH); Darko Skegro, La Chaux-de-Fonds (CH)

(73) Assignee: GLENMARK PHARMACEUTICALS S.A., La Chaux de Fonds (CH)

( * ) Notice: Subject to any disclaimer, the term of this patent is extended or adjusted under 35 U.S.C. 154(b) by 0 days.

(21) Appl. No.: 14/146,566

(22) Filed: Jan. 2, 2014

(65) Prior Publication Data
US 2014/0308271 A1  Oct. 16, 2014

Related U.S. Application Data

(60) Provisional application No. 61/748,201, filed on Jan. 2, 2013.

(51) Int. Cl.
*A61K 39/395* (2006.01)
*C07K 16/28* (2006.01)
*A61K 47/48* (2006.01)
*A61K 39/00* (2006.01)

(52) U.S. Cl.
CPC ......... *C07K 16/2878* (2013.01); *A61K 39/3955* (2013.01); *A61K 47/48561* (2013.01); *C07K 16/2875* (2013.01); *A61K 2039/505* (2013.01); *C07K 2317/24* (2013.01); *C07K 2317/33* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,816,567 | A | 3/1989 | Cabilly et al. |
|---|---|---|---|
| 5,024,939 | A | 6/1991 | Gorman |
| 5,225,539 | A | 7/1993 | Winter |
| 5,530,101 | A | 6/1996 | Queen et al. |
| 5,585,089 | A | 12/1996 | Queen et al. |
| 5,624,821 | A | 4/1997 | Winter et al. |
| 5,648,260 | A | 7/1997 | Winter et al. |
| 5,677,425 | A | 10/1997 | Bodmer et al. |
| 5,693,762 | A | 12/1997 | Queen et al. |
| 5,869,046 | A | 2/1999 | Presta et al. |
| 6,121,022 | A | 9/2000 | Presta et al. |
| 6,165,745 | A | 12/2000 | Ward et al. |
| 6,180,370 | B1 | 1/2001 | Queen et al. |
| 6,194,551 | B1 | 2/2001 | Idusogie et al. |
| 6,277,375 | B1 | 8/2001 | Ward |

FOREIGN PATENT DOCUMENTS

| WO | WO 94/29351 | 12/1994 |
|---|---|---|
| WO | WO 00/42072 | 7/2000 |
| WO | WO 03/035835 A2 | 5/2003 |
| WO | WO 2010/095031 A2 | 8/2010 |

OTHER PUBLICATIONS

Abbott et al. Current approaches to fine mapping of antigen-antibody interactions. Immunology. Aug. 2014;142(4):526-35.*
Portolano et al. Lack of promiscuity in autoantigen-specific H and L chain combinations as revealed by human H and L chain "roulette". J Immunol. Feb. 1, 1993;150(3):880-7.*
Clackson et al. Making antibody fragments using phage display libraries. Nature. Aug. 15, 1991;352(6336):624-8.*
MacCallum et al. Antibody-antigen interactions: contact analysis and binding site topography. J Mol Biol. Oct. 11, 1996;262(5):732-45.*
De Pascalis et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.*
Casset et al. A peptide mimetic of an anti-CD4 monoclonal antibody by rational design. Biochem Biophys Res Commun. Jul. 18, 2003;307(1)1 98-205.*
Vajdos et al. Comprehensive functional maps of the antigen-binding site of an anti-ErbB2 antibody obtained with shotgun scanning mutagenesis. J Mol Biol. Jul. 5, 2002;320(2):415-28.*
Holm et al. Functional mapping and single chain construction of the anti-cytokeratin 8 monoclonal antibody TS1. Mol Immunol. Feb. 2007;44(6):1075-84. Epub Sep. 20, 2006.*
Wu et al. Humanization of a murine monoclonal antibody by simultaneous optimization of framework and CDR residues. J Mol Biol. Nov. 19, 1999;294(1)151-62.*
Padlan et al. Structure of an antibody-antigen complex: crystal structure of the HyHEL-10 Fab-lysozyme complex. Proc Natl Acad Sci U S A. Aug. 1989;86(15):5938-42.*
Lamminmaki et al. Crystal structure of a recombinant anti-estradiol Fab fragment in complex with 17beta-estradiol. J Biol Chem. Sep. 28, 2001;276(39):36687-94.*
Rudikoff et al. Single amino acid substitution altering antigen-binding specificity. Proc Natl Acad Sci U S A. Mar. 1982;79(6):1979-83.*

(Continued)

*Primary Examiner* — David Romeo
(74) *Attorney, Agent, or Firm* — Sterne, Kessler, Goldstein & Fox, P.L.L.C.; Timothy J. Shea, Jr.; Erin Heenan

(57) ABSTRACT

The present invention relates to antibodies or fragments thereof that bind to TL1A. More specifically, the present invention relates to an antibody or fragment thereof that binds to TL1A comprising a heavy chain CDR1 comprising the amino acid sequence of SEQ ID NO: 51, and/or a heavy chain CDR2 comprising the amino acid sequence of SEQ ID NO: 52, and/or a heavy chain CDR3 comprising the amino acid sequence of SEQ ID NO: 53; and/or comprising a light chain CDR1 comprising the amino acid sequence of SEQ ID NO: 54, and/or a light chain CDR2 comprising the amino acid sequence of SEQ ID NO: 55 and/or a light chain CDR3 comprising the amino acid sequence of SEQ ID NO: 56.

51 Claims, 10 Drawing Sheets

(56) References Cited

OTHER PUBLICATIONS

Arnold, K., et al., "The SWISS-MODEL workspace: a web-based environment for protein structure bomology modelling," *Bioinformatics 22* (2): 195-201, Oxford University Press, United Kingdom (2006).

Bamias, G., et al., "Expression, Localization, and Functional Activity of TL1A, a Novel Th1-Polarizing Cytokine in Inflammatory Bowel Disease," *J. Immunology 171*:4868-4874, The American Association of Immunologists, Inc., United States (2003).

Bamias, G., et al., "Role of TL1A and its receptor DR3 in two models of chronic murine ileitis," *PNAS 103* (22): 8441-8446, National Academy of Sciences, United States (2006).

Bossen, C, et al., "Mechanisms of Signal Transduction: Interactions of Tumor Necrosis Factor (TNF) and TNF Receptor Family Members in the Mouse and Human," *J. Biol. Chem. 281*: 13964-13971, The American Society for Biochemistry and Molecular Biology, Inc., United States (2006).

Boyce, J., et al., "No audible wheezing: nuggets and conundrums from mouse asthma models," *JEM 201* (12): 1869-1873, The Rockefeller University Press, United States (2005).

Edelman, G.M., et al., "The Covalent Structure of an Entire γG Immunoglobulin Molecule," *PNAS 63*: 78-85, National Academy of Sciences, United States (1969).

Fang, I., et al., "Essential role of TNF receptor superfamily 25 (TNFRSF25) in the development of allergic lung inflammation," *JEM 205* (5): 1037-1048, The Rockefeller University Press, United States (2008).

Garber, E., et al., "A broad range of Fab stabilities within a host of therapeutic IgGs," *Biochemical and Biophysical Research Communications 335*; : 751-757, Elsevier Inc., Netherlands (2007).

Hall, T.A., "BioEdit: a user-friendly biological sequence alignment editor and analysis program for Windows 95/98/NT," *Nucleic Acid Symposium Series 41*: 95-98, Oxford University Press, Unted Kingdom (1999).

Imai-Nishiya, H., et al., "Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC," *BMC Biotechnology 7* (84): 1-13, BioMed Central Ltd., United Kingdom (2007).

Johnson, G. and Wu., T.T., "Kabat Database and its applications: 30 years after the first variability plot," *Nucleic Acids Research 28* (1): 214-218, Oxford University Press, United Kingdom (2000).

Kang, Y-J., et al, "Involvement of TL1A and DR3 in induction of pro-inflammatory cytokines and matrix metalloproteinase-9 in atherogenesis," *Cytokine 29*: 229-235, Elsevier Press Ltd., Netherlands (2005).

Kearney, J.F., et al., "A New Mouse Myeloma Cell Line that Has Lost Immunoglobulin Expression but Permits the Construction of Antibody-Secreting Hybrid Cell Lines," *The Journal of Immunology 123* (4): 1548-1550, The Williams & Wilkins Co., United States (1979).

Kim, D., et al., "Improved Mammalian Expression Systems by Manipulating Transriptional Termination Regions," *Biotechnol. Prog. 19*: 1620-1622, American Chemical Society and American Institute of Chemical Engineers, United States (2003).

Kim, S. and Zhang, L., "Identification of naturally secreted soluble form of TL1A, a TNF-like cytokine," *Journal of Immunological Methods 298*: 1-8, Elsevier B.V., Netherlands (2005).

Koons, M.D., et al., "The Replicator of the Epstein-Barr Virus Latent Cycle Origin of DNA Replication, oriP, Is Composed of Multiple Functional Elements," *Journal of Virology 75* (220: 10582-10592, American Society for Microbiology, United States (2001).

Kumar, R.K., et al., "The 'Classical' Ovalbumin Challenge Model of Asthma in Mice," *Current Drug Targets 9*: 485-494, Bentham Science Publishers Ltd., United Arab Emirates (2008).

Longmore, G.D. and Schachter, H., "Product-Identification and Substrate-Specificity Studies of the GDP-L-Fucose: 2-Acetamido-2-Deoxy-β-D-Glucoside (Fuc→ASN-Linked GlcNAc) 6-α-L-Fucosyltransferase in a Golgi-Rich Fraction from a Porcine Liver," *Carbohydrate Research 100*: 365-392, Elsevier Scientific Publishing Company, Netherlands (1982).

Migone, T-S., et al., "TL1A Is a TNF-like Ligand for DR3 and TR6/DcR3 and Functions as a T Cell Costimulator," *Immunity 16* (3): 479-492, Elsevier Press Ltd., United Kingdom (2002).

Papadakis, K.A., et al., "Dominant Role for TL1A/DR3 Pathway in IL-12 plus IL-18-Induced IFN-γ Production by Peripheral Blood and Mucosal CCR9$^+$T Lymphocytes," *The Journal of Immunology 174*: 4958-4990, The American Association of Immunologists, Inc., United States (2005).

Perse, M. and Cerar, A., "Dextran Sodium Sulphate Colitis Mouse Model: Traps and Tricks," *Journal of Biomedicine and Biotechnology 2012*: 1-13, Hindawi Publishing Corporation, Egypt (Mar. 2012).

Prehn, J.L., et al., "Potential role for TL1A, the new TNF-family member and potent costimulator of IFN-γ, in mucosal inflammation," *Clinical Immunology 112*: 66-77, Elsevier Inc., United Kingdom (2004).

Prehn, J.L., et al., "The T Cell Costimulator TL1A Is Induced by Fc γR Signaling in Human Monocytes and Dendritic Cells," *J. Immunology 178*: 4033-4038, The American Association of Immunologists, Inc., United States (2007).

Retter, I., et al., "VBASE2, an integrative V gene database," *Nucleic Acids Research 33*: D671-D674, Oxford University Press, United Kingdom (2005).

Su, W.B., et al., "Differential regulation of interleukin-8 gene transcription by death receptor 3 (DR3) and type I TNF receptor (TNFRI)," *Experimental Cell Research 312*: 266-277, Elsevier Inc., Netherlands (2006).

Tan, K.B., et al., "Characterization of a novel TNF-like ligand and recently described TNF ligand and TNF receptor superfamily genes and their constitutive and inducible expression in hematopoietic and non-hematopoietic cells," *Gene 204*: 35-46, Elsevier Science B.V., Netherlands (1997).

Wirtz, S., et al., "Chemically induced mouse models of intestinal inflammation," *Nature Protocols 2* (3): 541-546, Nature Publishing Group, United Kingdom (2007).

Young, H.A. and Tovey, M.G., "TL1A: A mediator of gut inflanation," *PNAS 103* (22): 8303-8304, The National Academy of Sciences, United States (2006).

Zhai, Y., et al., "VEGI, a novel cytokine of the tumor necrosis factor family, is an angiogenesis inhibitor that suppresses the growth of colon carcinomas in vivo," *The FASEB Journal 13*: 181-189, The Federation of American Societies for Experimental Biology, United States (1999).

UniProt Accession No. O95150, "Tumor necrosis factor ligand superfamily member 15," Accessed on May 15, 2014 at httn://www.uniprot.org/uniprot/O95150.

UniProt Accession No. Q5UBV8, "Tumor necrosis factor ligand superfamily member 15," Accessed on May 15, 2014 at http://www.uniprot.org/uniprot/Q5UBV8.

UniProt Accession No. Q8K3Y7, "Tumor necrosis factor ligand superfamily member 15," Accessed on May 15, 2014 at http://www.uniprot.org/uniprot/Q8K3Y7.

* cited by examiner

ANTIBODIES THAT BIND TO TL1A AND THEIR USES

CROSS-REFERENCE TO RELATED APPLICATIONS

This application claims the benefit of U.S. Provisional Application No. 61/748,201, filed Jan. 2, 2013, which is incorporated by reference herein in its entirety.

FIELD OF THE INVENTION

The present invention relates to antibodies or fragments thereof that bind to TL1A. More specifically, the present invention relates to an antibody or fragment thereof that binds to TL1A comprising a heavy chain CDR1 comprising the amino acid sequence of SEQ ID NO: 51, and/or a heavy chain CDR2 comprising the amino acid sequence of SEQ ID NO: 52, and/or a heavy chain CDR3 comprising the amino acid sequence of SEQ ID NO: 53; and/or comprising a light chain CDR1 comprising the amino acid sequence of SEQ ID NO: 54, and/or a light chain CDR2 comprising the amino acid sequence of SEQ ID NO: 55 and/or a light chain CDR3 comprising the amino acid sequence of SEQ ID NO: 56.

BACKGROUND OF THE INVENTION

TNF-like ligand 1A (TL1A) is a member of the tumor necrosis factor (ligand) superfamily, member 15. TL1A is also known as TNFSF15 and VEGI and was identified in 1999 as an angiogenesis inhibitor that suppresses the growth of colon carcinomas in vio (Zhai Y et al., (1999) FASEB J, 13(1): 181-9). The protein is abundantly expressed in endothelial cells and activated cells of the hematopoietic lineage, including monocytes, macrophages, lymphocytes, lamina propria mononuclear cells, dendritic cells and plasma cells but is not expressed in either B or T cells (Tan K B et al. (1997) Gene, 204: 35-46; Prehn J L et al., (2007) J Immunol, 178: 4033-4038). It is also expressed in kidney, lung, prostate and thymus (Tan K B et al., (1997), supra). It is a ligand for TNFRSF25/DR3 and decoy receptor TR6/DcR3 and its expression is inducible by TNF and IL-1α. TNFRSF25/DR3 is a death domain-containing receptor that is upregulated during T cell activation. TL1A induces NF-kappaB activation and apoptosis in TNFRSF25/DR3-expressing cell lines, and in T cells, TL1A can act as a costimulator that increases IL-2 responsiveness and secretion of proinflammatory cytokines both in vitro and in vivo. The interaction of TL1A with DR3 can promote T cell expansion during an immune response (Migone T S et al. (2002) Immunity, 16(3): 479-92). The secreted decoy receptor (DcR3), a soluble protein of the tumor necrosis factor receptor (TNFR) superfamily, blocks the action of TL1A. (Kim S & Zhang L, (2005) J Immunol Methods, 298: 1-8). TL1A has been implicated as a potential therapeutic target in a number of diseases and disorders.

A major cause of lung inflammation in allergy and asthma is Th2 polarization of CD4 T cells with elevated IgE levels and production of IL-13 by NKT cells. TL1A plays a major role in allergic lung inflammation by co-stimulating IL-4 and IL-13 production in NKT cells. Blocking TL1A and DR3 interaction by TL1A antibody or dominant negative TL1A mutant abolishes lung inflammation (Fang L et al., (2008) J Exp Med, 205(5): 1037-48). DcR3, the decoy receptor for TL1A is expressed in several lung and colon carcinomas and in some normal tissues, therefore suggesting a role for TL1A in lung and colon carcinomas. In addition, TL1A has also been reported to be angiostatic and to induce metalloproteinase and IL-8 gene expression (Su W B et al., (2006) Exp Cell Res, 312: 266-277; Kang Y J et al., (2005) Cytokine, 29: 229-235). TL1A and DR3 may also be involved in the pathogenesis of atherosclerosis by increasing the production of proinflammatory cytokines and chemokines and decreasing plaque stability by inducing extracellular matrix-degrading enzymes (Kang Y J et al., (2005), supra). There is also evidence to suggest that TL1A/DR3 is involved in the etiology of rheumatoid arthritis (Bossen C et al., (2006) J Biol Chem, 281(20): 13964-13971).

An association between the expression of TL1A and inflammatory bowel disease has been identified by researchers (Prehn J L et al., (2004) Clin Immunol, 112: 66-77; Bamias G et al., (2003) J Immunol, 171: 4868-4874). Crohn's disease, which is a severe inflammatory bowel disorder, is thought to originate from predisposing genetic and environmental factors that cause an imbalance of effector (proinflammatory) and regulatory T cell responses, resulting in inflammation of the gastrointestinal mucosa and disease. The TL1A/DR3 pathway has been shown to play an important role in intestinal diseases, such as Crohn's disease (Papadakis K A et al., (2005) J. Immunol, 174: 4985-4990; Bamias G et al., (2003), supra) and therefore, blockade of the TL1A/DR3 pathway may offer therapeutic opportunities in this disease.

Death receptors and their ligands play a key role in the maintenance of tissue homeostasis and the physiological regulation of programmed cell death. Binding of a death ligand induces oligomerization of the receptor, recruitment of an adapter protein via a conserved cytoplasmic signalling element termed the death domain, activation of caspases and induction of apoptosis (Young H A et al., (2006) Proc Natl Acad Sci USA, 103(22): 8303-8304). Although death receptors such as Fas/Apo-1/CD95. TNF-R1, TRAIL-R1, TRAIL-R2, or DR3 were initially characterized as inducers of apoptosis, there is growing evidence that these receptors also have non-apoptotic functions, including regulation of the adaptive immune response. Bamias et al., reported that TL1A is expressed by lamina propia dendritic cells and that it functions by increasing the proliferation of memory cells, but not naïve CD4$^+$ T cells, and synergizes with IL-12 and/or low-dose stimulation of the T cell receptor to strongly enhance IFN-γ gene expression (Bamias G et al., (2006) Proc. Natl. Acad. Sci. USA, 103: 8441-8446). IFN-γ expression in the gut has been considered a marker of inflammation and many strategies for treating Crohn's disease rely on broad attempts to suppress the immune-activated state. However, such approaches (steroid treatment and immunosuppressive drugs) do not focus on the gut specifically and therefore have their own complications. Targeted therapies based on the use of antagonists of TNF-α were introduced with success in the 1990s and the results suggest that therapy directed specifically against TL1A or its receptor may provide an alternative targeted therapy for this debilitating disorder.

Current treatments for Crohn's disease include the anti-TNF-α monoclonal antibodies Infliximab (Remicade®; Centocor) and Adalimumab (Humira®; Abbott), as well as anti-inflammatories (e.g., sulfasalazine), cortisone or steroids (e.g., prednisone), immune system suppressors (e.g., 6-mercaptopurine) and antibiotics. However, Infliximab is the only treatment option having a high degree of specificity compared to the other available treatments (Young H A et al., (2006), supra). Although Infliximab is generally well tolerated it can cause a recurrence of tuberculosis infection, worsening of heart failure, demyelinating disease and an increased incidence of lymphoma.

Therefore there remains a need in the art for compositions that can be used in the treatment and diagnosis of diverse inflammatory and immune diseases and disorders.

SUMMARY OF THE INVENTION

The present disclosure relates generally to antibodies or fragments thereof that bind to TL1A, methods for their preparation and use, including methods for treating TL1A mediated disorders. The antibodies or fragments thereof of the present invention that bind to TL1A exhibit numerous desirable properties and may be useful for the treatment of various diseases that include but are not limited to inflammatory diseases and/or auto immune diseases, including inter alia inflammatory bowel diseases (e.g., ulcerative colitis and Crohn's disease), rheumatoid arthritis, multiple sclerosis (MS), atherosclerosis, transplant rejection, central nervous system injury, psoriasis, leukaemia or lymphoma (e.g., chronic lymphocytic leukaemia (CLL)), atherosclerosis, and lung and colon carcinomas. The antibodies or fragments thereof of the present invention that bind to TL1A exhibit numerous desirable properties and may be useful for the treatment of various diseases that include but are not limited to inflammatory diseases and/or auto immune diseases, including inter alia inflammatory bowel diseases (e.g., ulcerative colitis and Crohn's disease), rheumatoid arthritis, multiple sclerosis (MS), atherosclerosis, transplant rejection, central nervous system injury, psoriasis, leukaemia or lymphoma (e.g., chronic lymphocytic leukaemia (CLL)), atherosclerosis, and lung and colon carcinomas, chronic obstructive pulmonary disease COPD, optic neuritis, age related macular degeneration, systemic lupus erythematosus (SLE), sjogen's syndrome, scleroderma, systemic sclerosis, chronic Kidney disease, liver fibrosis, tuberculosis, idiopathic pulmonary fibrosis, tuberculosis induced lung fibrosis, retroperitoneal Fibrosis, pulmonary fibrosis, cystic fibrosis, endomyocardial fibrosis, atrial fibrosis, mediastinal fibrosis, myelofibrosis (bone marrow), retroperitoneal fibrosis, progressive massive fibrosis, pephrogenic systemic fibrosis, arthrofibrosis.

In one aspect, the present disclosure provides an antibody or fragment thereof that binds to TL1A comprising a heavy chain CDR1 comprising the amino acid sequence of SEQ ID NO: 51, and/or a heavy chain CDR2 comprising the amino acid sequence of SEQ ID NO: 52, and/or a heavy chain CDR3 comprising the amino acid sequence of SEQ ID NO: 53; and/or comprising a light chain CDR1 comprising the amino acid sequence of SEQ ID NO: 54, and/or a light chain CDR2 comprising the amino acid sequence of SEQ ID NO: 55 and/or a light chain CDR3 comprising the amino acid sequence of SEQ ID NO: 56.

In a further aspect the present invention provides an antibody or fragment thereof that binds to TL1A comprising a heavy chain variable region sequence comprising the amino acid sequence of SEQ ID NO: 1. In a further aspect the present invention provides an antibody or fragment thereof that binds to TL1A comprising a heavy chain variable framework region that is the product of or derived from a human gene selected from the group consisting of: IGHV1-2*02 (SEQ ID NO: 3), IGHV1-2*04 (SEQ ID NO: 4), IGHV1-2*05 (SEQ ID NO: 5), IGHV1-2*01 (SEQ ID NO: 6), and IGHV1-46*01 (SEQ ID NO: 7).

In a further aspect the present invention provides an antibody or fragment thereof comprising a heavy chain variable framework region that is the product of or derived from human gene IGHV1-2*02 (SEQ ID NO: 3) and wherein the heavy chain variable framework region comprises at least one amino acid modification from the corresponding framework region of the light chain variable region of the corresponding murine antibody.

In a further aspect the present invention provides an antibody or fragment thereof comprising a heavy chain sequence comprising the amino acid sequence of SEQ ID NO: 13 and wherein the heavy chain variable framework region comprises at least one amino acid modification from the corresponding heavy chain variable framework region of the corresponding murine antibody.

In a further aspect the present invention provides an antibody or fragment thereof that binds to TL1A comprising a light chain variable region sequence comprising the amino acid sequence of SEQ ID NO: 2. In a further aspect the present invention provides an antibody or fragment thereof that binds to TL1A comprising a light chain variable framework region that is the product of or derived from a human gene selected from the group consisting of: IGKV1-33*01 (SEQ ID NO: 8), IGKV1D-33*01 (SEQ ID NO: 9), IGKV1D-12*02 (SEQ ID NO: 10), IGKV1D-12*01 (SEQ ID NO: 11) and IGKV1-12*02 (SEQ ID NO: 12).

In a further aspect the present invention provides an antibody or fragment thereof comprising a light chain variable framework region that is the product of or derived from human gene IGKV1-33*01 (SEQ ID NO: 8) and wherein the light chain variable framework region comprises at least one amino acid modification from the corresponding framework region of the light chain variable region of the corresponding murine antibody.

In a further aspect the present invention provides an antibody or fragment thereof that binds to TL1A comprising a heavy chain sequence selected from the group consisting of SEQ ID NOS: 16, 21, 22, 23 and 24. In a further aspect the present invention provides an antibody or fragment thereof that binds to TL1A comprising a light chain sequence selected from the group consisting of SEQ ID NOS: 17 and 25.

In a further aspect the present invention provides an antibody or fragment thereof that binds to TL1A comprising:

(a) a heavy chain sequence comprising the amino acid sequence of SEQ ID NO: 22 or 24; and (b) a light chain sequence comprising the amino acid sequence of SEQ ID NO: 17.

In a further aspect the present invention provides an antibody or fragment thereof that binds to TL1A comprising a heavy chain variable region comprising the amino acid sequence selected from the group consisting of SEQ ID NOS: 13, 26, 27, 28 and 29. In a further aspect the present invention provides an antibody or fragment thereof that binds to TL1A comprising a light chain variable region comprising the amino acid sequence selected from the group consisting of SEQ ID NOS: 14 and 30.

In a further aspect the present invention provides an antibody or fragment thereof that binds to TL1A comprising:

(a) a heavy chain variable region comprising the amino acid sequence of SEQ ID NO: 27 or 29; and (b) a light chain variable region comprising the amino acid sequence of SEQ ID NO: 14.

In a further aspect the present invention provides an antibody or fragment thereof that binds to TL1A, wherein the antibody comprises a human IgG4 Fc region, wherein the antibody has no Fc-mediated cytotoxicity activity. In a further aspect the present invention provides an antibody or fragment thereof that binds to TL1A, wherein the antibody comprises a human IGHG1 Fc region, wherein the antibody is competent for cytotoxicity mechanisms such as antibody dependent cellular cytotoxicity (ADCC). In a preferred aspect, the antibody or fragment thereof that binds to TL1A has a non fucosylated IGHG1 Fc region and exhibits enhanced Fc-mediated cytotoxicity mechanisms such as ADCC.

In another aspect, the present invention provides a cross-reactive antibody of fragment thereof which binds to human TL1A and which also binds to murine, rat and cynomologous TL1A. By "cross-reactive antibody" is meant an antibody that binds to an antigen from one species, e.g. human, and which also binds to the corresponding antigen in a different species, e.g. rat.

In another aspect, the disclosure of the present invention also describes humanized antibodies or fragments thereof that bind with a similar affinity to TL1A as the corresponding chimeric antibody e.g. retain at least 85% of the TL1A binding affinity ($K_D$) of the corresponding chimeric antibody or have at least equivalent or higher TL1A binding affinity ($K_D$) when compared to the corresponding chimeric antibody. In a preferred aspect the humanised antibody or fragment thereof has approximately a three-fold higher TL1A binding affinity when compared to the corresponding chimeric antibody.

In a further aspect, the present invention also describes humanized antibodies or fragments thereof that bind to hTL1A and inhibits the interaction of hTL1A with both DR3 and DcR3.

The disclosure of the present invention also provides isolated nucleic acids encoding antibodies and fragments thereof that bind to TL1A, vectors and host cells comprising the nucleic acid or the vector. Compositions comprising the anti-TL1A antibody or fragment thereof and a pharmaceutically acceptable carrier and immunoconjugates comprising the antibody or fragment thereof linked to a therapeutic agent are also provided.

The present disclosure also provides methods for treating TL1A mediated disorders. In one aspect, in an in vitro model of TL1A-induced IFNγ secretion by primed CD4 T cells, an anti-TL1A antibody or fragment thereof efficiently suppressed the production of IFNγ induced by immune complex-stimulated monocytes. In another aspect, in an in vivo model of allergic asthma, an anti-TL1A antibody reduced the number of eosinophils in bronchoalveolar lavage fluid of asthmatic mice by approximately 4-fold. In a further aspect, in an in vivo model of acute colitis induced in mice with dextran sulphate sodium (DSS) and in rats by trinitrobenzenesulfonic acid (TNBS), an anti-TL1A antibody was effective in reducing the symptoms of disease.

The present disclosure also provides pharmaceutical compositions comprising an anti-TL1A antibody or fragments thereof and a carrier, such as a diluent or excipient.

The present disclosure also provides kits and articles of manufacture comprising the antibody or fragments thereof, a composition or an immunoconjugate for the treatment of a TL1A mediated disorder.

BRIEF DESCRIPTION OF THE FIGURES

FIG. 1A displays the absorbance at 450 nm of an ELISA against coated human TL1A-his and FIG. 1B displays the absorbance at 450 nm of an ELISA against an irrelevant protein-his.

FIG. 3A: PBMCs from healthy donors were stimulated with immune complexes then stained with fluorescent antibodies. The monocytes were gated based on large forward light scatter and high side scatter parameters. The histogram plot displays the PE fluorescence of monocytes gated population. The grey shaded histogram represents the isotype control and the blank histogram represents the staining with anti TL1A.

Standard deviation was calculated using a one way ANOVA * indicates p<0.05,  indicates p<0.01 and * indicates p<0.001.

Figure 8:
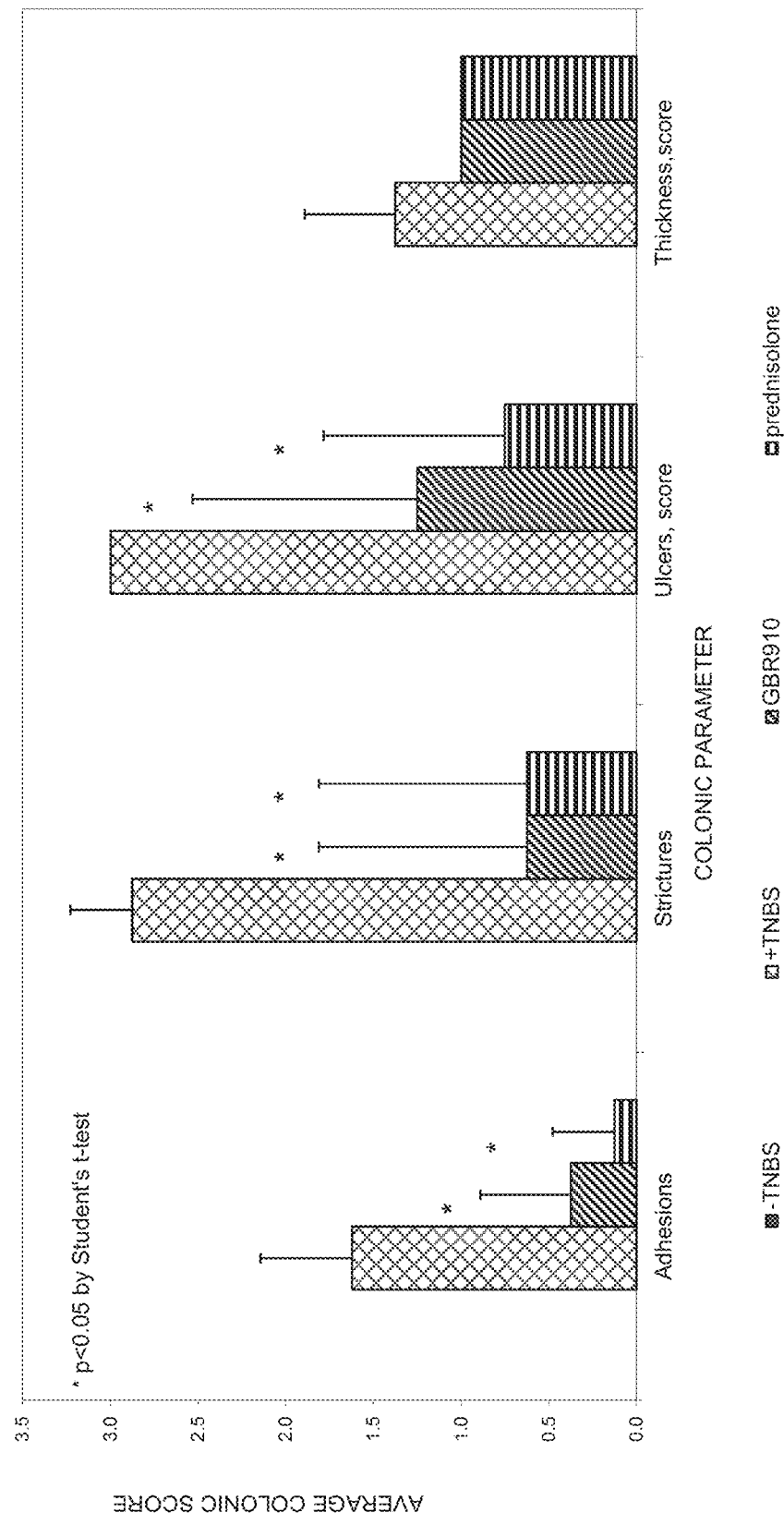

FIG. 8: Treatment by humanized 5G6 antibody ameliorates disease severity in a TNBS-induced model of acute colitis. Rats were treated i.p with a single dose of humanized 5G6 antibody (50 mg/kg) or an equal amount of isotype control, two hours after TNBS administration. Prednisolone was administered as a positive control. Disease severity was assessed using a colonic score for adhesions, strictures, ulcers and wall thickness and the average score is shown in the histograms. Standard deviation was calculated using a Student's t-test and * indicates p<0.05.

Figure 9:
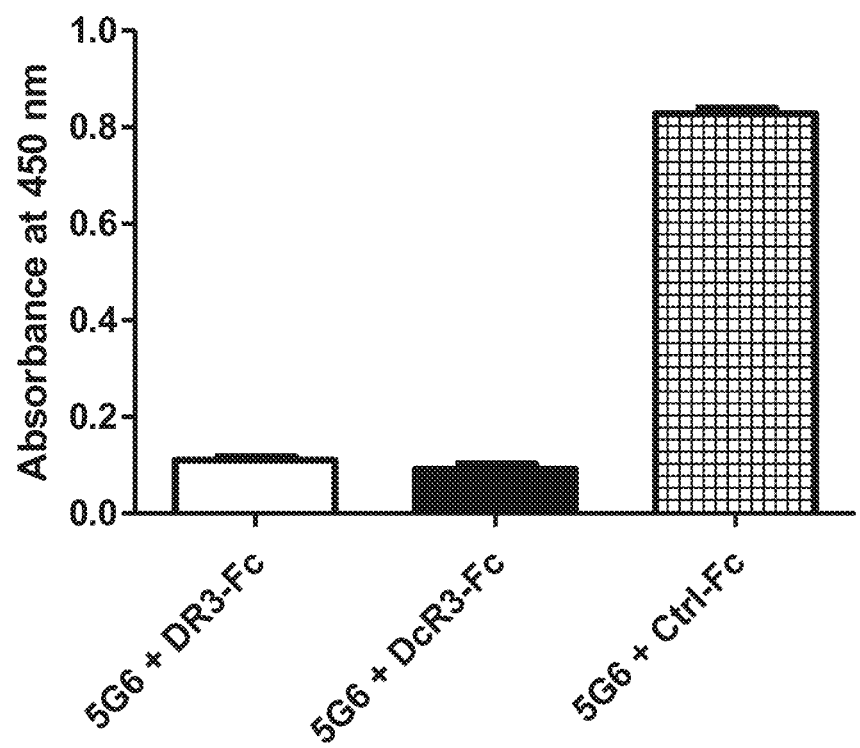

FIG. 9: Binding of 5G6 to hTL1A is blocked by both hDcR3-Fc and hDR3-Fc. Histidine-tagged human TL1A was coated at 2 μg/ml on an ELISA plate and incubated with 20 μg/ml 5G6 in the presence of 10 μg/ml Fc fusions of the ectodomains of either human DcR3 (white bar), DR3 (black bar) or an irrelevant receptor (Ctrl-Fc, hatched bar) followed by detection with peroxidase-conjugated anti-human IgG (Fab specific).

DETAILED DESCRIPTION OF THE INVENTION

The present disclosure relates to antibodies and fragments thereof that bind to TL1A.

The term "TL1A" as used herein includes variants, isoforms, and species homologs of TL1A. Accordingly, antibodies of this disclosure may bind to human TL1A and may cross-react with TL1A from species other than human, for example, mouse, rat or cynomologous monkey. In certain embodiments, the antibodies may be completely specific for one or more human TL1A proteins and may not exhibit species or other types of non-human cross-reactivity. The complete amino acid sequence of an exemplary human TL1A has Swiss-Prot accession number O95150 (TNFSF15_HUMAN; SEQ ID NO:38). TL1A is also known as TNFSF15; TNF-like protein 1A; VEGI; TNFγβ. Human TL1A is designated GeneID: 9966 by Entrez Gene, and HGNC: 11931 by HGNC. TL1A can be encoded by the gene designated TNFSF15/TL1A. The complete amino acid sequence of an exemplary murine TL1A has Swiss-Prot accession number Q5UBV8 (TNFSF15_MOUSE; SEQ ID NO: 39). Murine TL1A is designated GeneID: 326623 by Entrez Gene. The complete amino acid sequence of an exemplary rat TL1A has Swiss-Prot accession number Q8K3Y7 (TNFSF15_RAT; SEQ ID NO: 40). Rat TL1A is designated GeneID: 252878 by Entrez Gene. The complete amino acid sequence of an exemplary cyno TL1A (*macaca fascicularis*) has SEQ ID NO: 41.

The use of "TL1A" herein encompasses all known or as yet undiscovered alleles and polymorphic forms of TL1A, preferably human TL1A.

The term "antibody or fragment thereof that binds to TL1A" as used herein includes antibodies or a fragment thereof that binds to TL1A e.g. human TL1A in isolated form, with an affinity (K)) of 850 pM or less, preferably 700 nM or less, more preferably 300 nM or less, more preferably 260 nM or less, even more preferably 250 nM or less.

The term "antibody or fragment thereof that binds to TL1A" includes antibodies or antigenic binding fragments thereof.

The term "antibody" as referred to herein includes whole antibodies and any antigen binding fragments or single chains thereof. An "antibody" refers to a glycoprotein comprising at least two heavy (H) chains and two light (L) chains interconnected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR) with are hypervariable in sequence and/or involved in antigen recognition and/or usually form structurally defined loops, interspersed with regions that are more conserved, termed framework regions (FR or FW). Each VH and VL is composed of three CDRs and four FWs, arranged from amino-terminus to carboxy-terminus in the following order: FW1, CDR1, FW2, CDR2, FW3, CDR3, FW4. The amino acid sequences of FW1, FW2, FW3, and FW4 all together constitute the "non-CDR region" or "non-extended CDR region" of VH or VL as referred to herein.

The term "heavy chain variable framework region" as referred herein may comprise one or more (e.g., one, two, three and/or four) heavy chain framework region sequences (e.g., framework 1 (FW1), framework 2 (FW2), framework 3 (FW3) and/or framework 4 (FW4)). Preferably the heavy chain variable region framework comprises FW1, FW2 and/or FW3, more preferably FW1, FW2 and FW3. The term "light chain variable framework region" as referred herein may comprise one or more (e.g., one, two, three and/or four) light chain framework region sequences (e.g., framework 1 (FW1), framework 2 (FW2), framework 3 (FW3) and/or framework 4 (FW4)). Preferably the light chain variable region framework comprises FW1. FW2 and/or FW3, more preferably FW1, FW2 and FW3.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies are grouped into classes, also referred to as isotypes, as determined genetically by the constant region. Human constant light chains are classified as kappa (CK) and lambda (Cλ) light chains. Heavy chains are classified as mu (μ), delta (δ), gamma (γ), alpha (α), or epsilon (ε), and define the antibody's isotype as IgM, IgD, IgG, IgA, and IgE, respectively. Thus, "isotype" as used herein is meant any of the classes and/or subclasses of immunoglobulins defined by the chemical and antigenic characteristics of their constant regions. The known human immunoglobulin isotypes are IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), and IgE (IGHE). The so-called human immunoglobulin pseudo-gamma IGHGP gene represents an additional human immunoglobulin heavy constant region gene which has been sequenced but does not encode a protein due to an altered switch region (Bensmana M et al., (1988) Nucleic Acids Res. 16(7): 3108). In spite of having an altered switch region, the human immunoglobulin pseudo-gamma IGHGP gene has open reading frames for all heavy constant domains (CH1-CH3) and hinge. All open reading frames for its heavy constant domains encode protein domains which align well with all human immunoglobulin constant domains with the predicted structural features. This additional pseudo-gamma isotype is referred herein as IgGP or IGHGP. Other pseudo immunoglobulin genes have been reported such as the human immunoglobulin heavy constant domain epsilon P1 and P2 pseudo-genes (IGHEP1 and IGHEP2). The IgG class is the most commonly used for therapeutic purposes. In humans this class comprises subclasses IgG1, IgG2, IgG3 and IgG4. In mice this class comprises subclasses IgG1, IgG2a, IgG2b. IgG2c and IgG3.

The term "murine antibody" as used herein includes antibodies in which the variable region sequences and the constant region sequences are derived from a mouse.

The term "chimeric antibody" as used herein includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" or "humanized anti-TL1A antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "neutralising antibody" includes an antibody that is capable of inhibiting and/or neutralising the biological activity of TL1A, for example by blocking binding or substantially reducing binding of TL1A to its receptor TNFRSF25/DR3 or the decoy receptor TNFRSF21/DR6 and thus inhibiting or reducing the signalisation pathway triggered by TL1A and/or inhibiting or reducing a TL1A-mediated cell response like e.g. lymphocyte proliferation, cytokine expression, or lymphocyte survival.

The terms "antagonistic antibody" or "antagonist antibody" are used herein equivalently and include an antibody that is capable of inhibiting and/or neutralising the biological signalling activity of TL1A, as described for a neutralising antibody supra.

The terms "agonistic antibody" or "agonist antibody" are used herein equivalently and include an antibody that is capable of activating and/or enhancing the biological signalling activity of TL1A, for example by increasing binding of TL1A to its receptor TNFRSF25/DR3 or the decoy receptor TNFRSF21/DR6 and thus activating or enhancing the signalisation pathway triggered by TL1A and/or activating or enhancing a TL1A-mediated cell response like e.g. lymphocyte proliferation, cytokine expression, or lymphocyte survival."

The term "Fab" or "Fab region" as used herein includes the polypeptides that comprise the VH, CH1, VL, and CL immunoglobulin domains. Fab may refer to this region in isolation, or this region in the context of a full length antibody or antibody fragment.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains C gamma 2 and C gamma 3 (Cγ2 and Cγ3) and the hinge between C gamma 1 (Cγ1) and C gamma 2 (Cγ2). Although the boundaries of the Fc region may vary, the human IgG heavy chain Fc region is usually defined to comprise residues C226 or P230 to its carboxyl-terminus, wherein the numbering is according to the EU numbering system. For human IgG1 the Fc region is herein defined to comprise residue P232 to its carboxyl-terminus, wherein the numbering is according to the EU numbering system (Edelman G M et al. (1969) Proc Natl Acad Sci USA, 63(1): 78-85). Fc may refer to this region in isolation or this region in the context of an Fc polypeptide, for example an antibody.

The term "hinge" or "hinge region" or "antibody hinge region" herein includes the flexible polypeptide comprising the amino acids between the first and second constant domains of an antibody. The "hinge region" as referred to herein is a sequence region of 6-62 amino acids in length, only present in IgA, IgD and IgG, which encompasses the cysteine residues that bridge the two heavy chains. Structurally, the IgG CH1 domain ends at EU position 220, and the IgG CH2 domain begins at residue EU position 237. Thus for IgG the antibody hinge is herein defined to include positions 221 (D221 in IgG1) to 231 (A231 in IgG1), wherein the numbering is according to the EU numbering system (Edelman G M et al., supra).

The term "parent antibody" or "parent immunoglobulin" as used herein includes an unmodified antibody that is subsequently modified to generate a variant. Said parent antibody may be a naturally occurring antibody, or a variant or engineered version of a naturally occurring antibody. Parent antibody may refer to the antibody itself, compositions that comprise the parent antibody, or the amino acid sequence that encodes it. By "parent anti-TL1A antibody" as used herein is meant an antibody or immunoglobulin that binds TL1A and is modified to generate a variant. By "corresponding murine antibody" as used herein is meant a murine antibody or immunoglobulin that binds to TL1A and that can be modified to generate a variant, specifically the murine antibody 5G6 as disclosed herein. By "corresponding chimeric antibody" as used herein is meant a chimeric antibody or immunoglobulin that binds to TL1A and that can be modified to generate a variant.

The term "variant antibody" or "antibody variant" as used herein includes an antibody sequence that differs from that of a parent antibody sequence by virtue of at least one amino acid modification compared to the parent. The variant antibody sequence herein will preferably possess at least about 80%, most preferably at least about 90%, more preferably at least about 95% amino acid sequence identity with a parent antibody sequence. Antibody variant may refer to the antibody itself, compositions comprising the antibody variant, or the amino acid sequence that encodes it.

The term "identity" or "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 80%, and more preferably at least about 90%, 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 80% sequence identity, even more preferably at least 90%, 95%, 98% or 99% sequence identity. Preferably, residue positions which are not identical differ by conservative amino acid substitutions.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in this case a heavy chain variable framework region variant, in which the arginine at position 94 is replaced with a lysine. For the preceding example, 94K indicates the substitution of position 94 with a lysine. For the purposes herein, multiple substitutions are typically separated by a slash. For example. R94K/L78V refers to a double variant comprising the substitutions R94K and L78V. By "amino acid insertion" or "insertion" as used herein is meant the addition of an amino acid at a particular position in a parent polypeptide sequence. For example, insert –94 designates an insertion at position 94. By "amino acid deletion" or "deletion" as used herein is meant the removal of an amino acid at a particular position in a parent polypeptide sequence. For example, R94– designates the deletion of arginine at position 94.

As used herein, the term "conservative modifications" or "conservative sequence modifications" is intended to refer to amino acid modifications that do not significantly affect or alter the binding characteristics of the antibody containing the amino acid sequence. Such conservative modifications include amino acid substitutions, insertions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions or within the framework regions of an antibody of the invention can be replaced with other amino acid residues from the same side chain family and the altered antibody (variant antibody) can be tested for retained function.

The term "epitope" refers to a region of an antigen that is bound by an antibody. An epitope may be defined as structural or functional. Functional epitopes are generally a subset of structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

For all human immunoglobulin heavy chain constant domains numbering is according to the "EU numbering system" (Edelman G M et al. (1969) Proc Natl Acad Sci USA, 63(1): 78-85).

For the human kappa immunoglobulin light chain constant domain (IGKC), numbering is according to the "EU numbering system" (Edelman G M et al., supra).

For the human lambda immunoglobulin light chain constant domains (IGLC1, IGLC2, IGLC3, IGLC6, and IGLC7), numbering is according to the "Kabat numbering system" (Kabat E A et al., (1991) Sequences of proteins of immunological interest. 5th Edition—US Department of Health and Human Services, NIH publication no 91-3242) as described by Dariavach P et al., (1987) Proc Natl Acad Sci USA, 84(24): 9074-8 and Frangione B et al., (1985) Proc Natl Acad Sci USA, 82(10): 3415-9.

The term "variable domain" refers to the domains that mediates antigen-binding and defines specificity of a particular antibody for a particular antigen. In naturally occurring antibodies, the antigen-binding site consists of two variable domains that define specificity: one located in the heavy chain (VH) and the other located in the light chain (VL). In some cases, specificity may exclusively reside in only one of the two domains as in single-domain antibodies from heavy-chain antibodies found in camelids. The V regions are usually about 110 amino acids long, and consist of relatively invariant stretches of amino acid sequence called framework regions (FRs) of 15-30 amino acids separated by shorter regions of extreme variability called "hypervariable regions" that are 9-12 amino acids long. The variable domains of native heavy and light chains comprise four FRs, largely adopting a beat-sheet configuration, connected by three hypervariable regions, which form loops. The hypervariable regions in each chain are held together in close proximity by FRs, and with the hypervariable regions from the other chain, contribute to the formation of the antigen binding site of antibodies (see Kabat EA et al., supra). The term "hypervariable region" as used herein refers to the amino acid residues of an antibody which are responsible for antigen binding. The hypervariable region generally comprises amino acid residues from a "complementary determining region" or "CDR", the latter being of highest sequence variability and/or involved in antigen recognition. For all variable domains numbering is according to Kabat (Kabat E A et al., supra).

A number of CDR definitions are in use and are encompassed herein. The Kabat definition is based on sequence variability and is the most commonly used (Kabat EA et al., supra). Chothia refers instead to the location of the structural loops (Chothia C & Lesk A M (1987) J. Mol. Biol. 196: 901-917). The AbM definition is a compromise between the Kabat and the Chothia definitions and is used by Oxford Molecular's AbM antibody modelling software (Martin ACR et al., (1989) Proc. Natl Acad. Sci. USA, 86: 9268-72; Martin A C R et al., (1991) Methods Enzymol. 203: 121-153; Pedersen JT et al., (1992) Immunomethods, 1: 126-136; Rees A R et al., (1996) In Sternberg M.J.E. (ed.), Protein Structure Prediction. Oxford University Press, Oxford, 141-172). The contact definition has been recently introduced (MacCallum RM et al., (1996) J. Mol. Biol. 262: 732-745) and is based on an analysis of the available complex structures available in the Protein Databank. The definition of the CDR by IMGT®, the international ImMunoGeneTics information system® is based on the IMGT numbering for all immunoglobulin and T cell receptor V-REGIONs of all species (IMGT®, the international ImMunoGeneTics information system®; Lefranc M P et al., (1991) Nucleic Acids Res. 27(1): 209-12; Ruiz M et al., (2000) Nucleic Acids Res. 28(1): 219-21; Lefranc M P (2001) Nucleic Acids Res. 29(1): 207-9; Lefranc M P (2003) Nucleic Acids Res. 31(1): 307-10; Lefranc M P et al., (2005) Dev. Comp. Immunol. 29(3): 185-203; Kaas Q et al., (2007) Briefings in Functional Genomics & Proteomics, 6(4): 253-64).

All Complementarity Determining Regions (CDRs) discussed in the present invention, are defined preferably according to IMGT®. The variable domain residues for each of these CDRs are as follows (numbering according to Kabat E A, et al., supra): LCDR1: 27-32, LCDR2: 50-52, LCDR3: 89-97, HCDR1: 26-35, HCDR2: 51-57 and HCDR3: 93-102. The "non-CDR region" of the VL region as used herein comprise the amino acid sequences: 1-26 (FR1), 33-49 (FR2), 53-88 (FR3), and 98-approximately 107 (FR4). The "non-CDR region" of the VH region as used herein comprise the amino acid sequences: 1-25 (FR1), 36-50 (FR2), 58-92 (FR3), and 103-approximately 113 (FR4).

The CDRs of the present invention may comprise "extended CDRs" which are based on the aforementioned definitions and have variable domain residues as follows: LCDR1: 24-36, LCDR2: 46-56, LCDR3:89-97, HCDR1: 26-36, HCDR2:47-65, HCDR3: 93-102. These extended CDRs are numbered as well according to Kabat et al., supra. The "non-extended CDR region" of the VL region as used herein comprise the amino acid sequences: 1-23 (FR1), 37-45 (FR2), 57-88 (FR3), and 98-approximately 107 (FR4). The "non-extended CDR region" of the VH region as used herein comprise the amino acid sequences: 1-25 (FR1), 37-46 (FR2), 66-92 (FR3), and 103-approximately 113 (FR4).

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward E S et al., (1989) Nature, 341: 544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird R E et al., (1988) Science 242: 423-426; Huston J S et al., (1988) Proc. Natl. Acad. Sci. USA, 85: 5879-83), (vii) bispecific single chain Fv dimers (PCT/US92/09965), (viii) "diabodies" or "triabodies", multivalent or multispecific fragments constructed by gene fusion (Tomlinson I & Hollinger P (2000) Methods Enzymol. 326: 461-79; WO94/13804; Holliger P et al., (1993) Proc. Natl. Acad. Sci. USA, 90: 6444-48) and (ix) scFv genetically fused to the same or a different antibody (Coloma M J & Morrison S L (1997) Nature Biotechnology, 15(2): 159-163).

The term "effector function" as used herein includes a biochemical event that results from the interaction of an antibody Fc region with an Fc receptor or ligand. Effector functions include FcγR-mediated effector functions such as ADCC (antibody dependent cell-mediated cytotoxicity) and ADCP (antibody dependent cell-mediated phagocytosis), and complement-mediated effector functions such as CDC (complement dependent cytotoxicity). An effector function of an antibody may be altered by altering, i.e. enhancing or reducing, preferably enhancing, the affinity of the antibody for an effector molecule such as an Fc receptor or a complement component. Effector function may be determined using one or more cell based or in vivo assays. Such assays often involve monitoring the response of cells to the antibody, for example cell survival, cell death, change in cellular morphology or transcriptional activation such as cellular expression of a natural gene or reporter gene. For example, such assays may measure the ability of an antibody to elicit ADCC, ADCP, or CDC. For some assays additional cells or components, that is in addition to the target cells, may need to be added, for example serum complement or effector cells such as peripheral blood monocytes (PBMCs). NK cells, macrophages, and the like. Enhanced effector function can be determined by comparing the effector function of an altered antibody with a control antibody and detecting, for example, an increase in ADCC, ADCP or CDC measured by one of more of the aforementioned assays.

Binding affinity will generally be varied by modifying the effector molecule binding site and in this case it is appropriate to locate the site of interest and modify at least part of the site in a suitable way. It is also envisaged that an alteration in the binding site on the antibody for the effector molecule need not alter significantly the overall binding affinity but may alter the geometry of the interaction rendering the effector mechanism ineffective as in non-productive binding. It is further envisaged that an effector function may also be altered by modifying a site not directly involved in effector molecule binding, but otherwise involved in performance of the effector function. By altering an effector function of an antibody it may be possible to control various aspects of the immune response, e.g. enhancing or suppressing various reactions of the immune system, with possible beneficial effects in diagnosis and therapy.

As used herein, the term "TL1A-mediated disorder" includes conditions such as inflammatory diseases and/or auto immune diseases, including inter alia inflammatory bowel diseases (e.g., ulcerative colitis and Crohn's disease), rheumatoid arthritis, multiple sclerosis (MS), atherosclerosis, transplant rejection, central nervous system injury, psoriasis, leukemia or lymphoma (e.g., chronic lymphocytic leukemia (CLL)), atherosclerosis, and lung and colon carcinomas, chronic obstructive pulmonary disease COPD, optic neuritis, age related macular degeneration, systemic lupus erythematosus (SLE), sjogen's syndrome, scleroderma, systemic sclerosis, chronic Kidney disease, liver fibrosis, tuberculosis, idiopathic pulmonary fibrosis, tuberculosis induced lung fibrosis, retroperitoneal Fibrosis, pulmonary fibrosis, cystic fibrosis, endomyocardial fibrosis, atrial fibrosis, mediastinal fibrosis, myelofibrosis (bone marrow), retroperitoneal fibrosis, progressive massive fibrosis, pephrogenic systemic fibrosis, arthrofibrosis.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc. Preferably the subject is human.

Anti-TL1A Antibodies

In a first aspect the present invention provides an antibody or fragment thereof that binds to TL1A comprising a heavy chain CDR1 comprising the amino acid sequence of SEQ ID NO: 51, and/or a heavy chain CDR2 comprising the amino acid sequence of SEQ ID NO: 52, and/or a heavy chain CDR3 comprising the amino acid sequence of SEQ ID NO: 53; and/or comprising a light chain CDR1 comprising the amino acid sequence of SEQ ID NO: 54, and/or a light chain CDR2 comprising the amino acid sequence of SEQ ID NO: 55 and/or a light chain CDR3 comprising the amino acid sequence of SEQ ID NO: 56.

In some embodiments the antibody or fragment thereof that binds to TL1A comprises an extended heavy chain CDR1 comprising the amino acid sequence of SEQ ID NO: 57, and/or an extended heavy chain CDR2 comprising the amino acid sequence of SEQ ID NO: 58, and/or an extended heavy chain CDR3 comprising the amino acid sequence of SEQ ID NO: 59; and/or comprises an extended light chain CDR1 comprising the amino acid sequence of SEQ ID NO: 60, and/or an extended light chain CDR2 comprising the amino acid sequence of SEQ ID NO: 61 and/or an extended light chain CDR3 comprising the amino acid sequence of SEQ ID NO: 62.

Preferably the antibody or fragment thereof that binds to TL1A and comprises a heavy chain CDR1 comprising the amino acid sequence of SEQ ID NO: 51, a heavy chain CDR2 comprising the amino acid sequence of SEQ ID NO: 52, and a heavy chain CDR3 comprising the amino acid sequence of SEQ ID NO: 53 and/or a light chain CDR1 comprising the amino acid sequence of SEQ ID NO: 54, a light chain CDR2 comprising the amino acid sequence of SEQ ID NO: 55 and a light chain CDR3 comprising the amino acid sequence of SEQ ID NO: 56. More preferably the antibody or fragment thereof that binds to TL1A comprises a heavy chain CDR1 comprising the amino acid sequence of SEQ ID NO: 51, a heavy chain CDR2 comprising the amino acid sequence of SEQ ID NO: 52, and a heavy chain CDR3 comprising the amino acid sequence of SEQ ID NO: 53 and a light chain CDR1 comprising the amino acid sequence of SEQ ID NO: 54, a light chain CDR2 comprising the amino acid sequence of SEQ ID NO: 55 and a light chain CDR3 comprising the amino acid sequence of SEQ ID NO: 56. Preferably, the antibody or fragment thereof binds to human TL1A and is cross reactive with murine, rat and cyno TL1A.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka A et al., (2000) Br. J. Cancer, 83(2): 252-260 (describing the production of a humanized anti-CD30 antibody using only the heavy chain variable domain CDR3 of murine anti-CD30 antibody Ki-4); Beiboer S H et al., (2000) J. Mol. Biol. 296: 833-849 (describing recombinant epithelial glycoprotein-2 (EGP-2) antibodies using only the heavy chain CDR3 sequence of the parental murine MOC-31 anti-EGP-2 antibody); Rader C et al., (1998) Proc. Natl. Acad. Sci. USA, 95: 8910-8915 (describing a panel of humanized anti-integrin αvβ3 antibodies using a heavy and light chain variable CDR3 domain of a murine anti-integrin αvβ3 antibody LM609 wherein each member antibody comprises a distinct sequence outside the CDR3 domain and capable of binding the same epitope as the parental murine antibody with affinities as high or higher than the parental murine antibody); Barbas C et al., (1994) J. Am. Chem. Soc. 116: 2161-62 (disclosing that the CDR3 domain provides the most significant contribution to antigen binding).

Accordingly, the present invention provides antibodies and fragments thereof that bind to TL1A comprising one or more heavy and/or light chain CDR3 domains, in particular comprising heavy chain CDR3 comprising the amino acid sequence of SEQ ID NO: 53 and/or light chain CDR3 comprising the amino acid sequence of SEQ ID NO: 56, wherein the antibody is capable of binding to TL1A. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human e.g. murine antibody.

In further aspect the antibody or fragment thereof comprises a heavy chain variable region sequence comprising the amino acid sequence of SEQ ID NO: 1. In further aspect the antibody or fragment thereof comprises a non-CDR region of a heavy chain variable region sequence which is at least 80% identical to the non-CDR region of the heavy chain variable region sequence of SEQ ID NO: 1.

In a further aspect the present invention provides an antibody or fragment thereof that binds to TL1A comprising a heavy chain variable region sequence comprising the amino acid sequence selected from SEQ ID NO: 26, SEQ ID NO: 27, SEQ ID NO: 28 and SEQ ID NO: 29.

In a further aspect the present invention provides an antibody or fragment thereof that binds to TL1A comprising a heavy chain variable region sequence comprising the amino acid sequence of SEQ ID NO: 29. In another aspect the present invention provides an antibody or fragment thereof that binds to TL1A comprising a light chain variable region sequence comprising the amino acid sequence of SEQ ID NO: 14. In some embodiments the antibody or fragment thereof that binds to TL1A comprises a heavy chain variable region sequence comprising the amino acid sequence of SEQ ID NO: 29 and a light chain variable region sequence comprising the amino acid sequence of SEQ ID NO: 14. Preferably, the antibody or fragment thereof binds to human TL1A and is cross reactive with murine, rat and cyno TL1A.

In another aspect the present invention provides variants of an antibody or fragment thereof that binds to TL1A. Thus the present invention provides antibodies or fragments thereof that have an amino acid sequence of the non-CDR regions of the heavy and/or light chain variable region sequence which is at least 80% identical (having at least 80% amino acid sequence identity) to the amino acid sequence of the non-CDR regions of the heavy and/or light chain variable region sequence of the parent antibody of either the heavy or the light chain e.g. of either the heavy and light variable region sequences as in SEQ ID NO: 13. SEQ ID NO: 26. SEQ ID NO: 27, SEQ ID NO: 28, SEQ ID NO: 29 or SEQ ID NO: 14, respectively. As well antibodies or fragments thereof that have an amino acid sequence of the non-extended CDR regions of the heavy and/or light chain variable region sequence which is at least 80% identical to the amino acid sequence of the non-extended CDR regions of the heavy and/or light chain variable region sequence of the parent antibody of either the heavy or the light chain are provided by the present invention. Preferably the amino acid sequence identity of the non-CDR regions or of the non-extended CDR regions of the heavy and/or light chain variable region sequence is at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to an amino acid sequence is defined herein as the percentage of amino acid residues in the candidate sequence that are identical with the antibody or fragment thereof that binds to TL1A, after aligning the sequences and introducing gaps, if necessary, to achieve the maximum percent sequence identity. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM250 (a standard scoring matrix; see Dayhoff MO et al., (1978) in Atlas of Protein Sequence and Structure, vol 5, supp. 3) can be used in conjunction with the computer program. For example, the percent identity can be calculated as: the total number of identical matches multiplied by 100 and then divided by the sum of the length of the longer sequence within the matched span and the number of gaps introduced into the longer sequences in order to align the two sequences.

In some embodiments the present disclosure thus provides an antibody or fragment thereof that binds to TL1A, wherein the antibody or fragment thereof comprises a heavy chain variable framework region sequence which is at least 65% identical to the framework region sequence of SEQ ID NOS: 3, 4, 5, 6 or 7 and/or a light chain variable framework region sequence which is at least 75% identical to the framework region sequence of SEQ ID NOS: 8, 9, 10, 11 and 12. In some embodiments the present disclosure provides an antibody or fragment thereof that binds to TL1A, wherein the antibody or fragment thereof comprises a heavy chain variable framework region sequence which is at least 69% identical to the framework region sequence of SEQ ID NO: 3 and/or a light chain variable framework region sequence which is at least 80% identical to the framework region sequence of SEQ ID NO: 8.

In another aspect the present invention provides an antibody or fragment thereof that binds to TL1A comprising the heavy and or light chain CDRs as described supra and further comprising a heavy chain variable framework region that is the product of or derived from a human gene selected from the group consisting of IGHV1-2*02 (SEQ ID NO: 3), IGHV1-2*04 (SEQ ID NO: 4), IGHV1-2*05 (SEQ ID NO: 5), IGHV1-2*01 (SEQ ID NO: 6), and IGHV1-46*01 (SEQ ID NO: 7), preferably a heavy chain variable framework region that is the product of or derived from human gene IGHV1-2*01 (SEQ ID NO: 3). The heavy chain variable framework region may comprise one or more (e.g., one, two, three and/or four) heavy chain framework region sequences (e.g., framework 1 (FW1), framework 2 (FW2), framework 3 (FW3) and/or framework 4 (FW4)) present in the product of or derived from those human genes. Preferably the heavy chain variable region framework comprises FW1, FW2 and/or FW3, more preferably FW1, FW2 and FW3 present in the product of or derived from a human gene selected from the group consisting of IGHV1-2*02 (SEQ ID NO: 3), IGHV1-2*04 (SEQ ID NO: 4), IGHV1-2*05 (SEQ ID NO: 5), IGHV1-2*01 (SEQ ID NO: 6), and IGHV1-46*01 (SEQ ID NO: 7). Heavy chain framework region sequences as used herein include FW1 (position 1 to position 25). FW2 (position 36 to position 49), FW3 (position 66 to position 94) and FW 4 (position 103 to position 113), wherein the amino acid position is indicated utilizing the numbering system set forth in Kabat.

In some embodiments the present disclosure provides an antibody or fragment thereof, wherein the antibody or fragment thereof comprises a heavy chain variable framework region that is the product of or derived from human gene IGHV1-2*01 (SEQ ID NO: 3) and wherein the heavy chain variable framework region comprises at least one amino acid modification from the corresponding heavy chain variable framework region of the corresponding murine antibody.

In some embodiments the present disclosure provides an antibody or fragment thereof comprising a heavy chain sequence comprising the amino acid sequence of SEQ ID NO: 16 and wherein the heavy chain variable framework region comprises at least one amino acid modification from the corresponding heavy chain variable framework region of the corresponding murine antibody.

Preferably the amino acid modification comprises an amino acid substitution at amino acid position selected from the group consisting of 37, 48, 50, 67, 69, 71 and 75, more preferably at amino acid positions selected from the group consisting of 37, 48, 50, 67 and 71, most preferred at amino acid position 37, wherein the amino acid position of each group member is indicated according to the Kabat numbering. Specifically the amino acid modification comprises an amino acid substitution selected from the group consisting of 37A, 48I, 50E, 67A, 69L, 71V and 75S, preferably an amino acid substitution selected from the group consisting of V37A, M48I, W50E, V67A, M69L, R71V and I75S, whereas V37A is the most preferred amino acid substitution wherein the amino acid position of each group member is indicated according to the Kabat numbering.

In another aspect the present invention provides an antibody or fragment thereof that binds to TL1A comprising a light chain variable framework region that is the product of or derived from a human gene selected from the group consisting of IGKV1-33*01 (SEQ ID NO: 8), IGKV1D-33*01 (SEQ ID NO: 9), IGKV1D-12*02 (SEQ ID NO: 10), IGKV1D-12*01 (SEQ ID NO: 11), and IGKV1-12*02 (SEQ ID NO: 12), preferably a light chain variable framework region that is the product of or derived from human gene IGKV1-33*01 (SEQ ID NO: 8). The light chain variable region framework region may comprise one or more (e.g., one, two, three and/or four) light chain framework region sequences (e.g., framework 1 (FW1), framework 2 (FW2), framework 3 (FW3) and/or framework 4 (FW4)) present in the product of or derived from those human genes. Preferably the light chain variable region framework comprises FW1, FW2 and/or FW3, more preferably FW1, FW2 and FW3 present in the product of or derived from a human gene selected from the group consisting of IGKV1-33*01 (SEQ ID NO: 8), IGKV1D-33*01 (SEQ ID NO: 9), IGKV1D-12*02 (SEQ ID NO: 10), IGKV1D-12*01 (SEQ ID NO: 11), and IGKV1-12*02 (SEQ ID NO: 12). Light chain framework region sequences as used herein include FW1 (position 1 to position 23), FW2 (position 35 to position 49), FW3 (position 57 to position 88) and FW 4 (position 98 to position 108), wherein the amino acid position is indicated utilizing the numbering system set forth in Kabat.

In some embodiments the present disclosure provides an antibody or fragment thereof comprising a light chain variable framework region that is the product of or derived from human gene IGKV1-33*01 (SEQ ID NO: 8) and wherein the light chain variable framework region comprises at least one amino acid modification from the corresponding framework region of the light chain variable region of the corresponding murine antibody.

In further aspect the antibody or fragment thereof comprises a light chain variable region sequence comprising the amino acid sequence of SEQ ID NO: 2. In further aspect the antibody or fragment thereof comprises a non-CDR region of a light chain variable region sequence which is at least 80% identical to the non-CDR region of the heavy chain variable region sequence of SEQ ID NO: 2.

In some embodiments the present disclosure provides an antibody or fragment thereof comprising a light chain sequence comprising the amino acid sequence selected from SEQ ID NO: 17 and SEQ ID NO: 25.

In some embodiments the present disclosure provides an antibody or fragment thereof comprising a light chain sequence comprising the amino acid sequence of SEQ ID NO: 17. Alternatively, the light chain variable framework region of the light chain sequence comprises at least one amino acid modification from the corresponding light chain variable framework region of the corresponding murine antibody.

The amino acid modification may comprise an amino acid substitution at an amino acid position selected from the group consisting of 5 and 34, wherein the amino acid position of each group member is indicated according to the Kabat numbering. Specifically the amino acid modification comprises an amino acid substitution selected from the group consisting of 5N, and 34S, preferably T5N and N34S, wherein the amino acid position of each group member is indicated according to the Kabat numbering. Particularly preferred is a light chain sequence comprising the amino acid sequence of SEQ ID NO: 17, without any amino acid modifications.

In some embodiments the antibody or fragment thereof that binds to TL1A comprises a heavy chain variable framework region that is the product of or derived from a human gene selected from the group consisting of IGHV1-2*02 (SEQ ID NO: 3), IGHV1-2*04 (SEQ ID NO: 4), IGHV1-2*05 (SEQ ID NO: 5). IGHV1-2*01 (SEQ ID NO: 6), and IGHV1-46*01 (SEQ ID NO: 7) and a light chain variable framework region that is the product of or derived from a human gene selected from the group consisting of IGKV1-33*01 (SEQ ID NO: 8), IGKV1D-33*01 (SEQ ID NO: 9), IGKV1D-12*02 (SEQ ID NO: 10), IGKV1D-12*01 (SEQ ID NO: 11), and IGKV1-12*02 (SEQ ID NO: 12), preferably a heavy chain variable framework region that is the product of or derived from human gene IGHV1-2*02 (SEQ ID NO: 3), and a light chain variable framework region that is the product of or derived from human gene IGKV1-33*01 (SEQ ID NO: 8). As well combinations of heavy chain variable framework regions which are present in the product of or derived from different human genes mentioned supra and/or of light chain variable region framework regions which are present in the product of or derived from different human genes mentioned supra are encompassed by the present invention.

Germline DNA sequences for human heavy and light chain variable region genes can be found in the "VBase" human germline sequence database (available on the Internet at www.mrccpe.cam.ac.uk/vbase), as well as in Kabat E A et al., supra; Tomlinson I M et al., (1992) J. Mol. Biol. 227: 776-798 and Cox J P L et al., (1994) Eur. J. Immunol. 24: 827-836. As another example, the germline DNA sequences for human heavy and light chain variable region genes can be found in the Genbank database.

In another aspect, the present disclosure also provides an antibody or fragment thereof that binds to TL1A, wherein at least one of the heavy chain CDRs and/or at least one of the light chain CDRs comprises at least one amino acid modification. Site-directed mutagenesis or PCR-mediated mutagenesis can be performed to introduce the modification(s) and the effect on antibody binding, or other functional property of interest, can be evaluated in in vitro or in vivo assays. Preferably conservative modifications are introduced. The modification(s) may be amino acid substitutions, additions or deletions, but are preferably substitutions. Typically, no more than five, preferably no more than four, more preferably no more than three, even more preferably no more than two, most preferably no more than one amino acid modifications are performed within a CDR region.

In certain embodiments, framework sequences can be used to engineer variable regions to produce variant antibodies. Variant antibodies of the invention include those in which modifications have been made to framework residues within VH and/or VK, e.g. to improve the properties of the antibody. Typically such framework modifications are made to decrease the immunogenicity of the antibody. For example, one approach is to "backmutate" one or more framework residues to the corresponding murine sequence or to "backmutate" one or more framework residues to a corresponding germline sequence.

Thus in a further aspect the present disclosure provides an antibody or fragment thereof that binds to TL1A, wherein at least one of the framework region sequences of the heavy chain variable region of the antibody or fragment thereof comprises at least one amino acid modification from the corresponding framework region of the heavy chain variable region of the corresponding murine antibody. Preferably the amino acid modification is an amino acid substitution. Typically, no more than seven, preferably no more than six, preferably no more than five, preferably no more than four, more preferably no more than three, even more preferably no more than two, most preferably no more than one amino acid modifications are performed within a framework region. In some embodiments the present disclosure provides an antibody or fragment thereof that binds to TL1A, wherein the amino acid modification of the framework regions of the heavy chain variable region comprise an amino acid substitution at amino acid position selected from the group consisting of 37, 48, 50, 67, 69, 71, and 75 and wherein the amino acid position of each group member is indicated according to the Kabat numbering. Preferred amino acid substitution of the framework regions of the heavy chain variable region are at amino acid positions selected from the group consisting of 37, 48, 50, 67 and 71. More preferred amino acid substitutions of the framework regions of the heavy chain variable region are selected from the group consisting of V37A, M48I, W50E, V67A, M69L. R71V and I75S, whereas V37A is the most preferred amino acid substitution of the framework regions of the heavy chain variable region.

The present disclosure also provides an antibody or fragment thereof that binds to TL1A, wherein at least one of the framework region sequences of the light chain variable region of the antibody or fragment thereof may comprise at least one amino acid modification from the corresponding framework region of the light chain variable region of the corresponding murine antibody. Preferably the amino acid modification is an amino acid substitution. Typically, no more than two, more preferably no more than one and most preferably, no amino acid modifications are performed within a framework region. In some embodiments the present disclosure provides an antibody or fragment thereof, wherein the amino acid modification of the framework regions of the light chain variable region sequence comprises an amino acid substitution at amino acid position selected from the group consisting of 5 and 34. The amino acid modifications of the framework regions of the light chain variable region sequence comprise a substitution selected from the group consisting of a 5N and 34S, preferably T5N and N34S and wherein the amino acid position of each group member is indicated according to the Kabat numbering. In some embodiments the antibody or fragment thereof of the present invention may comprise amino acid modifications of the framework regions of the heavy chain variable region sequence as set out above and amino acid modifications of the framework regions of the light chain variable region sequence as set out above.

The present disclosure also provides an antibody or fragment thereof that binds to TL1A that comprises a heavy chain variable region selected from the group consisting of SEQ ID NOS: 13, 26, 27, 28 and 29, preferably selected from the group consisting of SEQ ID NOS: 26, 27, 28 and 29, more preferably from the group consisting of SEQ ID NOS: 27, 28 and 29 and even more preferably from the group consisting of SEQ ID NOS: 27 and 29. The present disclosure also provides an antibody or fragment thereof that binds to TL1A that comprises a light chain variable region selected from the group consisting of SEQ ID NOS: 14 and 30, more preferably SEQ ID NO: 14. In some embodiments the antibody or fragment thereof that binds to TL1A comprises a heavy chain variable region selected from the group consisting of SEQ ID NOS: 26, 27, 28 and 29, and a light chain variable region selected from the group consisting of SEQ ID NOS: 14 and 30. Given that each of these heavy and light chain variable region sequences can bind to TL1A, the heavy and light chain variable region sequences can be "mixed and matched" to create anti-TL1A binding molecules of the invention. TL1A binding of such "mixed and matched" antibodies can be tested using the binding assays described e.g. in the Examples.

In some embodiments the antibody or fragment thereof that binds to TL1A comprises a heavy chain variable region selected from the group consisting of SEQ ID NOS: 27 and 29, and a light chain variable region selected from the group consisting of SEQ ID NOS: 14 and 30. In more preferred embodiments the antibody or fragment thereof that binds to TL1A comprises a heavy chain variable region comprising the amino acid sequence of SEQ ID NO: 27 and a light chain variable region comprising the amino acid sequence of SEQ ID NO: 14 or a heavy chain variable region comprising the amino acid sequence of SEQ ID NO: 29 and a light chain variable region comprising the amino acid sequence of SEQ ID NO: 14. Most preferred is an antibody or fragment thereof that binds to TL1A comprising a heavy chain variable region selected from the group consisting of SEQ ID NOS: 27 and 29, and a light chain variable region comprising the amino acid sequence of SEQ ID NO: 14.

The present disclosure also provides an antibody or fragment thereof that binds to TL1A that comprises a heavy chain sequence selected from the group consisting of SEQ ID NOS: 16, 21, 22, 23 and 24, preferably selected from the group consisting of SEQ ID NOS: 22, 23 and 24 and more preferably from the group consisting of SEQ ID NOS: 22 and 24. The present disclosure also provides an antibody or fragment thereof that binds to TL1A that comprises a light chain sequence selected from the group consisting of SEQ ID NOS: 17 and 25, more preferably SEQ ID NO: 17. In some embodiments the antibody or fragment thereof that binds to TL1A comprises a heavy chain sequence selected from the group consisting of SEQ ID NOS: 21, 22, 23 and 24, and a light chain sequence selected from the group consisting of SEQ ID NOS: 17 and 25. Given that each of these heavy and light chain variable region sequences can bind to TL1A, the heavy and light chain variable region sequences can be "mixed and matched" to create anti-TL1A binding molecules of the invention. TL1A binding of such "mixed and matched" antibodies can be tested using the binding assays described e.g. in the Examples.

In some embodiments the antibody or fragment thereof that binds to TL1A comprises a heavy chain sequence selected from the group consisting of SEQ ID NOS: 22 and 24, and a light chain sequence selected from the group consisting of SEQ ID NOS: 17 and 25. In more preferred embodiments the antibody or fragment thereof that binds to TL1A comprises a heavy chain sequence comprising the amino acid sequence of SEQ ID NO: 22 and a light chain sequence comprising the amino acid sequence of SEQ ID NO: 17 or a heavy chain sequence comprising the amino acid sequence of SEQ ID NO: 24 and a light chain sequence comprising the amino acid sequence of SEQ ID NO: 17. Most preferred is an antibody or fragment thereof that binds to TL1A comprising a heavy chain sequence selected from the group consisting of SEQ ID NOS: 22 and 24, and a light chain sequence comprising the amino acid sequence of SEQ ID NO: 17.

In one embodiment of the present disclosure, the antibody or fragment thereof is a humanized antibody. Preferably, the antibody or fragment thereof is a humanized monoclonal antibody.

The present disclosure also provides a monovalent antibody or fragment thereof that binds to TL1A. i.e. an antibody which consists of a single antigen binding arm. The present disclosure also provides a fragment of a antibody that binds to TL1A selected from the group consisting of Fab, Fab', Fab'-SH, Fd. Fv, dAb, F(ab')2, scFv, bispecific single chain Fv dimers, diabodies, triabodies and scFv genetically fused to the same or a different antibody. Preferred fragments are scFv, bispecific single chain Fv dimers and diabodies. The present disclosure also provides a full length antibody that binds to TL1A.

The present disclosure also provides an antibody or fragment thereof that binds to TL1A which further comprises a heavy and/or light constant region in particular a human heavy and/or a human light constant region. Human heavy constant regions may be selected from the group of human immunoglobulins consisting of IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), or IgE (IGHE), whereas the human heavy constant region IgG, in particular IgG1 (IGHG1) is preferred. Human light constant region may be selected from the group of human immunoglobulins consisting of kappa or lambda constant regions, whereas human kappa constant region is preferred. In a preferred embodiment the antibody or fragment thereof that binds to TL1A comprises a human IgG1 (IGHG1) heavy constant domain and a human light kappa constant domain.

In addition or alternative to modifications made within the framework regions or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation. Each of these embodiments is described in further detail below. Modifications within the Fc region as outlined below are according to the EU numbering of residues in the Fc region. In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody. In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al. In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In a further embodiment Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al. In another example, one or more amino (which is usually a native human IgG1l), i.e. as compared to an antibody or fragment thereof that binds to TL1A that only differs from the isotypic variant with regard to the modified heavy constant region.

The present disclosure also provides an antibody or fragment thereof that binds to TL1A which comprises a human IgG Fc region, wherein the mature core carbohydrate structure attached to the human IgG Fc region lacks fucose (referred herein alternatively as "non fucosylated"). The term "mature core carbohydrate structure" as used herein includes a processed core carbohydrate structure attached to an Fc region which generally consists of the carbohydrate structure GlcNAc (Fucose)-GlcNAc-Man-(Man-GlcNAc)$_2$ typical of biantennary oligosaccharides represented schematically below:

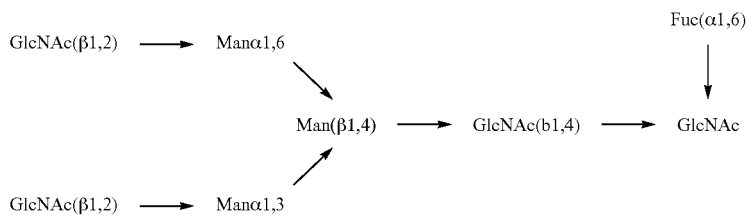

acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 to 238 in the N-terminal region of the CH2 domain are altered to thereby alter the ability of the antibody to fix complement. This approach is described further in PCT Publication WO94/29351 by Bodmer et al. In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO00/42072 by Presta.

The present disclosure also provides an antibody or fragment thereof that binds to TL1A comprising human heavy and/or light constant regions, wherein the human heavy constant region comprises an isotypic variant comprising the CH1 region, the hinge region, the CH2 region and CH3 region from human IgG4 (IGHG4) and wherein the hinge region comprises a substitution of serine at position 228 to proline. Preferably the antibody comprising the isotypic variant is a full length antibody. A particular preferred antibody or fragment thereof that binds to TL1A comprising an isotypic variant comprising the CH1 from human IgG4 (IGHG4), the hinge from human IgG4 (IGHG4), having S228P substitution and the CH2 and CH3 from human IgG4 (IGHG4). It has been found that the isotypic variant exhibits no Fc-mediated cytotoxicity mechanisms such as ADCC compared to an antibody or fragment thereof that binds to TL1A which comprises a human heavy constant region from human IgG1 (IGHG1)

This term specifically includes G-1 forms of the core mature carbohydrate structure lacking a β1,2 GlcNAc residue. Preferably, however, the core carbohydrate structure includes both β1.2 GlcNAc residues. The mature core carbohydrate structure herein generally is not hypermannosylated. The mature core carbohydrate structure is attached to the Fc region of the glycoprotein, generally via N-linkage to Asn297 of a CH2 domain of the Fc region.

Preferably the antibody comprises a human IgG1 (IGHG1) Fc region, wherein the mature core carbohydrate structure attached to the human IgG1 (IGHG1) Fc region lacks fucose. More preferred is a full-length antibody comprising a human IgG1 (IGHG1) Fc region, wherein the mature core carbohydrate structure attached to the human IgG1 (IGHG1) Fc region lacks fucose. It is known from WO03/035835 that lack of fucose in the mature core carbohydrate structure attached to the human IgG Fc region may enhance ADCC. Thus in a further embodiment the antibody or fragment thereof of the present disclosure comprises a human IgG1 (IGHG1) Fc region, wherein the mature core carbohydrate structure attached to the human IgG1 (IGHG1) Fc region lacks fucose, whereas the antibody lacking fucose exhibits enhanced ADCC compared to the parent antibody or fragment thereof not lacking fucose. Methods to generate antibodies which lack fucose are, for example (a) use of an engineered or mutant host cell that is deficient in fucose metabolism such that it has a reduced ability (or is unable to) fucosylate proteins expressed therein; (b) culturing cells under conditions which prevent or reduce fucosylation; (c) post-translational removal of fucose (e.g. with a fucosidase enzyme); (d) post-translational addition of the desired carbohydrate, e.g. after recombinant expression of a non-glycosylated glycoprotein; or (e) purification of the glycoprotein so as to select for product which is not fucosylated. Preferably used are methods described in Example 14 of WO10/095031 e,g. methods described in Longmore et al., (1982) Carbohydr. Res. 365-92 or in Imai-Nishiya et al., (2007), BMC Biotechnol. 7: 84.

Also provided by the present invention is an antibody or fragment thereof that binds to TL1A and which binds to the same epitope as the antibody comprising the heavy chain variable sequence comprising the amino acid sequence of SEQ ID NO. 27 or 29 and the light chain variable sequence comprising the amino acid sequence of SEQ ID NO. 14. Also provided by the present invention is a specific region or epitope of TL1A, which is bound by an antibody provided by the present invention, in particular by an antibody comprising the heavy chain variable sequence comprising the amino acid sequence of SEQ ID NO. 27 or SEQ ID NO 29 and the light chain variable sequence comprising the amino acid sequence of SEQ ID NO. 14. This specific region or epitope of the TL1A polypeptide can be identified by any suitable epitope mapping method known in the art in combination with any one of the antibodies provided by the present invention. Examples of such methods include screening peptides of varying lengths derived from TL1A for binding to the antibody of the present invention with the smallest fragment that can specifically bind to the antibody containing the sequence of the epitope recognised by the antibody. The TL1A peptides may be produced synthetically or by proteolytic digestion of the TL1A polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antibodies which bind the same epitope.

Anti-TL1A Antibody Properties

Standard assays to evaluate the binding ability of the antibodies toward e.g. TL1A are known in the art, including for example, ELISAs, BIAcore®. Western blots, RIAs, and flow cytometry analysis. Suitable assays are described in detail in the Examples. The binding kinetics (e.g., binding affinity like KD) of the antibodies also can be assessed by standard assays known in the art, such as by Scatchard or BIAcore® system analysis. The relative binding affinity $K_i$ can be assessed by standard competition assays known in the art.

In a further aspect the present invention provides antibodies or fragment thereof that bind to human, mouse, rat and cynomologus monkey TL1A as visualized by ELISA or BIAcore® methods. Binding ELISA can be carried out and measured according to Example 3.

In a further aspect the present invention provides antibodies or fragments thereof that bind to recombinant or naturally produced human TL1A and prevent activation and cytokine secretion by CD4 T lymphocytes. For example, the antibodies or fragments thereof of the invention may suppress the production of INFγ induced by immune complex stimulated monocytes. An assay to determine such TL1A-mediated cytokine secretion by CD4 T lymphocytes can be carried out and measured according to Examples 3 and 6.

In a further aspect the present invention provides antibodies or fragment thereof that bind to TL1A, in particular TL1A in isolated form, with an affinity ($K_D$) of 850 pM or less, preferably 700 nM or less, more preferably 300 nM or less, more preferably 260 nM or less, even more preferably 250 nM or less, e.g. measured by Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland: BR-1000-14) with a human soluble TL1A polypeptide (encoded by SEQ ID NO: 116) used as analyte as detailed in Example 5. In a preferred aspect, the present invention provides a humanized antibody or fragment thereof that retains at least 85% of the TL1A binding affinity ($K_D$) of the corresponding chimeric antibody. Preferably the humanized antibody or fragment thereof retains at least 90% of the TL1A binding affinity ($K_D$) of the corresponding chimeric antibody, more preferably at least 95% of the binding affinity ($K_D$) of the corresponding chimeric antibody. Preferably, the humanized antibody or fragment thereof binds human TL1A with equivalent affinity to the corresponding chimeric antibody. By "equivalent affinity" is meant an affinity value that is within a range of ±10% of the TL1A binding affinity of the corresponding chimeric antibody. More preferably, the present invention provides a humanized antibody or fragment thereof that binds human TL1A with a higher affinity than the corresponding chimeric antibody. Preferably the humanized antibody or fragment thereof binds human TL1A with two-fold higher affinity than the corresponding chimeric antibody, more preferably with three-fold higher affinity than the corresponding chimeric antibody. In a preferred aspect of the present invention, humanized antibodies or fragment thereof that bind to human TL1A are provided that have a binding affinity ($K_D$) of 900 pM or less, 700 pM or less, preferably 500 pM or less, more preferably 300 nM or less, more preferably 260 pM or less, even more preferably 250 pM or less e.g. measured by Surface Plasmon Resonance (SPR) on a BIAcore® instrument (GE Healthcare Europe GmbH, Glattbrugg, Switzerland) by capturing the antibody on a protein-A coupled CM5 research grade sensor chip (GE Healthcare Europe GmbH, Glattbrugg, Switzerland; BR-1000-14) with a human soluble TL1A polypeptide (encoded by SEQ ID NO: 116) used as analyte as detailed in Example 5.

A further aspect of the present invention provides antibodies or fragments thereof that bind to TL1A and which have good thermal stability. In a preferred embodiment, an antibody or fragment thereof that binds to TL1A has a FAB fragment thermostability temperature greater than 70° C., preferably greater than 75° C. and even more preferably greater than 80° C. For analysis of FAB fragment thermostability differential scanning calorimetry measurements are used, whereas a mid-point melting temperature of the FAB fragment in context of a full-length IgG is identified. These kind of calorimetric measurements are known to the skilled person and can be carried out according to e.g. Garber E & Demarest S J (2007) Biochem Biophys Res Commun, 355: 751-7, as further described in Example 5.

Nucleic Acids, Vectors and Host Cells

The present disclosure also provides isolated nucleic acids encoding the antibodies and fragments thereof that bind to TL1A, vectors and host cells comprising the nucleic acid or the vector. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g. F. Ausubel, et al., ed. (1987) Current Protocols in Molecular Biology, Greene Publishing and Wiley Interscience, New York. A nucleic acid of the invention can be, for example. DNA or RNA and may or may not contain intron sequences. In a preferred embodiment, the nucleic acid is a cDNA molecule.

Nucleic acids of the invention can be obtained using standard molecular biology techniques e.g. cDNAs encoding the light and heavy chains of the antibody or encoding VH and VL segments can be obtained by standard PCR amplification or cDNA cloning techniques. For antibodies obtained from an immunoglobulin gene library (e.g., using phage display techniques), one or more nucleic acids encoding the antibody can be recovered from the library. The methods of introducing exogenous nucleic acid into host cells are well known in the art, and will vary with the host cell used. Techniques include but are not limited to dextran-mediated transfection, calcium phosphate precipitation, calcium chloride treatment, polyethylenimine mediated transfection, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

Preferred nucleic acids molecules of the invention are those encoding the heavy chain sequence selected from the group consisting of SEQ ID NOS: 42, 43, 44, 45 and 46 and/or the light chain sequence selected from the group consisting of SEQ ID NOS: 47 and 48. Preferred nucleic acids molecules of the invention are those encoding the heavy chain variable region selected from the group consisting of SEQ ID NOS: 31, 32, 33, 34 and 35 and/or the light chain variable region selected from the group consisting of SEQ ID NOS: 36 and 37.

Preferred nucleic acids molecules of the invention are those encoding the heavy chain variable region of SEQ ID NO: 1 and/or the light chain variable region of SEQ ID NO: 2, e.g. DNA encoding the heavy chain variable region comprising the nucleic acid sequence of SEQ ID NO: 63 and/or DNA encoding the light chain variable region comprising the nucleic acid sequence of SEQ ID NO: 64. More preferred nucleic acid molecules of the invention are those encoding the heavy chain variable region of SEQ ID NOS: 27 or 29 and/or the light chain variable region of SEQ ID NO: 14. e.g. DNA encoding the heavy chain variable region comprising the nucleic acid sequence of SEQ ID NOS: 33 or 35 and/or DNA encoding the light chain variable region comprising the nucleic acid sequence of SEQ ID NO: 36, which are most preferred.

Once DNA fragments encoding VH and VL segments are obtained, these DNA fragments can be further manipulated by standard recombinant DNA techniques, for example to convert the variable region genes to full-length antibody chain genes, or to fragments genes corresponding to the fragments described supra like Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat E A et al., supra) and DNA fragments encompassing these regions can be obtained by standard PCR amplification. The heavy chain constant region can be an IgG1 (IGHG1), IgG2 (IGHG2), IgG3 (IGHG3), IgG4 (IGHG4), IgA1 (IGHA1), IgA2 (IGHA2), IgM (IGHM), IgD (IGHD), or IgE (IGHE) constant region, but most preferably is an IgG1 (IGHG1) constant region. For a Fab fragment heavy chain gene, the VH-encoding DNA can be operatively linked to another DNA molecule encoding only the heavy chain CH1 constant region. The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat E A et al., supra.) and DNA fragments encompassing these regions can be obtained by standard PCR amplification. In preferred embodiments, the light chain constant region can be a kappa or lambda constant region, preferably a kappa constant region. To create a scFv gene, the VH- and VL-encoding DNA fragments are operatively linked to another fragment encoding a flexible linker, e.g., encoding the amino acid sequence (Gly-4-Ser)3, such that the VH and VL sequences can be expressed as a contiguous single-chain protein, with the VL and VH regions joined by the flexible linker (see e.g., Bird R E et al., (1988) Science, 242: 423-426; Huston J S et al., (1988) Proc. Natl. Acad. Sci. USA, 85: 5879-83; McCafferty J et al., (1990) Nature, 348: 552-554). Various techniques have been developed for the production of antibody fragments of antibodies. Traditionally, these fragments were derived via proteolytic digestion of intact antibodies (see, e.g., Morimoto K et al., (1992) J. Biochem. & Biophysical Methods, 24: 107-117 and Brennan M et al., (1985) Science, 229: 81-3). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter P et al., (1992) Bio/Technology, 10: 163-167). According to another approach. F(ab')2 fragments can be isolated directly from recombinant host cell culture. Other techniques for the production of antibody fragments will be apparent to the skilled practitioner. In other embodiments, the antibody of choice is a single-chain Fv fragment (scFv), see e.g. WO 1993/16185: U.S. Pat. No. 5,571,894 and U.S. Pat. No. 5,587,458. The antibody fragment may also be a "linear antibody", e.g., as described in U.S. Pat. No. 5,641,870, for example.

The nucleic acids that encode the antibodies of the present invention may be incorporated into a vector, preferably an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus vectors, preferably expression vectors, which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology, Methods in Enzymology 185, Academic Press, San Diego, Calif. (1990)). Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

Suitable host cells for cloning or expressing the DNA in the vectors herein are prokaryote, yeast, or higher eukaryote cells. Suitable prokaryotes for this purpose include eubacteria, including gram-negative or gram-positive organisms, for example, Enterobacteriaceae such as *Escherichia*, e.g., *E. coli, Enterobacter, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *E. coli* W3110 (ATCC 27,325). In addition to prokaryotes, eukaryotic microbes such as filamentous fungi or yeast are suitable cloning or expression hosts. *Saccharomyces cerevisiae*, or common baker's yeast, is the most commonly used among lower eukaryotic host microorganisms. However, a number of other genera, species, and strains are commonly available and useful, such as *Schizosaccharoriyces pombe; Kluyveromyces* hosts including *K. lactis, K. fragilis* (ATCC 12,424), *K. bulgaricus* (ATCC 16,045), *K. wickeramii* (ATCC 24,178), *K. WaltH* (AJCC 56,500), *K. drosopmarum* (ATCC 36,906), *K. thermotolerans*, or *K. marxianusyarrowia* (EP402226); *Pichia pastoris* (EP 183070); *Candida; Trichoderma reesia* (EP244234); *Neurospora crassa; Schwanniomyces* such as *Schwanniomyces occidentalis*: and filamentous fungi including *Neurospora, Penicillium, Tolypocladium*, or *Aspergillus* hosts such as *A. nidulans* or *A. niger*.

Suitable host cells for the expression of the antibodies of the invention are derived from multicellular organisms. Examples of invertebrate cells include plaril and insect cells. Numerous baculoviral strains and variants and corresponding permissive insect host cells from hosts such as *Spodoptera frugiperda* (caterpillar), *Aedes augypti* (mosquito), *Aedes albopictus* (mosquito), *Drosophila melanogaster* (fruitfly) and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells. Plant cell cultures of cotton, corn, potato, soybean, petunia, tomato, and tobacco can also be utilized as hosts.

Host cells for expressing the recombinant antibodies of the invention are preferably mammalian host cells which include Chinese Hamster Ovary (CHO cells) (including dhfr⁻ CHO cells, described in Urlaub G & Chasin L A (1980) Proc. Natl. Acad. Sci, USA, 77: 4216-4220, used with a DHFR selectable marker, e.g., as described in Kaufman R J & Sharp P A (1982) J. Mol. Biol, 159: 601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP338841 (to Bebbington). When recombinant antibody genes are introduced into mammalian host cells, the antibodies are produced by culturing the host cells for a period of time sufficient to allow for expression of the antibody in the host cells or, more preferably, for secretion of the antibody into the culture medium in which the host cells are grown. Host cells useful for producing antibodies that bind to TL1A may be cultured in a variety of media. Commercially available media such as Ham's F10 (Sigma-Aldrich Chemie GmbH, Buchs, Switzerland), Minimal Essential Medium (MEM; Sigma-Aldrich Chemic GmbH), RPMI-1640 (Sigma-Aldrich Chemie GmbH, Basel, Switzerland), and Dulbecco's Modified Eagle's Medium ((DMEM; Sigma-Aldrich Chemie GmbH) are suitable for culturing the host cells. Antibodies can be recovered from the culture medium using standard protein purification methods.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs antibody and any associated fusion partners to a desired cellular location or to the extracellular media. As is known in the art, certain signalling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. Ni$^{+2}$ affinity columns)), GST fusions. MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both.

Construction and Production of Antibodies

Antibodies generated against the TL1A polypeptide may be obtained by immunisation of an animal i.e. by administering the polypeptides to an animal, preferably a non-human animal, using well-known and routine protocols, see for example Handbook of Experimental Immunology (Weir D M (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats in particular mice are generally most suitable. Antibodies can be produced as well by recombinant DNA techniques known to the skilled person. In additional antibodies can be produced by enzymatic or chemical cleavage of naturally occurring antibodies. Humanized antibodies of the present invention may be constructed by transferring one or more CDRs or portions thereof from VH and/or VL regions from a non-human animal (e.g., mouse) to one or more framework regions from human VH and/or VL regions. Optionally, human framework residues thus present in the VH and/or VL regions may be replaced by corresponding non-human (e.g., mouse) residues when needed or desired for decreasing immunogenicity of the antibody and/or maintaining binding affinity. Optionally, nonhuman amino acid residues present in the CDRs may be replaced with human residues. Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693.762 and 6,180,370 to Queen et al.).

Humanized antibodies of the present invention may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region elude homology in CDR length between the murine donor molecule and the human acceptor molecule. Human acceptor antibody molecules are preferably selected by homology search to the V-BASE database, although other databases such as the Kabat and the public NCBI databases may be used as well.

Humanized antibodies of the present invention may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well. Methods for humanizing a non-human antibody are described herein, including in Example 5, below.

The present invention provides a method of producing an antibody or fragment thereof that binds to TL1A comprising culturing a host cell comprising an isolated nucleic acid encoding the antibody or fragment thereof that binds to TL1A or a vector comprising an isolated nucleic acid encoding the antibody or fragment thereof that binds to TL1A so that the nucleic acid is expressed and the antibody produced. Preferably the antibody is isolated. For host cells, nucleic acids and vectors, the ones described above can be used. Expression of the nucleic acids can be obtained by, e.g. a combination of recombinant DNA techniques and gene transfection methods as is well known in the art (e.g. Morrison S (1985) Science 229: 1202) and as further outlined above. For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into vectors such as expression vectors. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH1 segment(s) within the vector and the VK segment is operatively linked to the CK segment within the vector.

Characterization and Purification of Anti-TL1A Antibodies

Screening for antibodies can be performed using assays to measure binding to TL1A and/or assays to measure the ability to block the binding of TL1A to its receptor TNFRSF25. An example of a binding assay is an ELISA, in particular, using a fusion protein of TL1A and human Fc, which is immobilized on plates, and employing a conjugated secondary antibody to detect anti-TL1A antibody bound to the fusion protein. An example of a blocking assay is a flow cytometry based assay measuring the blocking of TL1A fusion protein binding to TNFRSF25 on human CD4 cells. A fluorescently labelled secondary antibody is used to detect the amount of TL1A fusion protein binding to the cell. This assay is looking for a reduction in signal as the antibody in the supernatant blocks the binding of ligand fusion protein to TNFRSF25. A further example of a blocking assay is an assay where the blocking of costimulation of naive human T cells mediated by TL1A fusion protein coated to a plate is measured by measuring thymidine incorporation. As an assay for evaluating the functional activity of anti-TL1A antibodies e.g. the reduction of cytokine secretion by CD4 T lymphocytes as described in Examples 3 and 6 can be used.

Antibodies of the present invention may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. To purify TL1A antibodies, selected host cells can be grown in e.g. spinner-flasks for monoclonal antibody purification. Supernatants can be filtered and concentrated before affinity chromatography with protein A-sepharose (Pharmacia, Piscataway, N.J.). Eluted antibodies can be checked by gel electrophoresis and high performance liquid chromatography to ensure purity. A preferred antibody of the present invention is thus an isolated and/or purified antibody that binds to TL1A.

Immunoconjugates

In another aspect, the present invention provides a TL1A antibody or a fragment thereof that binds to TL1A, linked to a therapeutic agent, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be linked to an antibody of the invention include duocarmycins, calicheamicins, maytansines and auristatins, and derivatives thereof. An example of a calicheamicin antibody conjugate is commercially available (Mylotarg®; American Home Products). Cytotoxins can be linked to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito G et al., (2003) Adv. Drug Deliv. Rev. 55: 199-215: Trail P A et al. (2003) Cancer Immunol. Immunother. 52: 328-337; Payne G (2003) Cancer Cell, 3: 207-212; Allen T M (2002) Nat. Rev. Cancer, 2: 750-763; Pastan I & Kreitman R J (2002) Curr. Opin. Investig. Drugs, 3: 1089-1091; Senter P D & Springer C J, (2001) Adv. Drug Deliv. Rev. 53: 247-264. Antibodies of the present invention also can be linked to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine[131], indium[111], yttrium[90] and lutetium[177]. Methods for preparing radio-immunoconjugates are established in the art. Examples of radioimmunoconjugates are commercially available, including Zevalin® (EDEC Pharmaceuticals) and Bexxar® (Corixa Pharmaceuticals) and similar methods can be used to prepare radioimmunoconjugates using the antibodies of the invention. The antibody immunoconjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Techniques for linking such therapeutic agents to antibodies are well known, see, e.g., Arnon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985); "Analysis, Results, and Future Prospective of the Therapeutic Use of Radiolabeled Antibody in Cancer Therapy", in Monoclonal Antibodies for Cancer Detection and Therapy, Baldwin et al., (eds.), pp. 303-16 (Academic Press 1985), and Thorpe P E & Ross W C (1982) Immunol. Rev. 62: 119-58.

In another aspect, the present invention provides a TL1A antibody or a fragment thereof that binds to TL1A, administered together with a therapeutic agent, such as a cytotoxin, a drug (e.g., an immunosuppressant) or a radiotoxin.

Pharmaceutical Compositions

In another aspect, the present invention provides a composition. e.g., a pharmaceutical composition, comprising the antibody or fragment thereof, of the present invention, and a pharmaceutically acceptable carrier. Such compositions may include one or a combination of (e.g., two or more different) antibodies, and/or immunoconjugates of the invention and/or a therapeutic agent, such as a cytotoxin, a drug (e.g., an immunosuppressant) or a radiotoxin as described supra. For example, a pharmaceutical composition of the invention can comprise a combination of antibodies (or immunoconjugates) that bind to different epitopes on the target antigen or that have complementary activities. Pharmaceutical compositions of the invention also can be administered in combination therapy, i.e., combined with other agents. For example, the combination therapy can include a TL1A antibody of the present invention combined with at least one other anti-inflammatory or immunosuppressant agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or immunoconjugate, may be coated in a material to protect the compound from the action of acids and other natural conditions that may inactivate the compound. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

In another aspect, the present invention provides a composition comprising an immunoconjugate comprising the antibody or fragment thereof that binds to TL1A linked to a therapeutic agent and a pharmaceutically acceptable carrier. Immunoconjugates and therapeutic agents which can be used are as described supra.

In another aspect, the present invention provides a composition comprising the antibody or fragment thereof of the present invention which further comprises another pharmaceutically active agent. Preferably the another pharmaceutically active agent is one or more of: a) another antagonist to TL1A, b) an anti-inflammatory agent, c) an immune suppressive agent e.g. TNFα antagonist, cortisone or steroids etc) and/or d) an anti-allergy agent.

A pharmaceutical composition of the invention may also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic-acid (EDTA), sorbitol, tartaric acid, phosphoric acid, and the like. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic and Other Uses

The antibodies of the present invention have numerous in vitro and in vivo diagnostic and therapeutic utilities involving the diagnosis and treatment of TL1A mediated disorders. For example, these molecules can be administered to cells in culture, in vitro or ex vivo, or to human subjects, e.g., in vivo, to treat, prevent and to diagnose a variety of TL1A-mediated disorders. Preferred subjects are human and include patients having disorders mediated by TL1A activity (TL1A mediated disorders). The neutralizing antibodies of the present invention can be effective in treating patients independent of their TL1A costimulatory status. More preferred subjects are human and include patients expressing a high level of TL1A.

A "patient" for the purposes of the present invention includes both humans and other animals, preferably mammals and most preferably humans. Thus the antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an antibody prior to onset of the disease results in treatment of the disease. As another example, successful administration of an antibody after clinical manifestation of the disease to combat the symptoms of the disease comprises treatment of the disease. "Treatment" and "treating" also encompasses administration of an antibody after the appearance of the disease in order to eradicate the disease. Successful administration of an antibody after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In a particular embodiment, the antibodies are used in vivo to treat, prevent or diagnose a variety of TL1A-mediated disorders. Thus the invention provides a method for treating a TL1A mediated disorder in a subject, the method comprising administering to the subject a therapeutically effective amount of the antibody or fragment thereof. Exemplary TL1A mediated disorders include, but are not limited to, inflammatory diseases and/or autoimmune diseases, for example, inflammatory bowel disease (IBD) including ulcerative colitis and Crohn's disease, rheumatoid arthritis, MS, type 1 and type 2 diabetes, psoriasis, psoriatic arthritis, ankylosing spondylitis, atopic dermatitis; allergic reactions or conditions, including for example, asthma and allergic lung inflammation; cancers, atherosclerosis, infections, neurodegenerative diseases, graft rejection, graft versus host diseases (GVHD) and cardiovascular disorders/diseases. The invention also provides a method for treating a TL1A mediated disorder in a subject, the method comprising administering to the subject a therapeutically effective amount of the antibody or fragment thereof. Exemplary TL1A mediated disorders include, but are not limited to, inflammatory diseases and/or autoimmune diseases, for example, inflammatory bowel disease (IBD) including ulcerative colitis and Crohn's disease, rheumatoid arthritis, MS, type 1 and type 2 diabetes, psoriasis, psoriatic arthritis, ankylosing spondylitis, atopic dermatitis; allergic reactions or conditions, including for example, asthma and allergic lung inflammation; cancers, atherosclerosis, infections, neurodegenerative diseases, graft rejection, graft versus host diseases (GVHD) and cardiovascular disorders/diseases, chronic obstructive pulmonary disease COPD, optic neuritis, age related macular degeneration, systemic lupus erythematosus (SLE), sjogen's syndrome, scleroderma, systemic sclerosis, chronic Kidney disease, liver fibrosis, tuberculosis, idiopathic pulmonary fibrosis, tuberculosis induced lung fibrosis, retroperitoneal Fibrosis, pulmonary fibrosis, cystic fibrosis, endomyocardial fibrosis, atrial fibrosis, mediastinal fibrosis, myelofibrosis (bone marrow), retroperitoneal fibrosis, progressive massive fibrosis, pephrogenic systemic fibrosis, arthrofibrosis. Preferably, the TL1A mediated disorders include inflammatory diseases and/or auto immune diseases, including inter alia inflammatory bowel diseases (e.g., ulcerative colitis and Crohn's disease), rheumatoid arthritis, MS and atherosclerosis.

Preferred TL1A mediated disorders to be treated with the antibody of the invention are selected from the group consisting of inflammatory bowel disease, multiple sclerosis, rheumatoid arthritis and asthma. A particular preferred TL1A mediated disorder to be treated with the antibody of the invention is inflammatory bowel disease.

Animal model for evaluating the functional activity of anti-TL1A antibodies in TL A-mediated disorders are described in Example 7 for asthma and in Examples 8 and 9 for IBD.

In one embodiment, the antibodies of the invention can be used to detect levels of TL1A, or levels of cells which contain TL1A on their membrane surface, which levels can then be linked to certain disease symptoms. Alternatively, the antibodies can be used to inhibit or block TL1A function which, in turn, can be linked to the prevention or amelioration of certain disease symptoms, thereby implicating TL1A as a mediator of the disease. This can be achieved by contacting a sample and a control sample with the TL1A antibody under conditions that allow for the formation of a complex between the antibody and TL1A. Any complexes formed between the antibody and TL1A are detected and compared in the sample and the control. In light of the specific binding of the antibodies of the invention for TL1A, the antibodies of the invention can be used to specifically detect TL1A expression on the surface of cells e.g. can be used to detect a patient having low or high expression levels of TL1A. The antibodies of the invention can also be used to purify TL1A via immunoaffinity purification.

In another embodiment, the antibodies of the invention can be initially tested for binding activity associated with therapeutic or diagnostic use in vitro. For example, compositions of the invention can be tested using flow cytometric assays.

The present disclosure further provides the use of an antibody or fragment thereof as a medicament and the use of an antibody or fragment thereof in the preparation of a medicament for the treatment of a TL1A mediated disorder. In a further embodiment the present disclosure provides the antibody or fragment thereof for use as a medicament. Also provided by the present disclosure is the antibody or fragment thereof for use in a method for treating a TL1A mediated disorder. TL1A mediated disorders are the ones as described supra. The antibody or fragment thereof of the present invention may be particularly useful for treating TL1A mediated disorders independent of the DR3 costimulatory status of a patient. In a preferred embodiment, the antibody or fragment thereof can be used for treating a TL1A mediated disorder wherein a patient expresses a high level of TL1A.

As previously described, anti-TL1A antibodies of the invention can be co-administered with one or other more therapeutic agents, e.g., a cytotoxic agent, a radiotoxic agent or an immunosuppressive agent. The antibody can be linked to the agent (as an immunoconjugate as described supra) or can be administered separate from the agent. In the latter case (separate administration), the antibody can be administered before, after or concurrently with the agent or can be co-administered with other known therapies, e.g., an anti-cancer therapy, e.g. radiation.

For administration of the antibody, the dosage ranges from about 0.0001 to 100 mg/kg, and more usually 0.01 to 10 mg/kg, of the host body weight. An exemplary treatment regime entails administration once per week, once every two weeks, once every three weeks, once every four weeks, once a month, once every three months or once every three to six months. The antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml. Alternatively the antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated.

Actual dosage levels of the active ingredients, i.e. the antibody in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of a TL1A antibody of the invention preferably results in a decrease in severity of disease symptoms, an increase in frequency and duration of disease symptom-free periods, and/or a prevention of impairment or disability due to the disease affliction. The ability of a compound for the treatment of a TL1A mediated disorder can be evaluated in an animal model system predictive of efficacy in human. Alternatively, this property of a composition can be evaluated by examining the ability of the compound to inhibit cell growth, such inhibition can be measured in vitro by assays known to the skilled practitioner. One of ordinary skill in the art would be able to determine such amounts based on such factors as the subject's size, the severity of the subject's symptoms, and the particular composition or route of administration selected.

The antibody or the composition of the present invention can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by injection or infusion. More preferred routes of administration are intravenous or subcutaneous. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, for example, intranasally, orally, vaginally, rectally, sublingually or topically.

Article of Manufacture and Kit

In another embodiment of the disclosure, an article of manufacture comprising the antibody or fragment thereof, the composition or the immunoconjugate of the invention for the treatment of a TL1A mediated disorder is provided. The article of manufacture may comprise a container and a label or package insert on or associated with the container. Suitable containers include, for example, bottles, vials or syringes. The containers may be formed from a variety of materials such as glass or plastic. The container holds a composition that may be effective for treating the condition and may have a sterile access port (e.g., the container may be an intravenous solution bag or a vial having a stopper pierceable by a hypodermic injection needle). At least one active agent in the composition may be the antibody described herein. The label or package insert may indicate that the composition may be used for treating the condition of choice, such as cancer. In one embodiment, the label or package insert may indicate that the composition comprising the antibody may be used to treat a TL1A-mediated disorder.

Moreover, the article of manufacture may comprise (a) a first container with a composition contained therein, wherein the composition comprises the antibody herein, and (b) a second container with a composition contained therein, wherein the composition comprises a therapeutic agent other than the antibody. The article of manufacture in this embodiment of the disclosure may further comprise a package insert indicating that the first and second compositions can be used in combination to treat a TL1A mediated disease or disorder. Such therapeutic agent may be any of the adjunct therapies described in the preceding section (e.g., a thrombolytic agent, an anti-platelet agent, a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Also within the scope of the present invention are kits comprising the antibody, the compositions or the immunoconjugates of the invention and instructions for use. The kit can further contain one more additional reagents, such as an immunosuppressive reagent, a cytotoxic agent or a radiotoxic agent, or one or more additional antibodies of the invention (e.g., an antibody having a complementary activity which binds to an epitope in the TL1A antigen distinct from the first antibody).

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Generation and Screening of Mouse Anti-Human TL1A Antibodies

To produce the recombinant human TL1A-Fc protein, a cDNA for the human TL1A gene was purchased from Source BioScience (Nottingham, UK; clone number: IRATp970G02115D). This cDNA was used as a template to amplify the coding region of the processed secreted version of human TL1A (SEQ ID NO: 116) using PCR. The PCR was performed using primers GlnPr994 and GlnPr995 (SEQ ID NOs: 119 and 120, respectively). Primer GlnPr994 adds a BamHI restriction site 5' of the extracellular region and cleaves the native signal peptide. Primer GlnPr995 adds a HindIII restriction site 3' of the extracellular region. The amplicon was cut using the flanking restriction sites BamHI and HindIII and cloned into a modified mammalian expression vector based on the pcDNA3.1(−) plasmid from Invitrogen (Invitrogen AG, Basel, Switzerland), expressing an Fc-fusion construct. The expression vector contains the human CMV promoter with the Ig donor acceptor fragment (first intron) described in U.S. Pat. No. 5,924,939, the OriP sequence (Koons M D et al., (2001) J. Virol. 75(22): 10582-92), the SV40 enhancer, and the SV40 polyA fused to the gastrin terminator as described by Kim D, et al., (2003) Biotechnol. Prog. 19(5): 1620-2. The expression cassette contains a kozak region upstream of the open reading frame of the Fc fusion protein, followed by a signal peptide, terminated by a BamHI restriction site for convenient cloning. The Fc region of the fusion protein is started by a HindIII restriction site for convenient cloning, followed by a small glycine-serine linker. In order to release the previous construct upstream of the Fc region, the vector was cut using BamHI (NEB, Ipswich, Mass., USA) and HindIII (NEB. Ipswich, Mass., USA), treated using CIP (NEB. Ipswich, Mass., USA) and gel purified. The insert coding for the extracellular region of human TL1A was ligated in the backbone and transformed in *E. coli* Top 10 cells (Life Technologies. Carlsbad, Calif. USA) leading to the Fc fusion expression construct (SEQ ID NO: 117). The first 20 amino acids of SEQ ID NO: 117 correspond to the signal sequence, which was not present in the final Fc fusion expression construct.

This recombinant plasmid allowed for expression of the human TL1A-Fc fusion protein in mammalian cells with secretion into the cell culture medium driven by the signal peptide. For recombinant protein production, the aforementioned recombinant vector was transfected into suspension-adapted HEK 293 EBNA cells (Life Technologies, Carlsbad, Calif., USA) using jetPEI™ transfection reagent (Polyplus-transfection S.A., Strasbourg, France; Distributor: Brunschwig, Basel, Switzerland). The cell culture supernatant was collected after five days and further purified using a Protein A affinity purification column (HiTrap Protein A sepharose column; GE Healthcare Europe GmbH, Glattbrugg, Switzerland) operated on an ÄKTA FPLC system (GE Healthcare Europe GmbH, Glattbrugg, Switzerland).

To produce the secreted recombinant human TL1A protein with his-tag, the DNA sequence coding for the processed version of secreted human TL1A was amplified by PCR using primers GlnPr1542 and GlnPr1543 (SEQ ID NOs: 121 and 122, respectively) adding an N-terminal 6×His linker. A second round of PCR using primers GlnPr1544 (SEQ ID NO: 123) and GlnPR1543 adds a signal peptide and convenient flanking restriction sites for cloning (5': NheI; 3': XhoI). The PCR product was cut using NheII and XhoI (NEB. Ipswich, Mass., USA) and subsequently cloned in the modified pcDNA3.1(−) plasmid described above, cut using the same enzymes and CIPed. This restriction digest releases the open reading frame of the entire Fc-fusion protein previously present in the expression vector. After ligation and transformation in Top 10 *E. coli* cells, the final plasmid was chosen based on restriction digest and sequencing of the expression construct for secreted TL1A with an N-terminal his-tag (SEQ ID No: 118). The first 20 amino acids of SEQ ID NO: 118 correspond to the signal sequence, which was not present in the final N-terminal his-tag expression construct.

This recombinant plasmid allowed for the expression of the human TL1A-his protein in mammalian cells with secretion into the cell culture media. For protein production, the recombinant vector was transfected into suspension-adapted HEK 293 EBNA cells (Life Technologies, Carlsbad, Calif., USA) using jetPEI™ transfection reagent (Polyplus-transfection S.A., Strasbourg, France; Distributor: Brunschwig, Basel, Switzerland). The cell culture supernatant was collected five days after transfection and purified using a $Ni^{2+}$-NTA affinity purification column (HiTrap $Ni^{2+}$-NTA sepharose column; GE Healthcare Europe GmbH, Glattbrugg, Switzerland) operated on an ÄKTA FPLC system (GE Healthcare Europe GmbH, Glattbrugg, Switzerland). The buffer of the recombinant human TL1A-Fc and TL1A-his proteins was changed into phosphate buffer saline (PBS). Recombinant human TL1A-Fc protein dissolved in PBS was mixed with an equal volume of Stimune adjuvant (Prionics, Switzerland) and an emulsion was prepared. The emulsion was transferred to 0.5 mL insulin syringes (BD Pharmingen, Allschwil, Switzerland) and BALB/c animals (Harlan, Netherlands) were immunized sub-cutaneously in the back footpads, the base of the tail and the neck with 50 µg of the emulsified protein. The immunization was repeated two weeks later with the same amount of antigen and the same route of injection.

The presence of circulating anti-human TL1A antibodies in the immunized mouse sera was evaluated by direct ELISA using plates coated with the recombinant human TL1A-his protein. A serial dilution (from $1:10^0$ to $1:10^9$) of the different mouse sera was added to the plates and the bound antibodies were detected using a goat anti-mouse H+L whole molecule-HRP (Sigma-Aldrich Chemie GmbH, Buchs, Switzerland). A final subcutaneous boost with 50 µg of antigen without adjuvant was performed in animals displaying the best anti-human TL1A IgG serum titer three days before sacrifice.

Animals were euthanized and the inguinal, axillary, brachial, popliteal and sciatic lymph nodes were collected to prepare a single cell suspension by disturbing the lymph node architecture with two 25G needles in a DNAse (Roche Diagnostics (Schweiz) AG, Rotkreuz, Switzerland) and collagenase (Roche Diagnostics (Schweiz) AG, Rotkreuz, Switzerland) solution. Single cell suspensions were fused to a myeloma cell line X63AG8.653 (mouse BALB/c myeloma cell line; ATCC accession number: CRL 1580; Kearney J F et al., (1979) J. Immunol. 123(4): 1548-1550) at a ratio of 7:1 (fusion partner-to-harvested lymph node cells) with polyethylene glycol 1500 (Roche Diagnostics (Schweiz) AG, Rotkreuz, Switzerland). The fused cells were plated into 96 well flat bottom plates containing mouse macrophages in DMEM-10 medium (Invitrogen AG, Basel, Switzerland) supplemented with 10% fetal bovine serum (FBS, PAA Laboratories, Pasching, Austria), 2 mM L-glutamine, 100 U/ml (Biochrom AG, Germany) penicillin, 100 µg/ml streptomycin (Biochrom AG, Germany), 10 mM HEPES (Invitrogen AG, Basel, Switzerland), 50 µM β-mercaptoethanol (Sigma-Aldrich Chemie GmbH. Buchs, Switzerland), HAT (Sigma-Aldrich Chemie GmbH, Buchs, Switzerland) and 1% Growth factor (Hybridokine, Interchim/Uptima, Montluçon, France).

Approximately 800 wells from the fusions were screened by ELISA for the presence of mouse IgG that recognized human TL1A and blocked the binding of human TL1A to its receptor. Positive wells were expanded and subjected to two rounds of sub cloning. Cells were collected and the heavy and light chains were cloned and sequenced.

Example 2

Cloning and Sequencing of the VH and VL Chains of the Anti-TL1A Antibodies from Hybridoma Cells For each positively selected hybridoma, total RNA was prepared, reverse-transcribed into cDNA and VH and VL genes were respectively amplified by PCR. These PCR products were ligated into a rescue-vector (pDrive vector, QIAGEN AG, Hombrechtikon, Switzerland), allowing for the DNA sequencing of individual PCR products and the determination of mono- or poly-clonality of the selected hybridomas. This vector allowed for blue/white selection on LB-agar plates containing IPTG and X-gal (colonies with no insert were blue because of the degradation of X-gal by the LacZ α-peptide). Recombinant plasmids from positive (white) bacterial clones were prepared and sequenced using standard DNA sequencing primers specific for the vector backbone (M13rev, M13fwd, T7 or SP6). DNA sequences were finally subcloned into an expression vector for recombinant expression of the antibody of interest in mammalian cells.

RNA Isolation

Total RNA was isolated from $2\text{-}10\times10^6$ cells using the RNeasy Mini Kit from QIAGEN (QIAGEN AG, Hombrechtikon, Switzerland) according to the manufacturer's protocol; samples were quantified using a NanoDrop ND-1000 spectrophotometer (WITEC AG, Littau, Switzerland).

One Step RT-PCR

The total RNA preparations described above were further reverse-transcribed into cDNA, and the VH and VL fragments were amplified by PCR using two different mixtures of degenerated primers, each one allowing the recovery of all the different subfamilies of mouse immunoglobulin heavy chain variable fragments and variable heavy chain junction regions or the recovery of all mouse immunoglobulin light chain kappa variable fragments and variable light chain kappa junction regions. The primers used for reverse transcription and amplification were synthesized by Microsynth (Balgach, Switzerland), and were HPLC purified (Tables 1-4). Both reverse-transcription and PCR amplification were performed simultaneously using the QIAGEN one step RT-PCR kit (QIAGEN AG, Hombrechtikon, Switzerland). Since the technique used specific primers, each mRNA sample was then treated in duplicate allowing for the individual reverse-transcription and amplification of either the VH or the VL fragments. 2 µg of total RNA dissolved into RNase-free water to a final volume of 30 µl were mixed with: 10 µl of a 5× stock solution of QIAGEN OneStep RT-PCR Buffer, 2 µl of a dNTPs mix at a concentration of 10 mM, 3 µl of primer mix at a concentration of 10 µM and 2 µl of QIAGEN OneStep RT-PCR Enzyme Mix. The final mixture was then placed in a PCR tube, and cycled in a PCR-themocycler (BioRad iCycler version 4.006. Bio-Rad Laboratories AG, Reinach, Switzerland) using the following settings:

30 min at 50° C.
15 min at 95° C.
40 cycles: 30 sec at 94° C.
30 sec at 55° C.
1 min at 72° C.
10 min at 72° C.
Hold at 4° C.

pDrive Cloning

PCR products were run onto 2% agarose gels. Following DNA electrophoresis, the fragments of interest (~450 bp)

were excised from the agarose gels, and further extracted using the Macherey-Nagel NucloSpin Extract II kit 250 (Macherey-Nagel, Oensingen, Switzerland). For DNA sequencing, the extracted PCR products were cloned into the rescue-vector described above (pDrive vector, QIAGEN AG, Hombrechtikon, Switzerland) and transformed into the *E. coli* TOP10 strain (Invitrogen AG, Basel, Switzerland).

Miniprep Extraction

Positive colonies were cultured overnight at 37° C. (shaking 250 RPM) in 1.5 ml of Luria Bertani (LB) medium supplemented with 100 µg/ml ampicillin seeded in Macherey-Nagel Square-well Block plates (Macherey-Nagel, Oensingen, Switzerland). The next day DNA miniprep extractions were performed using the NucleoSpin Multi-8 Plasmid kit (Macherey-Nagel, Oensingen, Switzerland).

Sequencing and Sequence Analysis

Samples were sent for DNA sequencing to the DNA sequencing service company Fasteris (Plan-les-Ouates, Switzerland). The standard primers: M13rev, M13fwd, T7, SP6 were used (Table 5). To analyse the DNA sequences, the Clone Manager 9 Professional Edition (Scientific & Educational Software, NC, USA) and the BioEdit Sequence Alignment Editor (Hall T A (1999) Nucl Acids Symp Ser 41: 95-98) were used.

Cloning of Expression Vector for Recombinant Chimeric Antibody Expression

For recombinant expression in mammalian cells, the isolated murine VH and VL fragments were formatted as chimeric immunoglobulins using assembly-based PCR methods. These chimeric antibodies consist of a heavy chain where the murine heavy chain variable domain is fused to the human IgG1 heavy chain constant domains (γ1, hinge, γ2, and γ3 regions) and a light chain where the murine light chain variable domain is fused to a human kappa constant domain (Cκ). PCR-assembled murine variable and human constant parts were subsequently cloned into a modified mammalian expression vector based on the modified pcDNA3.1(−) vector from Invitrogen mentioned in Example 1 with the difference that a human immunoglobulin light chain kappa leader peptide was employed to drive protein secretion. For protein production of the immunoglobulin candidates, equal quantities of heavy and light chain vector DNA were co-transfected into suspension-adapted HEK-293 (ATCC number CRL-1573). The cell culture supernatant was collected after five days and purified using a Protein A affinity purification column (HiTrap Protein A sepharose column) operated on an ÄKTA FPLC system (both from GE Healthcare Europe GmbH, Glattbrugg, Switzerland).

TABLE 1 primer Mix VH-back

| 1 | GTG ATC GCC ATG GCG TCG ACC GAK GTR MAG CTT CAG GAG TC | SEQ ID NO: 65 |
| --- | --- | --- |
| 2 | GTG ATC GCC ATG GCG TCG ACC GAG GTB CAG CTB CAG CAG TC | SEQ ID NO: 66 |
| 3 | GTG ATC GCC ATG GCG TCG ACC CAG GTG CAG CTG AAG SAR TC | SEQ ID NO: 67 |
| 4 | GTG ATC GCC ATG GCG TCG ACC GAG GTC CAR CTG CAA CAR TC | SEQ ID NO: 68 |
| 5 | GTG ATC GCC ATG GCG TCG ACC CAG GTY CAG CTB CAG CAR TC | SEQ ID NO: 69 |
| 6 | GTG ATC GCC ATG GCG TCG ACC CAG GTY CAR CTG CAG CAR TC | SEQ ID NO: 70 |

TABLE 1-continued primer Mix VH-back

| 7 | GTG ATC GCC ATG GCG TCG ACC CAG GTC CAC GTG AAG CAR TC | SEQ ID NO: 71 |
| --- | --- | --- |
| 8 | GTG ATC GCC ATG GCG TCG ACC GAG GTG AAS STG GTG GAR TC | SEQ ID NO: 72 |
| 9 | GTG ATC GCC ATG GCG TCG ACC GAV GTG AWG STG GTG GAG TC | SEQ ID NO: 73 |
| 10 | GTG ATC GCC ATG GCG TCG ACC GAG GTG CAG STG GTG GAR TC | SEQ ID NO: 74 |
| 11 | GTG ATC GCC ATG GCG TCG ACC GAK GTG CAM CTG GTG GAR TC | SEQ ID NO: 75 |
| 12 | GTG ATC GCC ATG GCG TCG ACC GAG GTG AAG CTG ATG GAR TC | SEQ ID NO: 76 |
| 13 | GTG ATC GCC ATG GCG TCG ACC GAG GTG CAR CTT GTT GAR TC | SEQ ID NO: 77 |
| 14 | GTG ATC GCC ATG GCG TCG ACC GAR GTR AAG CTT CTC GAR TC | SEQ ID NO: 78 |
| 15 | GTG ATC GCC ATG GCG TCG ACC GAA GTG AAR STT GAG GAR TC | SEQ ID NO: 79 |
| 16 | GTG ATC GCC ATG GCG TCG ACC CAG GTT ACT CTR AAA SAR TC | SEQ ID NO: 80 |
| 17 | GTG ATC GCC ATG GCG TCG ACC CAG GTC CAA CTV CAG CAR CC | SEQ ID NO: 81 |
| 18 | GTG ATC GCC ATG GCG TCG ACC GAT GTG AAC TTG GAA SAR TC | SEQ ID NO: 82 |
| 19 | GTG ATC GCC ATG GCG TCG ACC GAG GTG AAG GTC ATC GAR TC | SEQ ID NO: 83 |

TABLE 2 primer Mix VH-forward

| 1 | CCTCCACCACTCGAGCC CGA GGA AAC GGT GAC CGT GGT | SEQ ID NO: 84 |
| --- | --- | --- |
| 2 | CCTCCACCACTCGAGCC CGA GGA GAC TGT GAG AGT GGT | SEQ ID NO: 85 |
| 3 | CCTCCACCACTCGAGCC CGC AGA GAC AGT GAC CAG AGT | SEQ ID NO: 86 |
| 4 | CCTCCACCACTCGAGCC CGA GGA GAC GGT GAC TGA GGT | SEQ ID NO: 87 |

TABLE 3 primer Mix VL-back

| 1 | GGCGGTGGC GCT AGC GAY ATC CAG CTG ACT CAG CC | SEQ ID NO: 88 |
| --- | --- | --- |
| 2 | GGCGGTGGC GCT AGC CAA ATT GTT CTC ACC CAG TC | SEQ ID NO: 89 |
| 3 | GGCGGTGGCGCT AGC GAY ATT GTG MTM ACT CAG TC | SEQ ID NO: 90 |
| 4 | GGCGGTGGC GCT AGC GAY ATT GTG YTR ACA CAG TC | SEQ ID NO: 91 |
| 5 | GGCGGTGGC GCT AGC GAY ATT GTR ATG ACM CAG TC | SEQ ID NO: 92 |

TABLE 3-continued primer Mix VL-back

| | | |
|---|---|---|
| 6 | GGCGGTGGC GCT AGC GAY ATT MAG ATR AMC CAG TC | SEQ ID NO: 93 |
| 7 | GGCGGTGGC GCT AGC GAY ATT CAG ATG AYD CAG TC | SEQ ID NO: 94 |
| 8 | GGCGGTGGCGCT AGC GAY ATY CAG ATG ACA CAG AC | SEQ ID NO: 95 |
| 9 | GGCGGTGGC GCT AGC GAY ATT GTT CTC AWC CAG TC | SEQ ID NO: 96 |
| 10 | GGCGGTGGCGCT AGC GAY ATT GWG CTS ACC CAA TC | SEQ ID NO: 97 |
| 11 | GGCGGTGGC GCT AGC GAY ATT STR ATG ACC CAR TC | SEQ ID NO: 98 |
| 12 | GGCGGTGGC GCT AGC GAY RTT KTG ATG ACC CAR AC | SEQ ID NO: 99 |
| 13 | GGCGGTGGCGCT AGC GAY ATT GTG ATG ACB CAG KC | SEQ ID NO: 100 |
| 14 | GGCGGTGGC GCT AGC GAY ATT GTG ATA ACY CAG GA | SEQ ID NO: 101 |
| 15 | GGCGGTGGC GCT AGC GAY ATT GTG ATG ACC CAG WT | SEQ ID NO: 102 |
| 16 | GGCGGTGGC GCT AGC GAY ATT GTG ATG ACA CAA CC | SEQ ID NO: 103 |
| 17 | GGCGGTGGCGCT AGC GAY ATT TTG CTG ACT CAG TC | SEQ ID NO: 104 |
| 18 | GGCGGTGGC GCT AGC GAA ACA ACT GTG ACC CAG TC | SEQ ID NO: 105 |
| 19 | GGCGGTGGCGCT AGC GAA AAT GTK CTS ACC CAG TC | SEQ ID NO: 106 |
| 20 | GGCGGTGGCGCT AGC CAG GCT GTT GTG ACT CAG GAA TC | SEQ ID NO: 107 |

TABLE 4 primer Mix VL-forward

| | | |
|---|---|---|
| 1 | ATGCTGAC GC GGC CGC ACG TTT KAT TTC CAG CTT GG | SEQ ID NO: 108 |
| 2 | ATGCTGAC GC GGC CGC ACG TTT TAT TTC CAA CTT TG | SEQ ID NO: 109 |
| 3 | ATGCTGAC GC GGC CGC ACG TTT CAG CTC CAG CTT GG | SEQ ID NO: 110 |
| 4 | ATGCTGAC GC GGC CGC ACC TAG GAC AGT CAG TTT GG | SEQ ID NO: 111 |

TABLE 5 sequencing primers

| | | |
|---|---|---|
| M13-Fwd | GTAAAACGACGGCCAGT | SEQ ID NO: 112 |
| M13-Rev | AACAGCTATGACCATG | SEQ ID NO: 113 |
| T7 | TAATACGACTCACTATAGG | SEQ ID NO: 114 |
| SP6 | GATTTAGGTGACACTATAG | SEQ ID NO: 115 |

Example 3

Biological Characterization of Anti-Human TL1A Antibodies

TL1A-specific Antibody Detection ELISA

Figure 1:
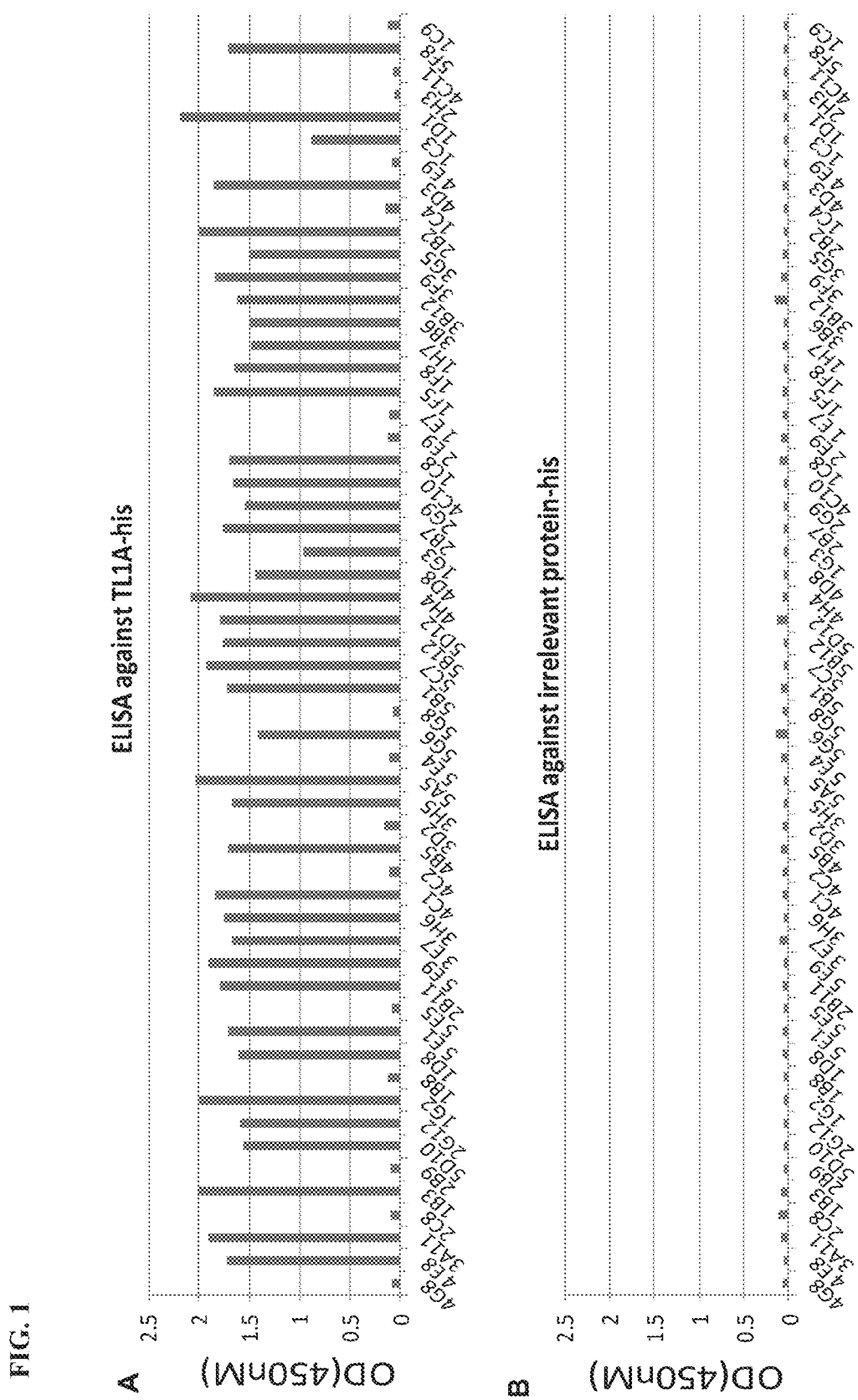
FIGS. 1A and B: This figure shows the binding of hybridoma antibodies to human TL1A-his (FIG. 1A) or the irrelevant protein-his (FIG. 1B), detected using an HRP-labelled anti-mouse IgG secondary antibody and TMB substrate.

Antibody titers, specificity and production by hybridomas and recombinant antibody candidates were determined by a direct ELISA. Briefly, 96 well-microtiter plates (Costar USA, distributor VWR AG, Nyon, Switzerland) were coated with 100 µl of recombinant human TL1A-his at 2 µg/ml in PBS (see Example 1 for the generation of the TL1A-his protein). Plates were incubated overnight at 4° C. and were then blocked with PBS 2% BSA (Bovine Serum Albumin, PAA Laboratories, Pasching, Austria) at room temperature (RT) for one hour. The blocking solution was removed and the hybridoma supernatants or purified antibodies were added. The plates were incubated at RT for 30 minutes, then washed nine times with PBS 0.01% Tween-20 (Sigma-Aldrich Chemie GmbH, Buchs, Switzerland) and a Horseradish Peroxidase (HRP) labelled-Goat anti-mouse H+L-detection antibody (Sigma-Aldrich Chemie GmbH, Buchs, Switzerland) was added at a dilution of 1:1000. To detect recombinant chimeric antibodies (see Example 2) that possess a human Fc, a HRP-labelled rabbit anti human IgG antibody (Sigma-Aldrich Chemie GmbH, Buchs, Switzerland) at a dilution of 1:1000 was used as the detection antibody. Plates were incubated for 30 minutes at room temperature (RT), washed nine times with PBS 0.01% Tween-20 and the TMB substrate (Bio-rad Laboratories AG, Reinach, Switzerland) was added to the plates and the reaction stopped after two to six minutes by adding $H_2SO_4$. Absorbance was then read at 450 nm by a microplate reader (Biotek, USA; distributor. WITTEC AG, Littau, Switzerland). FIG. 1 shows that the parental hybridoma supernatants of various clones recognize the human TL1A-his coated protein and not irrelevant his-tagged protein.

TNFRSF25 Blocking ELISA

The recombinant human TNFRSF25 receptor protein (TNFRSF25) was generated as follows: the cDNA for human TNFRSF25 (clone name: IRCMp5012F0812D) was purchased from Source Biosystems (Nottingham, UK) and the extracellular portion (amino acids 25-199) of human TNFRSF25 (numbering according to the Uniprot Q93038 sequence) was amplified with flanking restriction sites. The resulting PCR product encompassing an N-terminal 8-His tag sequence was subsequently cloned into a modified version of the pcDNA3.1 vector from Invitrogen (Invitrogen AG, Basel, Switzerland) carrying a CMV promoter, a Bovine Growth Hormone poly-adenylation, and the murine VJ2C leader peptide to drive the secretion of the recombinant protein. For recombinant protein production, the recombinant vector was transfected into suspension-adapted HEK 293 cells (ATCC number CRL 1573) using jetPEI™ transfection reagent (Polyplus-transfection S.A., Strasbourg, France; Distributor: Brunschwig, Basel, Switzerland). Cell culture supernatant was collected after five days and purified using a Protein A affinity purification column (HiTrap Protein A sepharose column; GE Healthcare Europe GmbH, Glattbrugg, Switzerland) operated on an ÄKTA FPLC system (GE Healthcare Europe GmbH, Glattbrugg, Switzerland).

Figure 2:
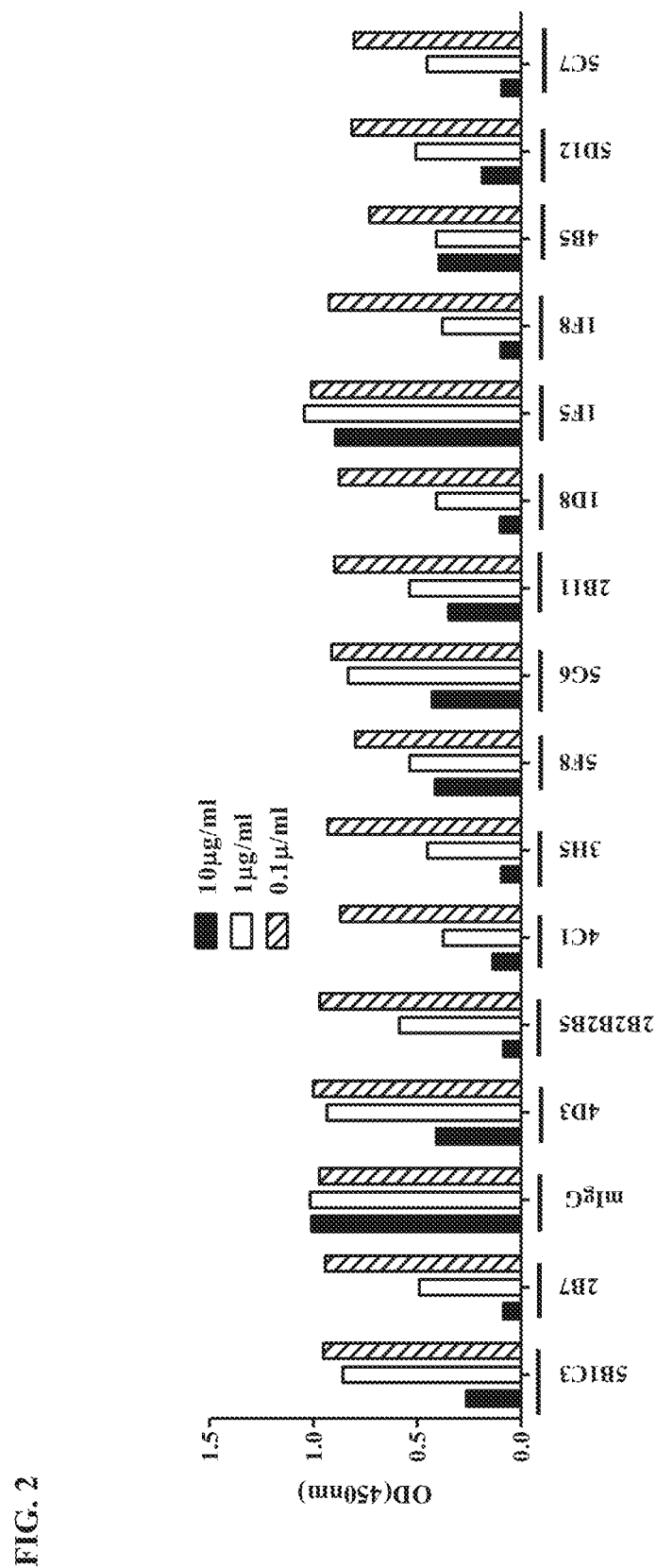
FIG. 2: This figure shows the effect of purified hybridoma anti-TL1A antibodies at three different concentrations in a blocking ELISA, where the binding of human TNFRSF25 to TL1A was evaluated in the presence of the antibodies shown in FIG. 2. Absorbance was read at 450 nm. mIgG: mouse IgG isotype control.

In order to determine if the generated anti-TL1A antibodies can block the binding of TL1A to the TNFRSF25 receptor, a blocking ELISA was developed. Ninety-six well-microtiter plates (Costar, USA; distributor VWR AG, Nyon, Switzerland) were coated with 100 µl of recombinant human TL1A-Fc (see Example 1) at 2 µg/ml in PBS or recombinant untagged TL1A (R&D Systems, Minneapolis, USA). Plates were incubated overnight at 4° C. and were then blocked with PBS 2% BSA at RT for one hour. The blocking solution was removed and the hybridoma supernatants or purified antibodies were added to the plate. Five minutes later, 50 µl of recombinant human TNFRSF25-Fc-his (R&D Systems) at 4 µg/ml was added to each well. Plates were incubated at RT for 60 minutes, then washed nine times with PBS 0.01% Tween-20 and mouse anti-poly histidine-HRP (Sigma-Aldrich Chemie GmbH, Buchs, Switzerland) was added at a dilution of 1:2000. Plates were incubated for 30 minutes at RT, washed 9 times with PBS 0.01% Tween-20 and the TMB substrate (Bio-rad Laboratories AG, Reinach, Switzerland) was added to the plates and the reaction stopped after 6 minutes by adding $H_2SO_4$. Absorbance was then read at 450 nm by a microplate reader (Biotek, USA; distributor: WITTEC AG, Littau, Switzerland). FIG. 2 shows that the purified antibodies are able to block the interaction between TL1A and TNFRSF25 in a dose dependent manner.

Inhibition of TL1A-induced IFN-γ Secretion by Primed CD4 T Cells

CD4 T cells primed by IL-12 and IL-18 cytokines polarize toward a TH1 phenotype and secrete IFN-γ. TL1A has been shown to enhance IFN-γ production by primed CD4 T cells. We therefore tested if the chimeric 5G6 antibody could block this TL1A-dependent increase in IFN-γ production.

To purify human CD4 T cells from peripheral blood mononuclear cells (PMBC), filters containing human leukocytes were collected from the Blood Collection Centre from La Chaux-de-Fonds, Switzerland (Centre de Transfusion Sanguine et Laboratoire de Serologie, rue Sophie-Mairet 29, CH-2300). Cells were removed from the filters by back flushing with 60 mL of PBS containing 10 U/mL of liquemin (Drossapharm AG, Lucern, Switzerland). PBMCs were then purified with 50 mL Blood-Sep-Filter Tubes (distributor Brunschwig, Basel, Switzerland) following manufacturer's instructions. Cells were washed three times with phosphate buffered saline (PBS) and then used for CD4 purification using naïve CD4 T cell purification kit from Miltenyi (Gladbach, Germany) according to the manufacturer's instructions.

The 5G6 antibody was tested to determine whether it could inhibit the effect of naturally produced TL1A. IL-12 and IL-18 primed CD4 T cells were incubated with monocytes that had been pre-activated by immune complexes (IC), and the production of IFN-γ was measured. Monocytes were isolated from PBMCs (see above) using a monocyte isolation kit II from Miltenyi (Gladbach, Germany) according to the manufacturer's instructions. Monocyte IC stimulation was performed as follows: chrompure human IgG (Jackson ImmunoResearch Europe Ltd, Newmarket, UK) was coated on a 12-well cell-culture plate (TPP, Trasadingen, Switzerland) at 50 µg/mL for 2 hrs at room temperature in PBS. The plate was then washed with PBS and incubated with mouse anti-human IgG (Jackson ImmunoResearch) for 1 hr at room temperature. The coated plate was washed once with PBS before plating of the purified monocytes. IC-stimulated monocytes were harvested after 48-72 hrs incubation at 37° C. in a 5% $CO_2$ incubator.

For flow cytometry analysis, IC-stimulated monocytes were stained with an anti-TL1A-PE antibody (GeneTex, distributed by Lucerna Chem. AG, Lucerna, Switzerland) or a rabbit isotype control (BD Pharmingen, Allschwil, Switzerland) at 10 µg/mL in a V-bottom 96-well microtiter plate (TPP, Trasadingen, Switzerland) at 4° C. for 30 min. The dilution buffer (FACS buffer) was PBS supplemented with 2% fetal calf serum (FCS, Amimed distributed by Bioconcept. Allschwil, Switzerland) and 10% Versene (Gibco Life Technologies). After incubation, 100 µL of FACS buffer was added to each well and the plate was centrifuged at 300 g for 3 min. Supernatant was discarded and samples were resuspended in 100 µL of a PE-anti rabbit secondary antibody solution at 0.2 µg/mL in FACS buffer. Samples were incubated at 4° C. for 20 min. The plate was washed as described above and samples were resuspended in 300 µL of FACS buffer and immediately acquired on a FACSCyan flow cytometer (Beckman Coulter International S.A., Nyon, Switzerland). For soluble TL1A quantification, supernatant from IC-stimulated monocyte culture were harvested at different time points (20, 48 and 72 hours) and sTL1A was quantified using human TL1A development ELISA kit (Peprotech), according to the manufacturer's recommendations.

For the monocyte-T cell co-culture, IC stimulated monocytes ($10^4$) and CD4 purified T cells ($10^5$) were seeded in flat bottom-96 well plates (TPP) with IL-12 (Peprotech) at 8 ng/mL and IL-18 (MBL International, distributed by LabForce AG, Nunningen, Switzerland) at 200 ng/mL in a $CO_2$ incubator at 37° C. The supernatants of culture were harvested after 72 hrs and IFN-γ was quantified as described above.

Figure 3:
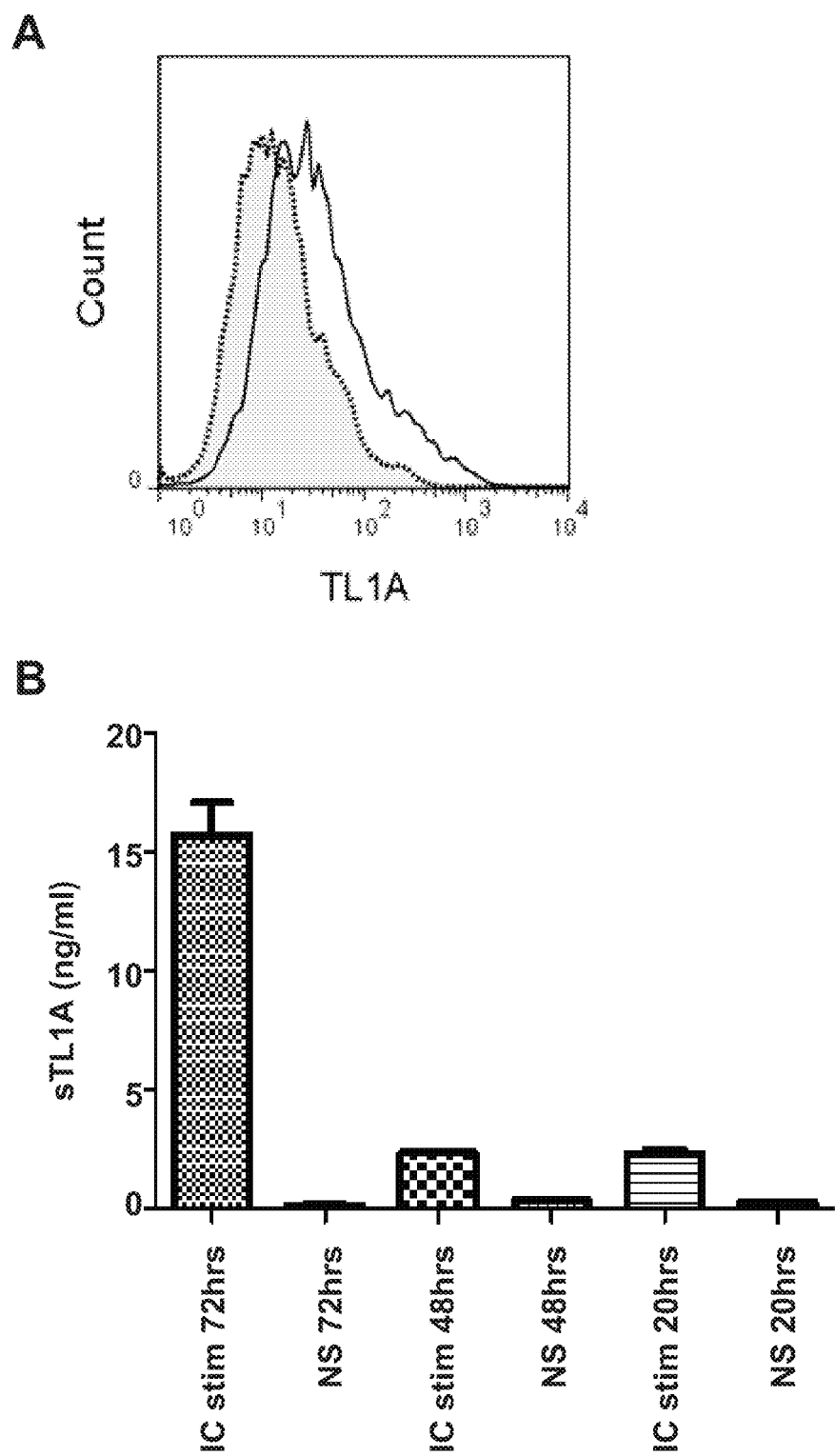
FIGS. 3A, B, and C: Parental 5G6 candidate blocks the effect of soluble and membrane bound TL1A produced by activated monocytes.
FIG. 3B: The supernatants of purified human monocytes from healthy donor PBMCs stimulated with immune complex were harvested and tested by ELISA for the presence of sTL1A proteins. The graph shows the interpolated TL1A concentration measured in the supernatants of indicated conditions. 'IC stim' means immune complex stimulated. 'NS' means not stimulated.
FIG. 3C: Naïve CD4 T cells purified from healthy donor PBMCs were incubated with IL-12, IL-18 and IC stimulated autologous monocytes. The parental chimeric 5G6 antibody was added at the concentrations indicated in the table at the same time as the monocytes. NA indicates that no IL-12 and IL-18 was added. The supernatants of cultures were quantified by ELISA. The graph shows the interpolated IFN-γ concentration for each indicated condition.
Figure 3:
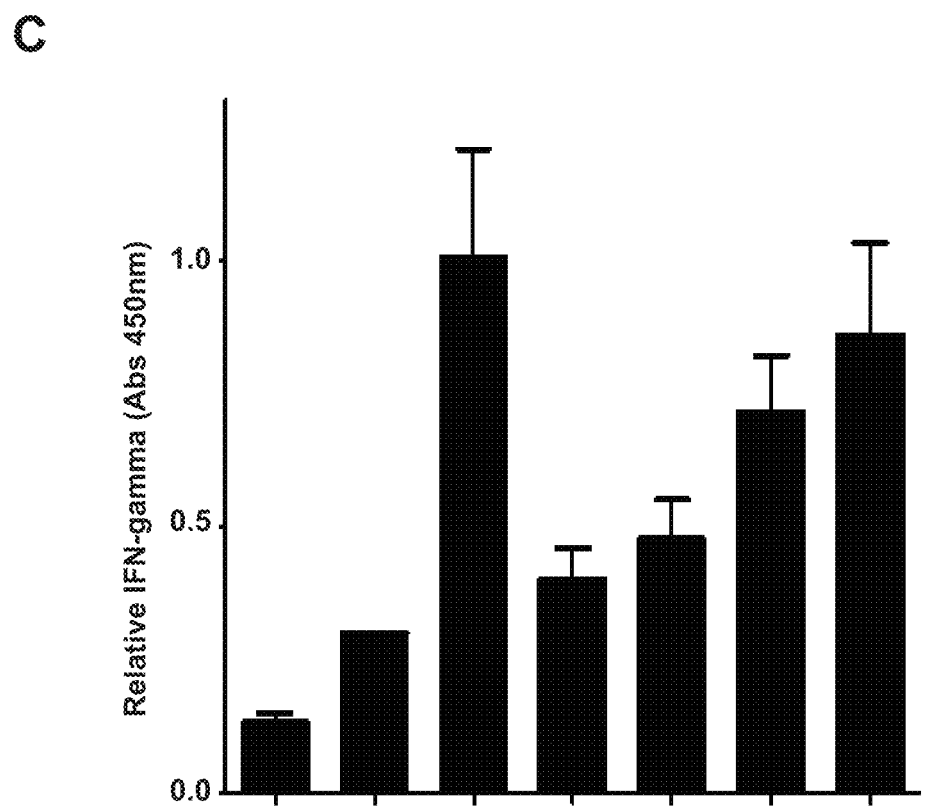

IC stimulated monocytes expressed TL1A on their membrane (mTL1A) (FIG. 3A) but more substantially as a soluble factor (sTL1A) (FIG. 3B) and induced a strong production of IFN-γ by co-cultured CD4 T cells (FIG. 3C). The 5G6 antibody suppressed completely the production of IFN-γ induced by the IC-stimulated monocytes showing a potent blocking of both mTL1A and sTL1A-mediated effect.

Example 4

Parental 5G6 Candidate Binds to Mouse, Rat, Cynomologus Monkey and Human TL1A

Figure 4:
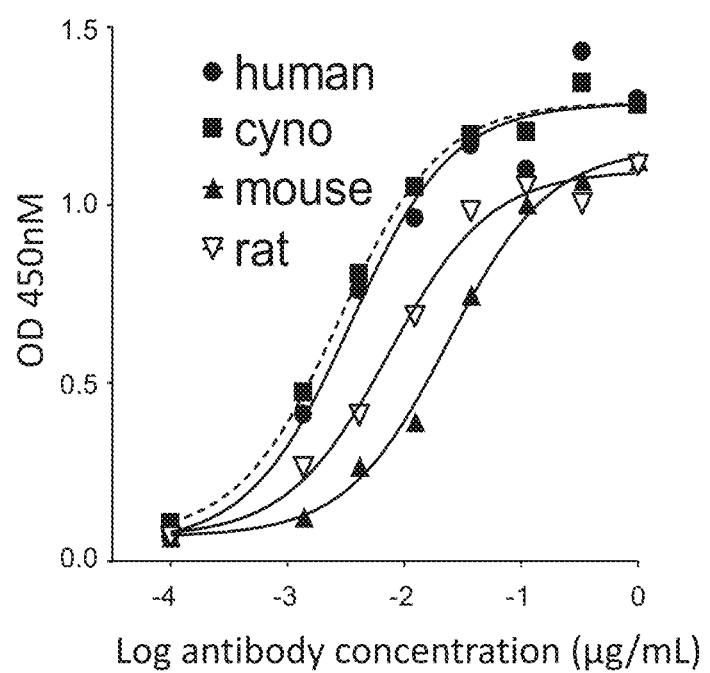
FIG. 4: Parental 5G6 candidate binds to mouse, rat, cynomologus monkey and human TL1A: The binding of 5G6 on the extracellular part of TL1A protein corresponding to human (*homo sapiens*), rat (*ratus norvegicus*), mouse (*mus musculus*) and cynomologus monkey (*macaca fascicularis*) sequences was determined by immunofluorescence. The graph shows the absorbance at 450 nm according to the log of the concentration of 5G6 used.

The reactivity of the parental 5G6 antibody (produced as a chimeric antibody with Human Fc) on the extracellular part of TL1A from diverse species was tested by ELISA. The extracellular part of TL1A protein corresponding to human (*homo sapiens*), rat (*ratus norvegicus*), mouse (*mus musculus*) and cynomologus monkey (*macaca fascicularis*) sequences (SEQ ID NOS: 38, 39, 40 and 41, respectively) was immobilized on high binding 96-well plates (Costar, USA; distributor VWR AG, Nyon, Switzerland) overnight at a concentration of 2 µg/mL at 4° C. in PBS. Plates were blocked with 2% BSA albumin (BSA, Sigma-Aldrich Chemie, Buchs, Switzerland) at RT for one hour. The blocking solution was removed and a dose dilution of 5G6 antibody was applied to the plates. Plates were incubated at RT for 60 minutes, washed six times with PBS 0.01% Tween-20 and the TMB substrate (Bio-rad Laboratories AG, Reinach, Switzerland) was added to the plates. The reaction was stopped after 6 minutes by adding $H_2SO_4$ and the binding of 5G6 on the different TL1A proteins was revealed using an HRP-labelled anti human IgG secondary antibody (Sigma-Aldrich Chemie, Buchs, Switzerland), added at a dilution of 1:1000. The plates were read for absorbance at 450 nm by a microplate reader (Biotek, USA; distributor: WITTEC AG, Littau, Switzerland). FIG. 4 shows that 5G6 recognized, in a dose dependent manner, the TL1A protein from all tested species.

Example 5

Humanization of Mouse Monoclonal Antibody 5G6

Humanizing the anti-human TL1A mouse antibody 5G6 including selection of human acceptor frameworks, back mutations, and mutations that substantially retain and/or improve the binding properties of human CDR-grafted acceptor frameworks is described herein.

Design of the Reshaped Variable Regions

Homology matching was used to choose human acceptor frameworks to graft 5G6 CDRs. Databases e.g. a database of germline variable genes from the immunoglobulin loci of human and mouse (the IMGT database, supra) or the VBASE2 (Retter I et al., (2005) Nucleic Acids Res. 33, Database issue D671-D674) or the Kabat database (Johnson G et al., (2000) Nucleic Acids Res. 28: 214-218) or publications (e.g., Kabat E A et al., supra) may be used to identify the human subfamilies to which the murine heavy and light chain V regions (SEQ ID NO: 1 and 2, respectively) belong and determine the best-fit human germline framework to use as the acceptor molecule. Selection of heavy and light chain variable sequences (VH and VL) within these subfamilies to be used as acceptor may be based upon sequence homology and/or a match of structure of the CDR1 and CDR2 regions to help preserve the appropriate relative presentation of the six CDRs after grafting.

For example, use of the IMGT database indicates good homology between the 5G6 heavy chain variable domain framework and the members of the human heavy chain variable domain subfamily 1. Highest homologies and identities of both CDRs and framework sequences were observed for germline sequences: IGHV1-2*02 (SEQ ID NO: 3), IGHV1-2*04 (SEQ ID NO: 4), IGHV1-2*05 (SEQ ID NO: 5), IGHV1-2*01 (SEQ ID NO: 6), and IGHV1-46*01 (SEQ ID NO: 7), all of which had sequence identity above 67% for the whole sequence up to CDR3. IGHV1-2*02 and IGHV1-2*04 showed 69.4% sequence identity while IGHV1-2*01 and IGHV1-46*01 showed a sequence identity of 68.4 and 67.3%, respectively.

Using the same approach, 5G6 light chain variable domain sequence showed good homology to the members of the human light chain variable domain kappa subfamily 1. Highest homologies and identities of both CDRs and framework sequences were observed for germline sequences: IGKV1-33*01 (SEQ ID NO: 8) and IGKV1D-33*01 (SEQ ID NO: 9) exhibited the highest identity (both having 80.0% identity), closely followed by another group consisting of IGKV1D-12*02 (SEQ ID NO: 10), IGKV1D-12*01 (SEQ ID NO: 11), and IGKV1-12*02 (SEQ ID NO: 12) all exhibiting the same degree of sequence identity (75.8%).

As starting point to the humanization process, human IGHV1-2*01 (SEQ ID NO: 3), and IGKV1-33*01 (SEQ ID NO: 8) variable domains were selected as acceptors to the 5G6 CDRs. A first humanized antibody of human gamma one isotype was prepared (see below). The antibody encompassed a human-mouse hybrid heavy chain variable domain and a human-mouse hybrid light chain variable domain. The hybrid heavy chain variable domain was based on the human heavy chain variable domain IGHV1-2*01 wherein germline CDR1 and 2 where respectively replaced for 5G6 heavy chain CDR1 and 2. Best matching JH segment sequence to the human acceptor framework was identified from the IMGT searches mentioned above. The resulting human-mouse hybrid heavy chain variable sequence having human IGHV1-2*01 framework regions, 5G6 mouse CDRs, and best matching JH to human acceptor is refereed herein as heavy chain variable domain VH1 with SEQ ID NO: 13. Similarly, the human-mouse hybrid light chain variable domain used for this first humanized antibody candidate had human IGKV1-33*01 framework regions, 5G6 mouse CDRs, and best matching JK to human acceptor, and is refereed herein as light chain variable domain VL1 with SEQ ID NO: 14. The first humanized antibody encompassing VH1 and VL1 is abbreviated herein VH1/VL1 antibody.

Production of the First Humanized Antibody Prototype

Coding DNA sequences (cDNAs) for VH1 and VL1 were synthesized in a scFv format by GENEART AG (Regensburg, Germany) thereby allowing for a single cDNA sequence to encompass both variable domains (SEQ ID NO: 15). Individual variable domain cDNAs were retrieved from this scFv construct by PCR, and further assembled upstream of their respective constant domain cDNA sequence(s) using PCR assembly techniques. Finally, the complete heavy and light chain cDNAs were ligated in independent vectors that are based on a modified pcDNA3.1 vector (Invitrogen, CA, USA) carrying the CMV promoter and a Bovine Growth Hormone poly-adenylation signal. The light chain specific vector allowed expression of human kappa isotype light chains by ligation of the light chain variable domain cDNA of interest in front of the kappa light chain constant domain cDNA using BamHI and BsiWI restriction enzyme sites; while the heavy chain specific vector was engineered to allow ligation of the heavy chain variable domain cDNA of interest in front of the cDNA sequence encoding the human IGHG1 CH1, IGHG1 hinge region, IGHG1 CH2, and IGHG1 CH3 constant domains using BamHI and SalI restriction enzyme sites. In both heavy and light chain expression vectors, secretion was driven by the mouse VJ2C leader peptide containing the BamHI site. The BsiWI restriction enzyme site is located in the kappa constant domain; whereas the SalI restriction enzyme site is found in the IGHG1 CH1 domain.

The VH1/VL1 antibody (having heavy chain SEQ ID NO: 16 and light chain SEQ ID NO: 17) was transiently produced by co-transfecting equal quantities of heavy and light chains vectors into suspension-adapted HEK293-EBNA1 cells (ATCC® catalogue number: CRL-10852) using polyethylenimine (PEI, Sigma, Buchs, Switzerland). Typically, 100 ml of cells in suspension at a density of 0.8-1.2 million cells per ml is transfected with a DNA-PEI mixture containing 50 µg of expression vector encoding the heavy chain and 50 µg of expression vector encoding the light chain. When recombinant expression vectors encoding antibody genes are introduced into the host cells, antibodies are produced by further culturing the cells for a period of 4 to 5 days to allow for secretion into the culture medium (EX-CELL 293, HEK293-serum-free medium; Sigma, Buchs, Switzerland), supplemented with 0.1% pluronic acid, 4 mM glutamine, and 0.25 µg/ml geneticin).

The VH1/VL1 antibody was purified from cell-free supernatant using recombinant protein-A streamline media (GE Healthcare Europe GmbH, Glattbrugg, Switzerland), and buffered exchanged into phosphate buffer saline prior to assays.

Kinetic Binding Affinity Constants by Surface Plasmon Resonance (SPR)

Kinetic binding affinity constants (KD) were measured on protein-A captured antibody using recombinant histidine tagged TL1A as analyte. Measurements were conducted on a BIAcore 2000 (GE Healthcare—BIAcore, GE Healthcare Europe GmbH, Glattbrugg, Switzerland) at room temperature, and analyzed with the BiaEvaluation software (BIAcore; v4.1. GE Healthcare Europe GmbH).

A CM5 research grade sensor chip (GE Healthcare Europe GmbH; ref. BR-1000-14) was activated by injecting 35 µl of a 1:1 N-hydroxysulfosuccinimide (NHS)/1-Ethyl-3-[3-dimethylaminopropyl]carbodiimide Hydrochloride (EDC) solution (v/v; 5 µl min flow-rate; on flow paths 1 and 2). Protein-A (ref. P7837; Sigma-Aldrich Chemie GmbH, Buchs, Switzerland) was diluted to a final concentration of 50 µg/ml in acetate buffer pH 4.5 (GE Healthcare Europe GmbH, BR-1003-50: one pH unit below pI) and subsequently immobilized on the previously activated CM5 sensor chip by injecting 35 μl on both flow path 1 and 2 (5 μl/min); this corresponded to approximately 1500 response units (RUs). The protein-A-CM5 sensor chip was then deactivated by injecting 35 μl of ethanolamine solution (5 μl/min). Finally, two injections of 10 μl of glycine solution (GE Healthcare Europe GmbH, ref. BR-1003-54; 10 mM: pH 1.5) were performed to release non-crosslinked protein-A molecules.

For affinity measurements, the chimeric and humanized antibody stored in 1× PBS buffer were diluted in HBS-EP buffer (GE Healthcare Europe GmbH, ref. BR-1001-88; 0.01 M HEPES, 0.15 M NaCl, EDTA 3 mM, 0.005% Surfactant P20, pH 7.4) and subsequently injected on the flow-path 2 of the protein-A CM5 chip (30 μl/min) to reach about 180 RUs. Following this capture step, the recombinant histidine tagged human TL1A was injected at different concentrations (1.25 to 125 nM) on the flow-path 1 and 2 (flow-path 1 being used as reference) at a 30 μl/min flow rate. After each binding event, surface was regenerated with glycine buffer pH 1.5 injected for 20 sec (30 μL/min).

Measurements (sensorgram: fc2-fc1) were best fitted with a 1:1 analyte model without mass transfer. To account for the experimental variations in protein-A captured antibody at the beginning of each measurement, the Rmax value was set to local in all fits. Dissociation times were of at least 300-600 seconds. Measurements were performed in duplicate and included zero-concentration samples for referencing. The Chi2 value represents the sum of squared differences between the experimental data and reference data at each point; while the plots of residuals indicate the difference between the experimental and reference data for each point in the fit. Both Chi2 and residual values were used to evaluate the quality of a fit between the experimental data and individual binding models.

Back Mutations of Grafted Human Frameworks

Since straight grafting of CDRs from 5G6 mouse antibody led to a candidate having no binding to human TL1A (Table 6), mutagenesis wherein human residues are substituted for mouse residues was initiated. This process is called back-mutation and is the most unpredictable procedure in the humanization of monoclonal antibodies. It necessitates the identification and the selection of critical framework residues from the mouse antibody that need to be retained in order to preserve affinity while at the same time minimizing potential immunogenicity in the humanized antibody.

To identify residues that may impact the most CDR conformation and/or inter-variable domain packing, a 3D model for the VH1-VL1 pair of variable domains was calculated using the structure homology-modelling server SWISS-MODEL (Arnold K et al., (2006) Bioinformatics, 22(2): 195-201) set in automated mode. Model analysis allowed the selection of a subset of positions based on their putative influence on CDR regions and/or heavy chain-light chain variable domain packing. This subset of positions consisted of variable heavy chain positions: 37, 48, 50, 67, 69, 71 and 75 as well as variable light chain positions: 5 and 34 (Kabat numbering).

Further humanized candidates having back mutations at the selected positions mentioned above were prepared using gene synthesis and standard mutagenesis methods. A single cDNA sequence encompassing both VH2 and VL2 variable domains (SEQ ID NO: 18) was synthesised and used as a starting point for further mutagenesis. Antibody expression and purification followed the methods described above. Humanized antibody candidates were assayed for their binding affinity by SPR as previously described.

Binding properties (KD) of selected humanized antibodies based on these single or combination of substitutions are shown in Table 6. Amongst humanized variants, VH3/VL1 antibody had the highest affinity for TL1A antigen, exhibiting a lower KD than the 5G6 chimeric antibody.

Thermostability of Selected Humanized Anti-TL1A Antibodies by Differential Scanning Calorimetry The thermal stabilities of the humanized antibodies were measured using differential scanning calorimetry (DSC). Monoclonal antibodies melting profiles are characteristic of their isotypes (Garber E & Demarest S J, (2007) Biochem. Biophys. Res. Commun. 355: 751-7), however the mid-point melting temperature of the FAB fragment can be easily identified even in the context of a full-length IgG. Such mid-point melting of FAB portion was used to monitor monoclonal stability of the humanized candidates.

Calorimetric measurements were carried out on a VP-DSC differential scanning microcalorimeter (GE Healthcare Europe GmbH). The cell volume was 0.128 ml, the heating rate was 200° C./h, and the excess pressure was kept at 65 p.s.i. All antibodies were used at a concentration of 1 mg/ml in PBS (pH 7.4). The molar heat capacity of antibody was estimated by comparison with duplicate samples containing identical buffer from which the antibody had been omitted. The partial molar heat capacities and melting curves were analyzed using standard procedures. Thermograms were baseline corrected and concentration normalized before being further analyzed using a Non-Two State model in the software Origin v7.0.

Humanized variant VH5/VL1 FAB fragment displayed a single transition at 83.8° C. with a shape and amplitude consistent with a cooperative unfolding which is generally observed for a compactly folded FAB fragments indicating that the engineering process was successful at retaining FAB stability. Overall the humanized variant showed a good thermal stability.

TABLE 6 humanized anti human TL1A antibodies

| Antibody variant (IGHG1) | SEQ ID NOs | Back-mutations VH/VL | $K_D$ (pM) |
|---|---|---|---|
| Chimera | 19, 20 | N.A./N.A. | 728 |
| VH1/VL1 | 16, 17 | N.A./N.A. | no binding |
| VH2/VL2 | 21, 25 | VH: V37A-M48I-W50E-V67A-M69L-R71V-I75S VL: N34S-T5N | 857 |
| VH3/VL1 | 22, 17 | VH: V37A-M48I-W50E-V67A-R71V | 249 |
| VH4/VL1 | 23, 17 | VH: V37A-M48I-W50E-R71V | 681 |
| VH5/VL1 | 24, 17 | VH: V37A-W50E-R71V | 259 |

Example 6

5G6 Humanized Candidates can Block TL1A-Induced IFN-γ Secretion by Primed CD4 T Cells Humanized candidates of the 5G6 antibody were tested to determine whether they could inhibit the TL1A-dependent increase in IFN-γ production.

Human CD4 T cells were purified from peripheral blood mononuclear cells (PMBC) as described in Example 3 above. All cell cultures were performed in Roswell Park Memorial Institute medium (RPMI-1640, PAA Laboratories, Pasching, Austria) supplemented with 10% heat inactivated foetal calf serum (FCS, Amimed distributed by Bioconcept, Allschwil, Switzerland), non essential amino acids (PAA, distributed by Chemie Brunschwig AG, Basel, Switzerland), ultraglutamine (Lonza, Basel, Switzerland), sodium pyruvate (PAA) and penicillin/streptomycin mix (Gibco Life technologies). CD4 purified T cells ($10^5$ cells/well) were incubated with IL-12

Figure 5:
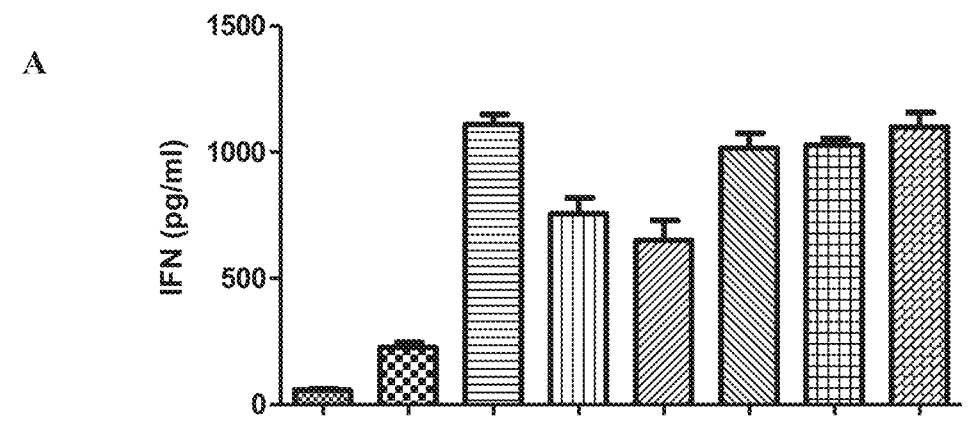
FIGS. 5A, B, C, and D: Humanized 5G6 antibodies block TL1A-induced IFN-γ secretion by primed CD4 T cells: Naïve CD4 T cells were incubated with IL-12, IL-18 and recombinant soluble human TL1A and the humanized 5G6 candidates (VH3/VL1, VH4/VL1, VH5/VL1 and VH2/VL2) were added at the concentrations indicated in the table. NA indicates that no L-12 and IL-18 was added. The culture supernatants were quantified by ELISA for concentration of IFN-γ. Graphs 5A-5D shows the IFN-γ concentration for each culture condition. Each graph displays the result of one humanized 5G6 candidate.
Figure 5:
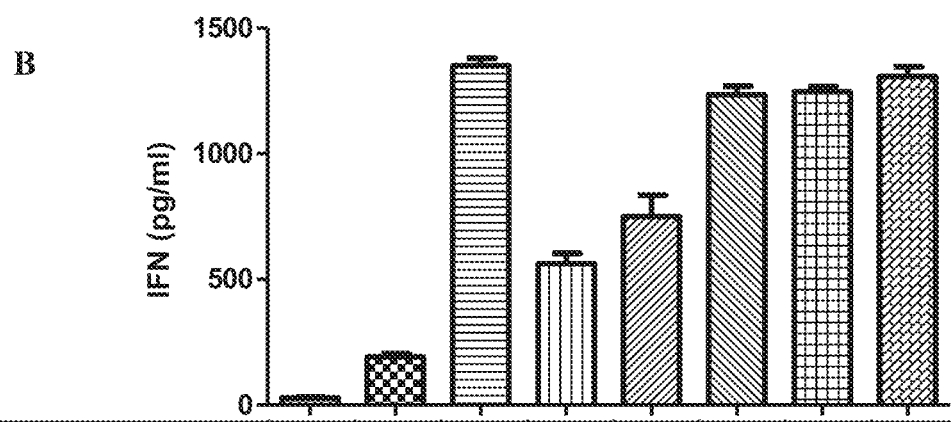
Figure 5:
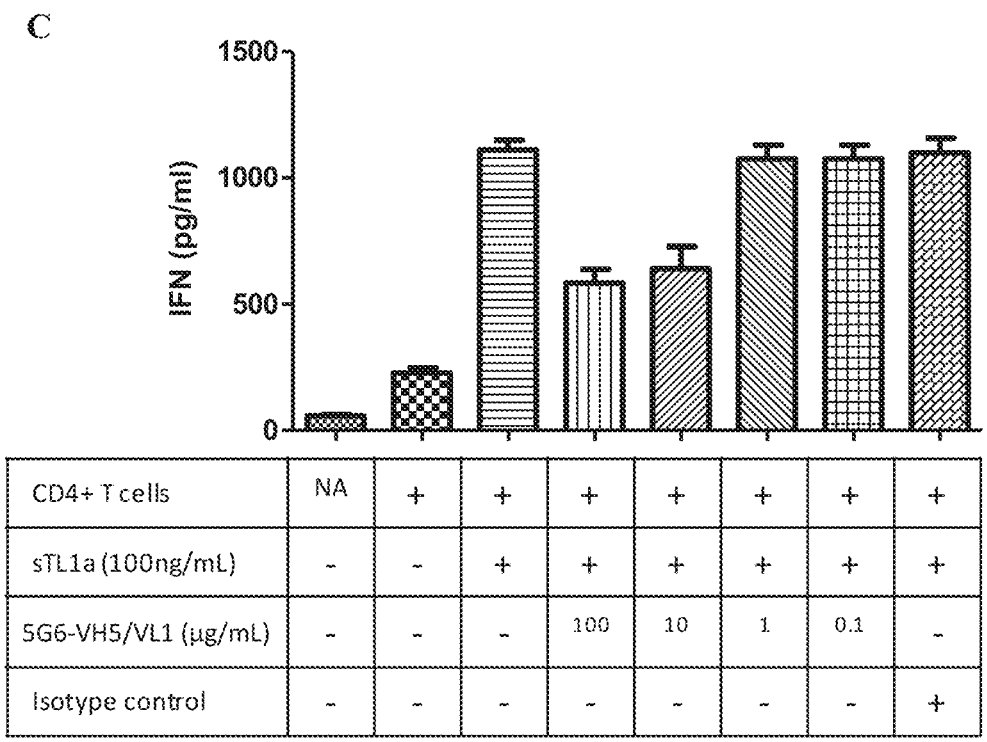
Figure 5:
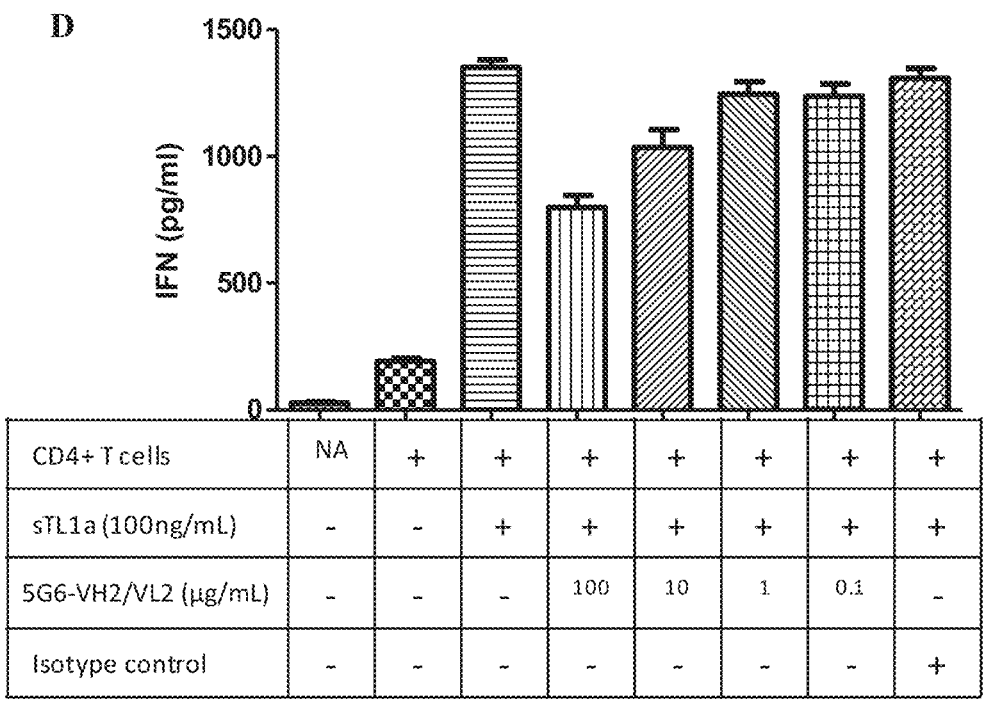

(Peprotech, Hamburg Germany) at 8 ng/mL. IL-18 (MBL International, distributed by LabForce AG, Nunningen, Switzerland) at 200 ng/mL (priming factors) and human soluble TL1A with an N-terminal his-tag (encoded by SEQ ID NO: 118) for 72 hrs in presence of the blocking 5G6 humanized antibody candidates (VH3/VL1—SEQ ID NOS: 22 and 17, VH4/VL1—SEQ ID NOS: 23 and 17, VH5/VL1—SEQ ID NOS: 24 and 17 and VH2/VL2—SEQ ID NO: 21 and 25), added at the concentrations 100, 10, 1 and 0.1 µg/mL (see tables in FIG. 5), at the same time. The isotype control was added at 100 µg/mL in a flat bottom 96-well cell culture plate (TPP AG, Trasadingen, Switzerland). The supernatants were harvested after 72 hrs and IFN-γ was quantified by ELISA using OptEIA kit (BD Pharmingen, Allschwil, Switzerland) according to the manufacturer's instructions. FIG. 5 shows that humanized anti-TL1A antibodies were able to inhibit substantially the production of IFN-γ.

Example 7

5G6 Humanized Antibody is Effective in a Murine Model of Allergic Asthma

Asthma does not spontaneously develop in mice therefore to investigate this disease in mice an asthmatic-like reaction needs to be induced in the airways. A variety of acute allergen challenge models have been developed and in this example BALB/c mice were used as they develop a good T helper cell 2 (Th2)-biased immunological response (Boyce J A & Austin K F (2005) J Exp Med, 201: 1869-73). Ovalbumin, derived from chicken egg is an allergen that induces a robust, allergic pulmonary inflammation in mice and therefore is frequently used in murine models of allergic asthma (Kumar R K et al., (2008) Curr Drug Targets, 9: 485-94).

In this example, the following immunization protocol was used to induce allergic asthma: BALB/c mice were sensitized by i.p. injection of 100 g of ovalbumin (Albumin from chicken egg white, Grade V, Sigma Aldrich, Switzerland) adsorbed on 1 mg of a suspension of aluminium hydroxide and magnesium hydroxide (Imject Alum, Thermo Scientific, Switzerland) on day 0 and day 14. On day 28, 30 and 33, mice were treated i.p. with 50 mg/kg of humanized 5G6 antibody (VH5/VL1: format IgG4 hinge stabilised; SEQ ID NO: 124 and 17) or an equivalent amount of the control human IgG. As a positive control, dexamethasone (Sigma, Switzerland) was used at 5 mg/kg. Four hours following treatment, mice were anesthetized with 30 mg/kg of xylazine and 150 mg/kg of Ketamin (Xylazol and Ketasol from Graeub Veterinary products, Switzerland) and injected intranasally with 10 µg of ovalbumin. Three days later, mice were sacrificed and after cannulation of their trachea, bronchoalveolar lavage (BAL) was performed by injecting 2 ml of cold PBS into the lung. Cells in BAL fluids were counted and eosinophils detected by flow cytometry using CD11c and Siglec F cell surface markers.

Figure 6:
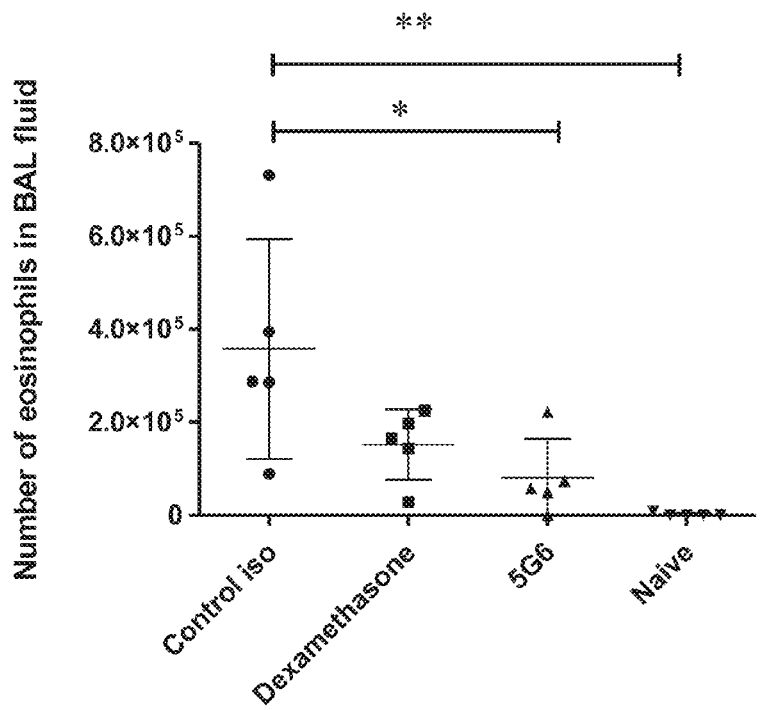
FIG. 6: Humanized 5G6 antibody reduced the number of cells in bronchoalveolar lavage (BAL) fluid in a murine model of allergic asthma. Mice were treated with the humanized 5G6 candidate (VH5/VL1; format IgG4 hinge stabilised) at 50 mg/kg or an equivalent amount of control human IgG, or dexamethasone at 5 mg/kg (positive control), on day 28, 30 and 33 following the induction of an immunological response induced by ovalbumin challenge. The graph shows the number of eosinophils in BAL fluid for each mouse and the average number of eosinophils for each group was calculated. Standard deviation was calculated using a one way ANOVA * indicates $p<0.05$, and** indicates $p<0.01$.

The results are shown in FIG. 6 where it can be observed that treatment with the humanized antibody 5G6 resulted in approximately a 4-fold reduction in the number of eosinophils in BAL fluid of asthmatic mice.

Example 8

5G6 Humanized Antibody is Effective in a Treating DSS-Induced Acute Colitis in Mice Many different animal models of inflammatory bowel disease (IBD) have been developed and these are valuable tools for investigating the involvement of various factors into the pathogenesis of IBD and to evaluate therapeutic options. The dextran sulphate sodium (DSS) induced colitis model is a widely used model of inflammatory bowel disease because of its simplicity and it has many similarities to human IBD, particularly ulcerative colitis (Perše M & Cerar A (2012) J Biomed Biotechnol, 2012; 718617; Wirtz S et al., (2007) Nat. Protoc, 2: 541-6).

Figure 7:
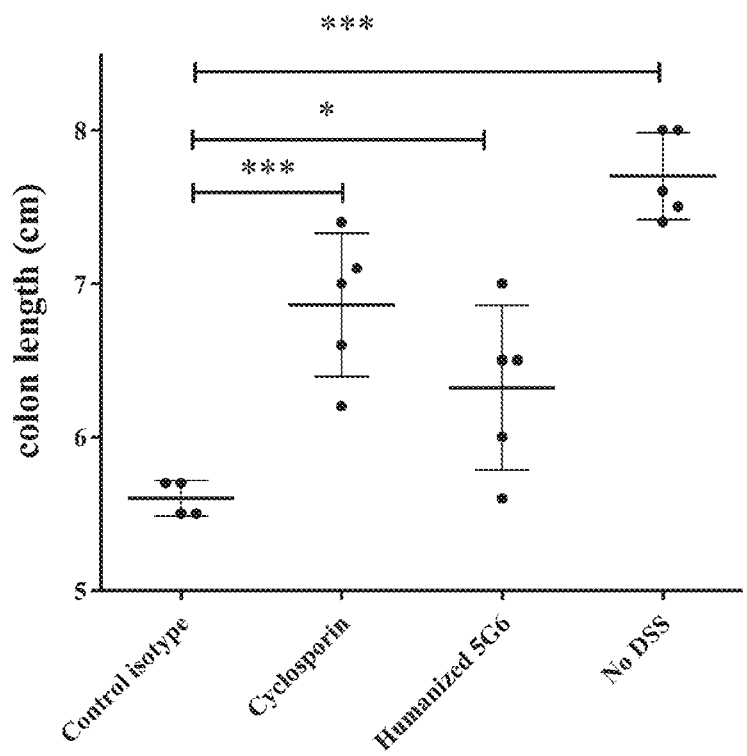
FIG. 7: Treatment by humanized 5G6 antibody ameliorates shortening of colon in a DSS-induced model of acute colitis. Mice were treated 3× week with 50 mg/kg of a humanized 5G6 antibody (VH5/VL1; format IgG4 hinge stabilised) or an equivalent amount of isotype control, or cyclosporine at 5 mg/kg (positive control). The graph shows the entire colon length for each mouse and the average length per group.

To evaluate the potential effect of humanized 5G6 antibody (VH5/VL1; format IgG4 hinge stabilised; SEQ ID NO: SEQ ID NO: 124 and 17) in IBD, a condition of acute colitis was induced in C57Bl/6 mice by administering 2% of DSS (MW 36-50 kDa; MP Biomedicals) in the drinking water of the test group for 5 days. The control group were given untreated tap water. Following DSS exposure, tap water was given to the test group of mice for 7 days. Mice were treated i.p 3×/week with 50 mg/kg of humanized 5G6 antibody or an equal amount of isotype control. As a positive control, cyclosporine (Sandimmune, Novartis Pharma, Switzerland) was used at 5 mg/kg. Mice were monitored daily for weight loss and stool consistency. At day 12, all mice were sacrificed and their entire colon lengths measured. As shown in FIG. 7, it can be observed that treatment of mice with humanized antibody 5G6 resulted in reduction of colon shortening induced by DSS.

Example 9

5G6 Humanized Antibody is Effective in a Treating TNBS Colitis in Rats

Intestinal inflammation in rats can be induced by intrarectal administration of trinitrobenzenesulfonic acid (TNBS). The resulting localised ulceration and inflammation is believed to involve a T-cell mediated response against hapten-modified autologous proteins or luminal antigens (Wirtz S et al. supra). Symptoms include diarrhoea, occult blood and weight loss.

To evaluate the potential effect of a humanized 5G6 antibody (VH5/VL1; format IgG4 hinge stabilised; SEQ ID NO: SEQ ID NO: 124 and 17) in IBD, a condition of colitis was induced in Sprague-Dawley rats by intrarectal administration of TNBS Solution (50% TNBS: 50% 200 proof ethanol; 16 mg/ml TNBS (Sigma, Cat#92822) at 64 mg/kg (4 ml/kg) into the colon of anaesthetised rats in the treatment groups. The control group received no TNBS Solution. Two hours after TNBS administration, rats were treated i.p with a single dose of humanized 5G6 antibody (50 mg/kg) or an equal amount of isotype control. As a positive control, prednisolone (Sigma) was administered orally at a dose of 10 mg/kg two hours after TNBS administration and daily for the following 5 days. Rats were sacrificed on day 7 and disease severity assessed as a colonic score using the following scoring system:
1) Adhesions: none=0, minimal=1, involving several bowel loops=2
2) Strictures: none=0, mild=2, severe, proximal dilatation=3
3) Ulcers: none=0, linear ulceration<1 cm=1, two linear ulcers<1 cm=2, more sites of ulceration or one large ulcer=3
4) Wall thickness: less than 1 mm=0, 1-3 mm=1, >3 mm=2

As shown in FIG. 8, it can be observed that treatment of rats with humanized antibody 5G6 resulted in reduction of disease parameters induced by TNBS.

Example 10

Binding of 5G6 Humanized Antibody to hTL1A is Blocked by Both hDcR3-Fc and hDR3-Fc As discussed above TL1A is a ligand for TNFRSF25/DR3 and the decoy receptor DcR3. DR3 is a death domain-containing receptor that is upregulated during T cell activation and the interaction of TL1A with DR3 can promote T cell expansion during an immune response (Migone T S et al., supra). The secreted decoy receptor (DcR3), a soluble protein of the tumor necrosis factor receptor (TNFR) superfamily, blocks the action of TL1A. (Kim S & Zhang L, supra).

To evaluate whether the 5G6 humanized antibody could interfere with the interaction of hTL1A to the receptor DR3 and/or to the decoy receptor DcR3, a his-tagged human TL1A was coated at 2 µg/ml on an ELISA plate and incubated with 20 µg/ml of 5G6 humanized antibody (VH5/VL1; format IgG4 hinge stabilised; SEQ ID NO: SEQ ID NO: 124 and 17) in the presence of 10 µg/ml of Fc fusions of the ectodomains of either human DcR3, DR3 (both R&D systems) or an irrelevant receptor (Ctrl-Fc) followed by detection with peroxidase-conjugated anti-human IgG (Fab specific). As can be observed in FIG. 9, binding of the 5G6 humanized antibody to hTL1A is blocked by both hDcR3-Fc and hDR3-Fc. This confirms that 5G6 humanized antibody binding to hTL1A inhibits the interaction of hTL1A with both DR3 and DcR

The invention claimed is:

1. An antibody or fragment thereof that binds to TL1A comprising a heavy chain CDR1 comprising the amino acid sequence of SEQ ID NO: 51, a heavy chain CDR2 comprising the amino acid sequence of SEQ ID NO: 52, and a heavy chain CDR3 comprising the amino acid sequence of SEQ ID NO: 53; and comprising a light chain CDR1 comprising the amino acid sequence of SEQ ID NO: 54, a light chain CDR2 comprising the amino acid sequence of SEQ ID NO: 55, and a light chain CDR3 comprising the amino acid sequence of SEQ ID NO: 56.

2. The antibody or fragment thereof of claim 1, wherein the antibody or fragment thereof is a murine antibody, chimeric antibody or a humanized antibody.

3. The antibody or fragment thereof of claim 1, wherein the antibody or fragment thereof is a humanized antibody.

4. The antibody or fragment thereof of claim 1, wherein the antibody or fragment thereof comprises a heavy chain variable region sequence comprising the amino acid sequence of SEQ ID NO: 1.

5. The antibody or fragment thereof of claim 1, wherein the antibody or fragment thereof comprises a non-CDR region of a heavy chain variable region sequence which is at least 80% identical to the non-CDR region of the heavy chain variable region sequence of SEQ ID NO: 1.

6. The antibody or fragment thereof of claim 1, wherein the antibody or fragment thereof comprises a heavy chain variable region sequence comprising an amino acid sequence selected from the group consisting of SEQ ID NOS: 26, 27, 28 and 29.

7. The antibody or fragment thereof of claim 1, wherein the antibody or fragment thereof comprises a non-CDR region of a heavy chain variable region sequence which is at least 80% identical to the non-CDR region of the heavy chain variable region sequence selected from the group consisting of SEQ ID NOS: 26, 27, 28 and 29.

8. The antibody or fragment thereof of claim 1, wherein the antibody or fragment thereof comprises a heavy chain variable region sequence comprising the amino acid sequence of SEQ ID NO: 29.

9. The antibody or fragment thereof of claim 1, wherein the antibody or fragment thereof comprises a non-CDR region of a heavy chain variable region sequence which is at least 80% identical to the non-CDR region of the heavy chain variable region sequence of SEQ ID NO: 29.

10. The antibody or fragment thereof of claim 1, wherein the antibody or fragment thereof comprises a heavy chain sequence comprising an amino acid sequence selected from the group consisting of SEQ ID NOS: 21, 22, 23 and 24.

11. The antibody or fragment thereof of claim 1, wherein the antibody or fragment thereof comprises a heavy chain sequence comprising a non-CDR region which is at least 80% identical to the non-CDR region of the heavy chain variable region sequence of a heavy chain sequence selected from the group consisting of SEQ ID NOS: 21, 22, 23 and 24.

12. The antibody or fragment thereof of claim 1, wherein the antibody or fragment thereof comprises a heavy chain variable framework region that is the product of a human gene selected from the group consisting of IGHV1-2*02 (SEQ ID NO: 3), IGHV1-2*04 (SEQ ID NO: 4), IGHV1-2*05 (SEQ ID NO: 5), IGHV1-2*01 (SEQ ID NO: 6), and IGHV1-46*01 (SEQ ID NO: 7).

13. The antibody or fragment thereof of claim 1, wherein the antibody or fragment thereof comprises a light chain variable region sequence comprising the amino acid sequence of SEQ ID NO: 2.

14. The antibody or fragment thereof of claim 1, wherein the antibody or fragment thereof comprises a non-CDR region of a light chain variable region sequence which is at least 80% identical to the non-CDR region of the light chain variable region sequence of SEQ ID NO: 8.

15. The antibody or fragment thereof of claim 1, wherein the antibody or fragment thereof comprises a light chain variable region sequence comprising the amino acid sequence selected from the group consisting of SEQ ID NOS: 14 and 30.

16. The antibody or fragment thereof of claim 1, wherein the antibody or fragment thereof comprises a non-CDR region of a light chain variable region sequence which is at least 80% identical to the non-CDR region of the light chain variable region sequence selected from the group consisting of SEQ ID NO: 14 and 30.

17. The antibody or fragment thereof of claim 1, wherein the antibody or fragment thereof comprises a light chain sequence comprising the amino acid sequence selected from the group consisting of SEQ ID NO: 17 and 25.

18. The antibody or fragment thereof of claim 1, wherein the light chain sequence comprises a non-CDR region which is at least 80% identical to the non-CDR region of the light chain variable region sequence of the light chain sequence selected from the group consisting of SEQ ID NO: 17 and 25.

19. The antibody or fragment thereof of claim 1, wherein the antibody or fragment thereof comprises a light chain variable framework region that is the product a human gene selected from the group consisting of IGKV1-33*01 (SEQ ID NO: 8), IGKV1D-33*01 (SEQ ID NO: 9), IGKV1D-12*02 (SEQ ID NO: 10), IGKV1D-12*01 (SEQ ID NO: 11) and IGKV1-12*02 (SEQ ID NO: 12).

20. The antibody or fragment thereof of claim 1, wherein the antibody or fragment thereof comprises:
   (a) a heavy chain sequence comprising the amino acid sequence of SEQ ID NO: 22 or SEQ ID NO: 24; and
   (b) a light chain sequence comprising the amino acid sequence of SEQ ID NO: 17.

21. The antibody or fragment thereof of claim 1, wherein the antibody or fragment thereof comprises:
   (a) a heavy chain variable region sequence comprising the amino acid sequence of SEQ ID NO: 27 or SEQ ID NO: 29; and
   (b) a light chain variable region sequence comprising the amino acid sequence of SEQ ID NO: 14.

22. The antibody or fragment thereof of claim 1, wherein at least one of the heavy chain CDRs and/or at least one of the light chain CDRs comprises at least one amino acid modification.

23. The antibody or fragment thereof of claim 1, further comprising heavy and/or light constant regions.

24. The antibody or fragment thereof of claim 23, wherein the human heavy constant region is selected from the group of human immunoglobulins consisting of IGHG1, non fucosylated IGHG1 and IGHG4.

25. The antibody or fragment thereof of claim 1, wherein the antibody has a non fucosylated IGHG1 Fc region.

26. The antibody or fragment thereof of claim 1, wherein the antibody comprises an isotypic variant comprising the CH1 from human IgG4 (IGHG4), the hinge from human IgG4 (IGHG4), having S228P substitution and the CH2 and CH3 from human IgG4 (IGHG4).

27. The antibody or fragment thereof of claim 1, wherein the antibody or fragment thereof binds to human TL1A.

28. The antibody or fragment thereof of claim 1, wherein the antibody or fragment thereof binds to human TL1A and is cross reactive with murine, rat and cynomologus TL1A.

29. The antibody or fragment thereof of claim 1, wherein the antibody or fragment thereof binds to hTL1A and inhibits the interaction of hTL1A with both DR3 and DcR3.

30. The antibody or fragment thereof of claim 1, wherein the antibody or fragment thereof is an antagonist antibody.

31. The antibody or fragment thereof of claim 1, wherein the antibody or fragment thereof is a neutralizing antibody.

32. The antibody or fragment thereof of claim 1, wherein the antibody is a monovalent antibody.

33. The antibody or fragment thereof of claim 1, wherein the antibody is a full length antibody.

34. The antibody or fragment thereof of claim 1, wherein the antibody is an antibody fragment selected from the group consisting of Fab, Fab', Fab'-SH, Fd, Fv, dAb, F(ab')2, scFv, bispecific single chain Fv dimers, diabodies, triabodies and scFv genetically fused to the same or a different antibody.

35. The antibody or fragment thereof of claim 1, wherein the antibody comprises a modified Fc region, wherein the antibody comprising the modified Fc region exhibits altered effector function compared to the unmodified Fc region.

36. The antibody or fragment thereof of claim 1, wherein the antibody or fragment thereof binds to human TL1A with an affinity ($K_D$) of 700 pM or less.

37. The antibody or fragment thereof of claim 1, wherein the antibody has a Fab fragment thermostability temperature greater than 80° C.

38. An isolated nucleic acid encoding an antibody of fragment thereof that binds to TL1A comprising a heavy chain CDR1 comprising the amino acid sequence of SEQ ID NO: 51, a heavy chain CDR2 comprising the amino acid sequence of SEQ ID NO: 52, and a heavy chain CDR3 comprising the amino acid sequence of SEQ ID NO: 53; and comprising a light chain CDR1 comprising the amino acid sequence of SEQ ID NO: 54, a light chain CDR2 comprising the amino acid sequence of SEQ ID NO: 55, and a light chain CDR3 comprising the amino acid sequence of SEQ ID NO: 56.

39. The isolated nucleic acid of claim 38 comprising DNA encoding the heavy chain variable region comprising the nucleic acid sequence of SEQ ID NO: 33 or 35; and/or DNA encoding the light chain variable region comprising the nucleic acid sequence of SEQ ID NO: 36.

40. A vector comprising the isolated nucleic acid of claim 39.

41. A host cell comprising the isolated nucleic acid of claim 38 or the vector of claim 40.

42. A method of producing an antibody or fragment thereof that binds to human TL1A comprising culturing the host cell of claim 41 so that the nucleic acid is expressed and the antibody produced.

43. A composition comprising the antibody or fragment thereof of claim 1 and a pharmaceutically acceptable carrier.

44. An immunoconjugate comprising the antibody or fragment thereof of claim 1 linked to a therapeutic agent.

45. A composition comprising the immunoconjugate of claim 44 and a pharmaceutically acceptable carrier.

46. The composition of claim 43 further comprising a second pharmaceutically active agent.

47. A method for treating a TL1A mediated disorder in a subject, the method comprising administering to the subject a therapeutically effective amount of the antibody or fragment thereof of claim 1.

48. The method of claim 47, wherein the TL1A mediated disorder is selected from the group consisting of inflammatory bowel disease (IBD) including ulcerative colitis and Crohn's disease, rheumatoid arthritis, MS, type 1 and type 2 diabetes, psoriasis, psoriatic arthritis, ankylosing spondylitis, atopic dermatitis; allergic reactions or conditions, asthma and allergic lung inflammation; cancers atherosclerosis, infections, graft rejection, graft versus host diseases (GVHD) and cardiovascular disorders/diseases, transplant rejection, central nervous system injury, psoriasis, leukaemia or lymphoma, chronic lymphocytic leukaemia (CLL), atherosclerosis, and lung and colon carcinomas, chronic obstructive pulmonary disease (COPD), optic neuritis, age related macular degeneration, systemic lupus erythematosus (SLE), Sjogren's syndrome, scleroderma, systemic sclerosis, chronic Kidney disease, liver fibrosis, tuberculosis, idiopathic pulmonary fibrosis, tuberculosis induced lung fibrosis, retroperitoneal Fibrosis, pulmonary fibrosis, cystic fibrosis, endomyocardial fibrosis, atrial fibrosis, mediastinal fibrosis, myelofibrosis, retroperitoneal fibrosis, progressive massive fibrosis, systemic fibrosis, and arthrofibrosis.

49. The method of claim 47, wherein the antibody has a non fucosylated IGHG1 Fc region and exhibits enhanced cytotoxicity as compared to the antibody having human heavy chain constant region IGHG1.

50. An article of manufacture comprising the antibody or fragment thereof of claim 1, for the treatment of a TL1A mediated disorder.

51. A kit comprising the antibody or fragment thereof of claim 1, for the treatment of a TL1A mediated disorder.

* * * * *

```
                            SEQUENCE LISTING

<160> NUMBER OF SEQ ID NOS: 124

<210> SEQ ID NO 1
     <211> LENGTH: 119
     <212> TYPE: PRT
     <213> ORGANISM: Mus musculus

<400> SEQUENCE: 1

Gln Val Gln Leu Gln Gln Pro Gly Ser Val Leu Val Arg Pro Gly Ala
     1               5                   10                  15

Ser Val Lys Val Ser Cys Lys Ala Ser Gly Tyr Thr Phe Thr Ser Ser
                 20                  25                  30

Trp Met His Trp Ala Lys Gln Arg Pro Gly Gln Gly Leu Glu Trp Ile
             35                  40                  45

Gly Glu Ile His Pro Asn Ser Gly Gly Thr Asn Tyr Asn Glu Lys Phe
         50                  55                  60

Lys Gly Lys Ala Thr Val Asp Thr Ser Ser Thr Ala Tyr Val Asp
     65                  70                  75                  80

Leu Ser Ser Leu Thr Ser Glu Asp Ser Ala Val Tyr Tyr Cys Ala Arg
                     85                  90                  95

Gly Asp Tyr Tyr Gly Tyr Val Ser Trp Phe Ala Tyr Trp Gly Gln Gly
                     100                 105                 110

Thr Leu Val Thr Val Ser Ser
             115

<210> SEQ ID NO 2
     <211> LENGTH: 107
     <212> TYPE: PRT
     <213> ORGANISM: Mus musculus

<400> SEQUENCE: 2

Asp Ile Gln Met Asn Gln Ser Pro Ser Ser Leu Ser Ala Ser Leu Gly
     1               5                   10                  15

Asp Thr Ile Thr Ile Thr Cys His Ala Ser Gln Asn Ile Asn Val Leu
                 20                  25                  30

Leu Ser Trp Tyr Gln Gln Lys Pro Gly Asn Ile Pro Lys Leu Leu Ile
             35                  40                  45

Tyr Lys Ala Ser Asn Leu His Thr Gly Val Pro Ser Arg Phe Ser Gly
         50                  55                  60

Ser Gly Ser Gly Thr Gly Phe Thr Phe Thr Ile Ser Ser Leu Gln Pro
     65                  70                  75                  80

Glu Asp Ile Ala Thr Tyr Tyr Cys Gln Gln Gly Gln Ser Tyr Pro Tyr
                     85                  90                  95

Thr Phe Gly Gly Gly Thr Lys Leu Glu Ile Lys
                     100                 105

<210> SEQ ID NO 3
     <211> LENGTH: 114
```

-continued

```
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Trp Phe Asp Ser Trp Gly Gln Gly Thr Leu Val Thr Val
            100                 105                 110

Ser Ser

<210> SEQ ID NO 4
<211> LENGTH: 114
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Trp Phe Asp Ser Trp Gly Gln Gly Thr Leu Val Thr Val
            100                 105                 110

Ser Ser

<210> SEQ ID NO 5
<211> LENGTH: 114
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60
```

```
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Val Val Tyr Tyr Cys
             85                  90                  95

Ala Arg Asn Trp Phe Asp Ser Trp Gly Gln Gly Thr Leu Val Thr Val
            100                 105                 110

Ser Ser

<210> SEQ ID NO 6
<211> LENGTH: 114
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
             35                  40                  45

Gly Arg Ile Asn Pro Asn Ser Gly Gly Thr Asn Tyr Ala Gln Lys Phe
 50                  55                  60

Gln Gly Arg Val Thr Ser Thr Arg Asp Thr Ser Ile Ser Thr Ala Tyr
 65                  70                  75                  80

Met Glu Leu Ser Arg Leu Arg Ser Asp Asp Thr Val Val Tyr Tyr Cys
             85                  90                  95

Ala Arg Asn Trp Phe Asp Ser Trp Gly Gln Gly Thr Leu Val Thr Val
            100                 105                 110

Ser Ser

<210> SEQ ID NO 7
<211> LENGTH: 114
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
             35                  40                  45

Gly Arg Ile Asn Pro Asn Ser Gly Gly Thr Asn Tyr Ala Gln Lys Phe
 50                  55                  60

Gln Gly Arg Val Thr Ser Thr Arg Asp Thr Ser Ile Ser Thr Ala Tyr
 65                  70                  75                  80

Met Glu Leu Ser Arg Leu Arg Ser Asp Asp Thr Val Val Tyr Tyr Cys
             85                  90                  95

Ala Arg Asn Trp Phe Asp Ser Trp Gly Gln Gly Thr Leu Val Thr Val
            100                 105                 110

Ser Ser

<210> SEQ ID NO 8
<211> LENGTH: 107
<212> TYPE: PRT
<213> ORGANISM: Homo sapiens
```

```
<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr Phe Gly Gln Gly Thr Lys Leu Glu Ile Lys
            100                 105

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr Phe Gly Gln Gly Thr Lys Leu Glu Ile Lys
            100                 105

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
```

```
                    100                 105

<210> SEQ ID NO 11
<211> LENGTH: 107
<212> TYPE: PRT
<213> ORGANISM: Homo sapiens

<400> SEQUENCE: 11

Asp Ile Gln Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
                100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
                100                 105

<210> SEQ ID NO 13
<211> LENGTH: 121
<212> TYPE: PRT
<213> ORGANISM: Artificial
<220> FEATURE:
<223> OTHER INFORMATION: heavy chain variable domain VH1

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Trp Met His Trp Val Arg Gln Ala Pro Gly Gln Gly Leu Glu Trp Met
            35                  40                  45
```

```
Gly Trp Ile His Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
                100                 105                 110

Gln Gly Thr Leu Val Thr Val Ser Ser
        115                 120
```

<210> SEQ ID NO 14
<211> LENGTH: 107
<212> TYPE: PRT
<213> ORGANISM: Artificial
<220> FEATURE:
<223> OTHER INFORMATION: light chain variable domain VL1

<400> SEQUENCE: 14

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asn Ile Asn Val Leu
                20                  25                  30

Leu Asn Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Gln Ser Tyr Pro Tyr
                85                  90                  95

Thr Phe Gly Gln Gly Thr Lys Leu Glu Ile Lys
                100                 105
```

<210> SEQ ID NO 15
<211> LENGTH: 729
<212> TYPE: DNA
<213> ORGANISM: Artificial
<220> FEATURE:
<223> OTHER INFORMATION: scFv Geneart VH1-VL1

<400> SEQUENCE: 15

```
caggtgcagc tggtgcagtc tggcgccgaa gtgaagaaac caggcgccag cgtgaaggtg      60
tcctgcaagg ccagcggcta cacctttacc agcagctgga tgcactgggt gcgccaggct     120
ccaggacagg gcctggaatg gatgggctgg atccacccta atagcggcgg caccaactac     180
gcccagaaat tccagggcag agtgaccatg acccgggaca ccagcatcag caccgcctac     240
atggaactga gccggctgag aagcgacgac accgccgtgt actactgcgc cagaggcgac     300
tactacggct atgtgtcttg gtttgcctac tggggccagg gcaccctcgt gacagtgtct     360
agcggaggcg aggatctggc ggcggagga agtggcggag ggggatccga tatccagatg     420
acccagagcc ccagcagcct gtctgccagc gtgggcgaca gagtgacaat cacctgtcag     480
gccagccaga acatcaacgt gctgctgaac tggtatcagc agaagcccgg caaggccccc     540
aagctgctga tctacaaggc ctccaacctg cacaccggcg tgcccagcag atttctggc     600 agcggctccg gcaccgactt caccttcacc atcagctccc tgcagcccga ggatatcgcc     660
acctactact gccagcaggg ccagagctac ccctacacat cggccaggg gaccaagctg     720
``` gaaatcaag                                                              729

```
<210> SEQ ID NO 16
<211> LENGTH: 451
<212> TYPE: PRT
<213> ORGANISM: Artificial
<220> FEATURE:
<223> OTHER INFORMATION: heavy chain with VH1 variable domain

<400> SEQUENCE: 16
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Ser |
| | | | 20 | | | | | 25 | | | | | 30 | | |
| Trp | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | His | Pro | Asn | Ser | Gly | Gly | Thr | Asn | Tyr | Ala | Gln | Lys | Phe |
| | 50 | | | | | 55 | | | | | 60 | | | | |
| Gln | Gly | Arg | Val | Thr | Met | Thr | Arg | Asp | Thr | Ser | Ile | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Ala | Arg | Gly | Asp | Tyr | Tyr | Gly | Tyr | Val | Ser | Trp | Phe | Ala | Tyr | Trp | Gly |
| | | | 100 | | | | | 105 | | | | | 110 | | |
| Gln | Gly | Thr | Leu | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | 195 | | | | | 200 | | | | | 205 | | | |
| Lys | Pro | Ser | Asn | Thr | Lys | Val | Asp | Lys | Val | Glu | Pro | Lys | Ser | Cys |
| | 210 | | | | | 215 | | | | | 220 | | | | |
| Asp | Lys | Thr | His | Thr | Cys | Pro | Pro | Cys | Pro | Ala | Pro | Glu | Leu | Leu | Gly |
| 225 | | | | | 230 | | | | | 235 | | | | | 240 |
| Gly | Pro | Ser | Val | Phe | Leu | Phe | Pro | Pro | Lys | Pro | Lys | Asp | Thr | Leu | Met |
| | | | | 245 | | | | | 250 | | | | | 255 | |
| Ile | Ser | Arg | Thr | Pro | Glu | Val | Thr | Cys | Val | Val | Val | Asp | Val | Ser | His |
| | | | 260 | | | | | 265 | | | | | 270 | | |
| Glu | Asp | Pro | Glu | Val | Lys | Phe | Asn | Trp | Tyr | Val | Asp | Gly | Val | Glu | Val |
| | | 275 | | | | | 280 | | | | | 285 | | | |
| His | Asn | Ala | Lys | Thr | Lys | Pro | Arg | Glu | Glu | Gln | Tyr | Asn | Ser | Thr | Tyr |
| | 290 | | | | | 295 | | | | | 300 | | | | |
| Arg | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | | 325 | | | | | 330 | | | | | 335 | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |

```
Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 17
<211> LENGTH: 214
<212> TYPE: PRT
<213> ORGANISM: Artificial
<220> FEATURE:
<223> OTHER INFORMATION: light chain with VL1 variable domain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Asn Val Leu
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 729
<212> TYPE: DNA
<213> ORGANISM: Artificial
<220> FEATURE:
```

<223> OTHER INFORMATION: scFv Geneart VH2-VL2

<400> SEQUENCE: 18

```
caggtgcagc tggtgcagtc tggcgccgaa gtgaagaaac aggcgccag cgtgaaggtg        60
tcctgcaagg ccagcggcta cacctttacc agcagctgga tgcactgggc agacaggct       120
ccaggccagg gactggaatg gatcggcgag atccacccca atagcggcgg caccaactac      180
gcccagaagt tccagggcag agccaccctg accgtggaca cctctagcag caccgcctac      240
atggaactga gccggctgag aagcgacgac accgccgtgt actactgcgc cagaggcgac      300
tactacggct atgtgtcttg gtttgcctac tggggccagg gcaccctcgt gacagtgtct      360
agcggaggcg gaggatctgg cggcggagga agtggcggag ggggatctga catccagatg      420
aaccagagcc ccagcagcct gagcgcctcc gtgggagaca gagtgaccat cacctgtcag      480
gccagccaga acatcaacgt gctgctgagc tggtatcagc agaagcccgg caaggccccc      540
aagctgctga tctacaaggc ctccaacctg cacaccggcg tgcccagcag atttctggc       600
agcggctccg gcaccgactt caccttcacc atcagctccc tgcagcccga ggatatcgcc      660
acctactact gccagcaggg ccagagctac ccctacacat cggccaggg gaccaagctg       720
gaaatcaag                                                             729
```

<210> SEQ ID NO 19
<211> LENGTH: 451
<212> TYPE: PRT
<213> ORGANISM: Artificial
<220> FEATURE:
<223> OTHER INFORMATION: chimeric 5G6 heavy chain

<400> SEQUENCE: 19

```
Gln Val Gln Leu Gln Gln Pro Gly Ser Val Leu Val Arg Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Lys Gln Arg Pro Gly Gln Gly Leu Glu Trp Ile
        35                  40                  45

Gly Glu Ile His Pro Asn Ser Gly Gly Thr Asn Tyr Asn Glu Lys Phe
    50                  55                  60

Lys Gly Lys Ala Thr Leu Thr Val Asp Thr Ser Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 20
<211> LENGTH: 214
<212> TYPE: PRT
<213> ORGANISM: Artificial
<220> FEATURE:
<223> OTHER INFORMATION: chimeric 5G6 light chain

<400> SEQUENCE: 20

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Leu
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 451
<212> TYPE: PRT
<213> ORGANISM: Artificial
<220> FEATURE:
<223> OTHER INFORMATION: heavy chain with VH2 variable domain

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Ala Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 22
<211> LENGTH: 451
<212> TYPE: PRT
<213> ORGANISM: Artificial
<220> FEATURE:
<223> OTHER INFORMATION: heavy chain with VH3 variable domain

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
        180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
    450

<210> SEQ ID NO 23
<211> LENGTH: 451
<212> TYPE: PRT
<213> ORGANISM: Artificial
<220> FEATURE:
<223> OTHER INFORMATION: heavy chain with VH4 variable domain

<400> SEQUENCE: 23

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Ser
            20                  25                  30
Trp Met His Trp Ala Arg Gln Ala Pro Gly Gln Gly Leu Glu Trp Ile
            35                  40                  45
Gly Glu Ile His Pro Asn Ser Gly Gly Thr Asn Tyr Ala Gln Lys Phe
        50                  55                  60
```

```
Gln Gly Arg Val Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 24
<211> LENGTH: 451
<212> TYPE: PRT
```

<213> ORGANISM: Artificial
<220> FEATURE:
<223> OTHER INFORMATION: heavy chain with VH5 variable domain

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Met
        35                  40                  45

Gly Glu Ile His Pro Asn Ser Gly Thr Asn Tyr Ala Gln Lys Phe
    50                  55                  60

Gln Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
                385                 390                 395                 400
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 25
<211> LENGTH: 214
<212> TYPE: PRT
<213> ORGANISM: Artificial
<220> FEATURE:
<223> OTHER INFORMATION: light chain with VL2 variable domain

<400> SEQUENCE: 25

Asp Ile Gln Met Asn Gln Ser Pro Ser Ser Leu Ser Ala Ser Val Gly
1               5                   10                  15

Asp Arg Val Thr Ile Thr Cys Gln Ala Ser Gln Asn Ile Asn Val Leu
                20                  25                  30

Leu Ser Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 121
<212> TYPE: PRT
<213> ORGANISM: Artificial
<220> FEATURE:
<223> OTHER INFORMATION: heavy chain variable domain VH2

<400> SEQUENCE: 26

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Ala Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
            115                 120

<210> SEQ ID NO 27
<211> LENGTH: 121
<212> TYPE: PRT
<213> ORGANISM: Artificial
<220> FEATURE:
<223> OTHER INFORMATION: heavy chain variable domain VH3

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
            115                 120

<210> SEQ ID NO 28
<211> LENGTH: 121
<212> TYPE: PRT
<213> ORGANISM: Artificial
<220> FEATURE:
<223> OTHER INFORMATION: heavy chain variable domain VH4

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Val Thr Met Thr Val Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
            85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
            115                 120

<210> SEQ ID NO 29
<211> LENGTH: 121
<212> TYPE: PRT
<213> ORGANISM: Artificial
<220> FEATURE:
<223> OTHER INFORMATION: heavy chain variable domain VH5

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Met
        35                  40                  45

Gly Glu Ile His Pro Asn Ser Gly Thr Asn Tyr Ala Gln Lys Phe
    50                  55                  60

Gln Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
            115                 120

<210> SEQ ID NO 30
<211> LENGTH: 107
<212> TYPE: PRT
<213> ORGANISM: Artificial
<220> FEATURE:
<223> OTHER INFORMATION: light chain variable domain VL2

<400> SEQUENCE: 30

Asp Ile Gln Met Asn Gln Ser Pro Ser Ser Leu Ser Ala Ser Val Gly
1               5                   10                  15

Asp Arg Val Thr Ile Thr Cys Gln Ala Ser Gln Asn Ile Asn Val Leu
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
            85                  90                  95

Thr Phe Gly Gln Gly Thr Lys Leu Glu Ile Lys
            100                 105

<210> SEQ ID NO 31
<211> LENGTH: 363
<212> TYPE: DNA
```

<213> ORGANISM: Artificial
<220> FEATURE:
<223> OTHER INFORMATION: heavy chain variable domain VH1

<400> SEQUENCE: 31

```
caggtgcagc tggtgcagtc tggcgccgaa gtgaagaaac caggcgccag cgtgaaggtg      60
tcctgcaagg ccagcggcta cacctttacc agcagctgga tgcactgggt gcgccaggct     120
ccaggacagg gcctggaatg gatgggctgg atccacccta atagcggcgg caccaactac     180
gcccagaaat tccagggcag agtgaccatg acccgggaca ccagcatcag caccgcctac     240
atggaactga gccggctgag aagcgacgac accgccgtgt actactgcgc cagaggcgac     300
tactacggct atgtgtcttg gtttgcctac tggggccagg gcaccctcgt gacagtgtct     360
agc                                                                  363
```

<210> SEQ ID NO 32
<211> LENGTH: 363
<212> TYPE: DNA
<213> ORGANISM: Artificial
<220> FEATURE:
<223> OTHER INFORMATION: heavy chain variable domain VH2

<400> SEQUENCE: 32

```
caggtgcagc tggtgcagtc tggcgccgaa gtgaagaaac caggcgccag cgtgaaggtg      60
tcctgcaagg ccagcggcta cacctttacc agcagctgga tgcactgggc cagacaggct     120
ccaggccagg gactggaatg gatcggcgag atccacccca atagcggcgg caccaactac     180
gcccagaagt tccagggcag agccaccctg accgtggaca cctctagcag caccgcctac     240
atggaactga gccggctgag aagcgacgac accgccgtgt actactgcgc cagaggcgac     300
tactacggct atgtgtcttg gtttgcctac tggggccagg gcaccctcgt gacagtgtct     360
agc                                                                  363
```

<210> SEQ ID NO 33
<211> LENGTH: 363
<212> TYPE: DNA
<213> ORGANISM: Artificial
<220> FEATURE:
<223> OTHER INFORMATION: heavy chain variable domain VH3

<400> SEQUENCE: 33

```
caggtgcagc tggtgcagtc tggcgccgaa gtgaagaaac caggcgccag cgtgaaggtg      60
tcctgcaagg ccagcggcta cacctttacc agcagctgga tgcactgggc cagacaggct     120
ccaggccagg gactggaatg gatcggcgag atccacccca atagcggcgg caccaactac     180
gcccagaagt tccagggcag agccaccatg accgtggaca cctctatcag caccgcctac     240
atggaactga gccggctgag aagcgacgac accgccgtgt actactgcgc cagaggcgac     300
tactacggct atgtgtcttg gtttgcctac tggggccagg gcaccctcgt gacagtgtct     360
agc                                                                  363
```

<210> SEQ ID NO 34
<211> LENGTH: 363
<212> TYPE: DNA
<213> ORGANISM: Artificial
<220> FEATURE:
<223> OTHER INFORMATION: heavy chain variable domain VH4

<400> SEQUENCE: 34

```
caggtgcagc tggtgcagtc tggcgccgaa gtgaagaaac caggcgccag cgtgaaggtg      60
```

```
tcctgcaagg ccagcggcta ccctttacc agcagctgga tgcactgggc cagacaggct    120
ccaggccagg gactggaatg gatcggcgag atccacccca atagcggcgg caccaactac    180
gcccagaagt tccagggcag agtgaccatg accgtggaca cctctatcag caccgcctac    240
atggaactga gccggctgag aagcgacgac accgccgtgt actactgcgc cagaggcgac    300
tactacggct atgtgtcttg gtttgcctac tggggccagg gcaccctcgt gacagtgtct    360
agc                                                                  363

<210> SEQ ID NO 35
<211> LENGTH: 363
<212> TYPE: DNA
<213> ORGANISM: Artificial
<220> FEATURE:
<223> OTHER INFORMATION: heavy chain variable domain VH5

<400> SEQUENCE: 35
caggtgcagc tggtgcagtc tggcgccgaa gtgaagaaac caggcgccag cgtgaaggtg     60
tcctgcaagg ccagcggcta ccctttacc agcagctgga tgcactggc cagacaggct    120 ccaggccagg gactggaatg gatgggcgag atccacccca atagcggcgg caccaactac    180
gcccagaagt tccagggcag agtgaccatg accgtggaca cctctatcag caccgcctac    240
atggaactga gccggctgag aagcgacgac accgccgtgt actactgcgc cagaggcgac    300
tactacggct atgtgtcttg gtttgcctac tggggccagg gcaccctcgt gacagtgtct    360
agc                                                                  363

<210> SEQ ID NO 36
<211> LENGTH: 321
<212> TYPE: DNA
<213> ORGANISM: Artificial
<220> FEATURE:
<223> OTHER INFORMATION: light chain variable domain VL1

<400> SEQUENCE: 36
gatatccaga tgacccagag ccccagcagc ctgtctgcca gcgtgggcga cagagtgaca     60
atcacctgtc aggccagcca gaacatcaac gtgctgctga actggtatca gcagaagccc    120
ggcaaggccc ccaagctgct gatctacaag gcctccaacc tgcacaccgg cgtgcccagc    180
agattttctg gcagcggctc cggcaccgac ttcaccttca ccatcagctc cctgcagccc    240
gaggatatcg ccacctacta ctgccagcag ggccagagct accctacac attcggccag    300 gggaccaagc tggaaatcaa g                                              321

<210> SEQ ID NO 37
<211> LENGTH: 321
<212> TYPE: DNA
<213> ORGANISM: Artificial
<220> FEATURE:
<223> OTHER INFORMATION: light chain variable domain VL2

<400> SEQUENCE: 37
gacatccaga tgaaccagag ccccagcagc ctgagcgcct ccgtgggaga cagagtgacc     60
atcacctgtc aggccagcca gaacatcaac gtgctgctga gctggtatca gcagaagccc    120
ggcaaggccc ccaagctgct gatctacaag gcctccaacc tgcacaccgg cgtgcccagc    180
agattttctg gcagcggctc cggcaccgac ttcaccttca ccatcagctc cctgcagccc    240
gaggatatcg ccacctacta ctgccagcag ggccagagct accctacac attcggccag    300
```
gggaccaagc tggaaatcaa g                                              321

<210> SEQ ID NO 38
<211> LENGTH: 251
<212> TYPE: PRT
<213> ORGANISM: Homo sapiens

<400> SEQUENCE: 38

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
                20                  25                  30

Ala Arg Trp Ala Leu Thr Cys Cys Leu Val Leu Pro Phe Leu Ala
            35                  40                  45

Gly Leu Thr Thr Tyr Leu Leu Val Ser Gln Leu Arg Ala Gln Gly Glu
        50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 39
<211> LENGTH: 251
<212> TYPE: PRT
<213> ORGANISM: Mus musculus

<400> SEQUENCE: 39

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
                20                  25                  30

Ala Arg Trp Ala Leu Thr Cys Cys Leu Val Leu Pro Phe Leu Ala
            35                  40                  45

Gly Leu Thr Thr Tyr Leu Leu Val Ser Gln Leu Arg Ala Gln Gly Glu
        50                  55                  60

Ala Cys Val Gln Phe Gln Ala Leu Lys Gly Gln Glu Phe Ala Pro Ser

```
                65                  70                  75                  80
        His Gln Gln Val Tyr Ala Pro Leu Arg Ala Asp Gly Asp Lys Pro Arg
                            85                  90                  95
        Ala His Leu Thr Val Val Arg Gln Thr Pro Thr Gln His Phe Lys Asn
                            100                 105                 110
        Gln Phe Pro Ala Leu His Trp Glu His Glu Leu Gly Leu Ala Phe Thr
                            115                 120                 125
        Lys Asn Arg Met Asn Tyr Thr Asn Lys Phe Leu Leu Ile Pro Glu Ser
                    130                 135                 140
        Gly Asp Tyr Phe Ile Tyr Ser Gln Val Thr Phe Arg Gly Met Thr Ser
        145                 150                 155                 160
        Glu Cys Ser Glu Ile Arg Gln Ala Gly Arg Pro Asn Lys Pro Asp Ser
                            165                 170                 175
        Ile Thr Val Val Ile Thr Lys Val Thr Asp Ser Tyr Pro Glu Pro Thr
                            180                 185                 190
        Gln Leu Leu Met Gly Thr Lys Ser Val Cys Glu Val Gly Ser Asn Trp
                    195                 200                 205
        Phe Gln Pro Ile Tyr Leu Gly Ala Met Phe Ser Leu Gln Glu Gly Asp
                    210                 215                 220
        Lys Leu Met Val Asn Val Ser Asp Ile Ser Leu Val Asp Tyr Thr Lys
        225                 230                 235                 240
        Glu Asp Lys Thr Phe Phe Gly Ala Phe Leu Leu
                            245                 250

<210> SEQ ID NO 40
<211> LENGTH: 252
<212> TYPE: PRT
<213> ORGANISM: Rattus norvegicus

<400> SEQUENCE: 40

Met Ala Glu Glu Leu Gly Leu Gly Phe Gly Glu Ala Val Pro Val Glu
        1               5                   10                  15
        Met Leu Pro Glu Gly Cys Arg His Arg Arg Glu Ala Arg Thr Gly Leu
                        20                  25                  30
        Ala Ala Arg Ser Lys Ala Cys Leu Ala Leu Thr Cys Cys Leu Leu Ser
                    35                  40                  45
        Phe Pro Ile Leu Ala Gly Leu Ser Thr Leu Leu Met Thr Gly Gln Leu
                50                  55                  60
        Arg Ile Pro Gly Lys Asp Cys Met Phe Pro Thr Val Thr Glu Glu Arg
        65                  70                  75                  80
        Ser Ala Pro Ser Ala Gln Pro Val Tyr Thr Pro Ser Arg Asp Lys Pro
                            85                  90                  95
        Lys Ala His Leu Thr Ile Met Arg Gln Thr Pro Val Pro His Leu Lys
                            100                 105                 110
        Asn Glu Leu Ala Ala Leu His Trp Glu Asn Asn Leu Gly Met Ala Phe
                            115                 120                 125
        Thr Lys Asn Arg Met Asn Tyr Thr Asn Lys Phe Leu Val Ile Pro Glu
                    130                 135                 140
        Ser Gly Asp Tyr Phe Ile Tyr Ser Gln Ile Thr Phe Arg Gly Thr Thr
        145                 150                 155                 160
        Ser Glu Cys Gly Asp Ile Ser Arg Val Arg Arg Pro Lys Lys Pro Asp
                            165                 170                 175
        Ser Ile Thr Val Val Ile Thr Lys Val Ala Asp Ser Tyr Pro Glu Pro
                            180                 185                 190
```

```
Ala His Leu Leu Thr Gly Thr Lys Ser Val Cys Glu Ile Ser Ser Asn
            195                 200                 205

Trp Phe Gln Pro Ile Tyr Leu Gly Ala Met Phe Ser Leu Glu Glu Gly
    210                 215                 220

Asp Arg Leu Met Val Asn Val Ser Asp Ile Ser Leu Val Asp Tyr Thr
225                 230                 235                 240

Lys Glu Asp Lys Thr Phe Phe Gly Ala Phe Leu Ile
                245                 250

<210> SEQ ID NO 41
<211> LENGTH: 251
<212> TYPE: PRT
<213> ORGANISM: Macaca fascicularis

<400> SEQUENCE: 41

Met Ala Glu Asp Leu Gly Leu Ser Phe Gly Thr Ala Ser Val Glu
1               5                   10                  15

Met Leu Pro Glu His Gly Ser Cys Arg Pro Lys Ala Arg Ser Ser Ser
            20                  25                  30

Ala Cys Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Leu Gln Asp Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Leu Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Val Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 42
<211> LENGTH: 1353
<212> TYPE: DNA
<213> ORGANISM: Artificial
<220> FEATURE:
<223> OTHER INFORMATION: heavy chain with variable domain VH1

<400> SEQUENCE: 42
caggtgcagc tggtgcagtc tggcgccgaa gtgaagaaac caggcgccag cgtgaaggtg      60
```

```
tcctgcaagg ccagcggcta cacctttacc agcagctgga tgcactgggt gcgccaggct        120
ccaggacagg gcctggaatg gatgggctgg atccacccta atagcggcgg caccaactac        180
gcccagaaat tccagggcag agtgaccatg acccgggaca ccagcatcag caccgcctac        240
atggaactga ccggctgag aagcgacgac accgccgtgt actactgcgc cagaggcgac         300
tactacggct atgtgtcttg gtttgcctac tggggccagg gcaccctcgt gacagtgtct        360
agcgcgtcga ccaagggccc cagcgtgttc ccgctagccc ccagcagcaa gagcaccagc        420
ggcggcacag ccgccctggg ctgcctggtg aaggactact tccccgagcc cgtgaccgtg        480
tcctggaact ctggagccct gacctccggc gtgcacacct tccccgccgt gctccagagc        540
agcggcctgt acagcctgag cagcgtggtg acagtgccca gcagcagcct gggaacccag        600
acctacatct gcaacgtgaa ccacaagccc agcaacacca aggtggacaa gaaggtggag        660
cccaagagct gcgacaagac ccacacctgc ccccctgcc ctgcccctga gctgctgggc        720
ggaccctccg tgttcctgtt ccccccaag cccaaggaca ccctgatgat cagccggacc        780
cccgaggtga cctgcgtggt ggtggacgtg agccacgagg accctgaggt gaagttcaat        840
tggtacgtgg acggcgtgga ggtgcacaac gccaagacca gccccgggga ggaacagtac        900
aacagcacct accgggtggt gtccgtgctg accgtgctgc accaggactg gctgaacggc        960
aaggaataca agtgcaaggt ctccaacaag gccctgcctg cccccatcga aaagaccatc       1020
agcaaggcca agggccagcc cagggagccc caggtgtaca ccctgccccc ctcccgggac       1080
gagctgacca gaaccaggt gtccctgacc tgtctggtga agggcttcta ccccagcgac        1140
atcgccgtgg agtgggagag caacggccag cccgagaaca actacaagac caccccccct       1200
gtgctggaca cgacggcag cttcttcctg tacagcaagc tgaccgtgga caagagccgg        1260
tggcagcagg gcaacgtgtt cagctgctcc gtgatgcacg aggccctgca caaccactac       1320
acccagaaga gcctgagcct gtcccccggc aag                                    1353

<210> SEQ ID NO 43
<211> LENGTH: 1353
<212> TYPE: DNA
<213> ORGANISM: Artificial
<220> FEATURE:
<223> OTHER INFORMATION: heavy chain with variable domain VH2

<400> SEQUENCE: 43
caggtgcagc tggtgcagtc tggcgccgaa gtgaagaaac caggcgccag cgtgaaggtg         60
tcctgcaagg ccagcggcta cacctttacc agcagctgga tgcactgggc cagacaggct        120
ccaggccagg gactggaatg gatcggcgag atccacccca atagcggcgg caccaactac        180
gcccagaagt tccagggcag agccaccctg accgtggaca cctctagcag caccgcctac        240
atggaactga ccggctgag aagcgacgac accgccgtgt actactgcgc cagaggcgac         300
tactacggct atgtgtcttg gtttgcctac tggggccagg gcaccctcgt gacagtgtct        360
agcgcgtcga ccaagggccc cagcgtgttc ccgctagccc ccagcagcaa gagcaccagc        420
ggcggcacag ccgccctggg ctgcctggtg aaggactact tccccgagcc cgtgaccgtg        480
tcctggaact ctggagccct gacctccggc gtgcacacct tccccgccgt gctccagagc        540
agcggcctgt acagcctgag cagcgtggtg acagtgccca gcagcagcct gggaacccag        600
acctacatct gcaacgtgaa ccacaagccc agcaacacca aggtggacaa gaaggtggag        660
cccaagagct gcgacaagac ccacacctgc ccccctgcc ctgcccctga gctgctgggc        720
```

| | |
|---|---|
| ggaccctccg tgttcctgtt cccccccaag cccaaggaca ccctgatgat cagccggacc | 780 |
| cccgaggtga cctgcgtggt ggtggacgtg agccacgagg accctgaggt gaagttcaat | 840 |
| tggtacgtgg acggcgtgga ggtgcacaac gccaagacca gccccgggga ggaacagtac | 900 |
| aacagcacct accgggtggt gtccgtgctg accgtgctgc accaggactg gctgaacggc | 960 |
| aaggaataca agtgcaaggt ctccaacaag gccctgcctg cccccatcga aaagaccatc | 1020 |
| agcaaggcca agggccagcc cagggagccc caggtgtaca ccctgccccc ctcccgggac | 1080 |
| gagctgacca agaaccaggt gtccctgacc tgtctggtga agggcttcta ccccagcgac | 1140 |
| atcgccgtgg agtgggagag caacggccag cccgagaaca actacaagac cacccccct | 1200 |
| gtgctggaca gcgacggcag cttcttcctg tacagcaagc tgaccgtgga caagagccgg | 1260 |
| tggcagcagg gcaacgtgtt cagctgctcc gtgatgcacg aggccctgca caaccactac | 1320 |
| acccagaaga gcctgagcct gtcccccggc aag | 1353 |

<210> SEQ ID NO 44
<211> LENGTH: 1353
<212> TYPE: DNA
<213> ORGANISM: Artificial
<220> FEATURE:
<223> OTHER INFORMATION: heavy chain with variable domain VH3

<400> SEQUENCE: 44

| | |
|---|---|
| caggtgcagc tggtgcagtc tggcgccgaa gtgaagaaac caggcgccag cgtgaaggtg | 60 |
| tcctgcaagg ccagcggcta cacctttacc agcagctgga tgcactgggc cagacaggct | 120 |
| ccaggccagg gactggaatg gatcggcgag atccaccca atagcggcgg caccaactac | 180 |
| gcccagaagt tccagggcag agccaccatg accgtggaca cctctatcag caccgcctac | 240 |
| atggaactga gccggctgag aagcgacgac accgccgtgt actactgcgc cagaggcgac | 300 |
| tactacggct atgtgtcttg gtttgcctac tggggccagg gcaccctcgt gacagtgtct | 360 |
| agcgcgtcga ccaagggccc cagcgtgttc ccgctagccc ccagcagcaa gagcaccagc | 420 |
| ggcggcacag ccgccctggg ctgcctggtg aaggactact cccccgagcc cgtgaccgtg | 480 |
| tcctggaact ctggagccct gacctccggc gtgcacacct tccccgccgt gctccagagc | 540 |
| agcggcctgt acagcctgag cagcgtggtg acagtgccca gcagcagcct gggaacccag | 600 |
| acctacatct gcaacgtgaa ccacaagccc agcaacacca aggtggacaa gaaggtggag | 660 |
| cccaagagct gcgacaagac ccacacctgc cccccctgcc ctgcccctga gctgctgggc | 720 |
| ggaccctccg tgttcctgtt cccccccaag cccaaggaca ccctgatgat cagccggacc | 780 |
| cccgaggtga cctgcgtggt ggtggacgtg agccacgagg accctgaggt gaagttcaat | 840 |
| tggtacgtgg acggcgtgga ggtgcacaac gccaagacca gccccgggga ggaacagtac | 900 |
| aacagcacct accgggtggt gtccgtgctg accgtgctgc accaggactg gctgaacggc | 960 |
| aaggaataca agtgcaaggt ctccaacaag gccctgcctg cccccatcga aaagaccatc | 1020 |
| agcaaggcca agggccagcc cagggagccc caggtgtaca ccctgccccc ctcccgggac | 1080 |
| gagctgacca agaaccaggt gtccctgacc tgtctggtga agggcttcta ccccagcgac | 1140 |
| atcgccgtgg agtgggagag caacggccag cccgagaaca actacaagac cacccccct | 1200 |
| gtgctggaca gcgacggcag cttcttcctg tacagcaagc tgaccgtgga caagagccgg | 1260 |
| tggcagcagg gcaacgtgtt cagctgctcc gtgatgcacg aggccctgca caaccactac | 1320 |
| acccagaaga gcctgagcct gtcccccggc aag | 1353 |

```
<210> SEQ ID NO 45
<211> LENGTH: 1353
<212> TYPE: DNA
<213> ORGANISM: Artificial
<220> FEATURE:
<223> OTHER INFORMATION: heavy chain with variable domain VH4

<400> SEQUENCE: 45
caggtgcagc tggtgcagtc tggcgccgaa gtgaagaaac caggcgccag cgtgaaggtg        60
tcctgcaagg ccagcggcta cctttacc agcagctgga tgcactgggc agacaggct         120 ccaggccagg gactggaatg gatcggcgag atccacccca atagcggcgg caccaactac       180
gcccagaagt tccagggcag agtgaccatg accgtgaca cctctatcag caccgcctac        240
atggaactga gccggctgag aagcgacgac accgccgtgt actactgcgc cagaggcgac       300
tactacggct atgtgtcttg gtttgcctac tggggccagg gcaccctcgt gacagtgtct       360
agcgcgtcga ccaagggccc cagcgtgttc ccgctagccc ccagcagcaa gagcaccagc       420
ggcggcacag ccgccctggg ctgcctggtg aaggactact ccccgagcc cgtgaccgtg        480 tcctggaact ctggagccct gacctccggc gtgcacacct ccccgccgt gctccagagc       540 agcggcctgt acagcctgag cagcgtggtg acagtgccca gcagcagcct gggaacccag       600
acctacatct gcaacgtgaa ccacaagccc agcaacacca aggtggacaa gaaggtggag       660
cccaagagct gcgacaagac ccacacctgc ccccctgcc ctgcccctga gctgctgggc        720
ggaccctccg tgttcctgtt ccccccaag cccaaggaca cctgatgat cagccggacc        780 cccgaggtga cctgcgtggt ggtggacgtg agccacgagg accctgaggt gaagttcaat      840
tggtacgtgg acggcgtgga ggtgcacaac gccaagacca gccccggga ggaacagtac       900 aacagcaccc tccgggtggt gtccgtgctg accgtgctgc accaggactg gctgaacggc       960
aaggaataca agtgcaaggt ctccaacaag gccctgcctg ccccatcga aaagaccatc      1020 agcaaggcca agggccagcc cagggagccc caggtgtaca ccctgccccc ctcccgggac      1080
gagctgacca agaaccaggt gtccctgacc tgtctggtga agggcttcta ccccagcgac      1140
atcgccgtgg agtgggagag caacggccag cccgagaaca actacaagac cacccccct       1200 gtgctggaca gcgacggcag cttcttcctg tacagcaagc tgaccgtgga caagagccgg      1260
tggcagcagg gcaacgtgtt cagctgctcc gtgatgcacg aggccctgca caaccactac      1320
acccagaaga gcctgagcct gtcccccggc aag                                   1353

<210> SEQ ID NO 46
<211> LENGTH: 1353
<212> TYPE: DNA
<213> ORGANISM: Artificial
<220> FEATURE:
<223> OTHER INFORMATION: heavy chain with variable domain VH5

<400> SEQUENCE: 46
caggtgcagc tggtgcagtc tggcgccgaa gtgaagaaac caggcgccag cgtgaaggtg        60
tcctgcaagg ccagcggcta cctttacc agcagctgga tgcactgggc agacaggct         120 ccaggccagg gactggaatg gatgggcgag atccacccca atagcggcgg caccaactac       180
gcccagaagt tccagggcag agtgaccatg accgtgaca cctctatcag caccgcctac        240
atggaactga gccggctgag aagcgacgac accgccgtgt actactgcgc cagaggcgac       300
tactacggct atgtgtcttg gtttgcctac tggggccagg gcaccctcgt gacagtgtct       360
agcgcgtcga ccaagggccc cagcgtgttc ccgctagccc ccagcagcaa gagcaccagc       420
```

| | |
|---|---|
| ggcggcacag ccgccctggg ctgcctggtg aaggactact tccccgagcc cgtgaccgtg | 480 |
| tcctggaact ctggagccct gacctccggc gtgcacacct ccccgccgt gctccagagc | 540 |
| agcggcctgt acagcctgag cagcgtggtg acagtgccca gcagcagcct gggaacccag | 600 |
| acctacatct gcaacgtgaa ccacaagccc agcaacacca aggtggacaa gaaggtggag | 660 |
| cccaagagct gcgacaagac ccacacctgc cccccctgcc ctgcccctga gctgctgggc | 720 |
| ggaccctccg tgttcctgtt ccccccaag cccaaggaca ccctgatgat cagccggacc | 780 |
| cccgaggtga cctgcgtggt ggtggacgtg agccacgagg accctgaggt gaagttcaat | 840 |
| tggtacgtgg acggcgtgga ggtgcacaac gccaagacca gccccgggga ggaacagtac | 900 |
| aacagcacct accgggtggt gtccgtgctg accgtgctgc accaggactg gctgaacggc | 960 |
| aaggaataca gtgcaaggt ctccaacaag gccctgcctg ccccatcga aaagaccatc | 1020 |
| agcaaggcca agggccagcc cagggagccc caggtgtaca ccctgccccc ctcccgggac | 1080 |
| gagctgacca gaaccaggt gtccctgacc tgtctggtga agggcttcta ccccagcgac | 1140 |
| atcgccgtgg agtgggagag caacggccag cccgagaaca actacaagac cacccccct | 1200 |
| gtgctggaca gcgacggcag cttcttcctg tacagcaagc tgaccgtgga caagagccgg | 1260 |
| tggcagcagg gcaacgtgtt cagctgctcc gtgatgcacg aggccctgca caaccactac | 1320 |
| acccagaaga gcctgagcct gtccccggc aag | 1353 |

<210> SEQ ID NO 47
<211> LENGTH: 642
<212> TYPE: DNA
<213> ORGANISM: Artificial
<220> FEATURE:
<223> OTHER INFORMATION: light chain with variable domain VL1

<400> SEQUENCE: 47

| | |
|---|---|
| gatatccaga tgacccagag ccccagcagc ctgtctgcca gcgtgggcga cagagtgaca | 60 |
| atcacctgtc aggccagcca gaacatcaac gtgctgctga ctggtatca gcagaagccc | 120 |
| ggcaaggccc ccaagctgct gatctacaag gcctccaacc tgcacaccgg cgtgcccagc | 180 |
| agattttctg gcagcggctc cggcaccgac ttcaccttca ccatcagctc cctgcagccc | 240 |
| gaggatatcg ccacctacta ctgccagcag ggccagagct acccctacac attcggccag | 300 |
| gggaccaagc tggaaatcaa gcgtacggtg gccgctccca gcgtgttcat cttcccccc | 360 |
| agcgacgagc agctgaagag cggcaccgcc tccgtggtgt gcctgctgaa caacttctac | 420 |
| ccccgggagg ccaaggtgca gtggaaggtg gacaacgccc tccagagcgg caacagccag | 480 |
| gaaagcgtca ccgagcagga cagcaaggac tccacctaca gcctgagcag caccctgacc | 540 |
| ctgagcaagg ccgactacga gaagcacaag gtgtacgcct gcgaggtgac ccaccagggc | 600 |
| ctgtccagcc ccgtgaccaa gagcttcaac cggggcgagt gc | 642 |

<210> SEQ ID NO 48
<211> LENGTH: 642
<212> TYPE: DNA
<213> ORGANISM: Artificial
<220> FEATURE:
<223> OTHER INFORMATION: light chain with variable domain VL2

<400> SEQUENCE: 48

| | |
|---|---|
| gacatccaga tgaaccagag ccccagcagc ctgagcgcct ccgtgggaga cagagtgacc | 60 |
| atcacctgtc aggccagcca gaacatcaac gtgctgctga gctggtatca gcagaagccc | 120 |
| ggcaaggccc ccaagctgct gatctacaag gcctccaacc tgcacaccgg cgtgcccagc | 180 |

```
agattttctg gcagcggctc cggcaccgac ttcaccttca ccatcagctc cctgcagccc      240
gaggatatcg ccacctacta ctgccagcag ggccagagct accectacac attcggccag      300 gggaccaagc tggaaatcaa gcgtacggtg gccgctccca gcgtgttcat cttccccccc      360
agcgacgagc agctgaagag cggcaccgcc tccgtggtgt gcctgctgaa caacttctac      420
ccccgggagg ccaaggtgca gtggaaggtg gacaacgccc tccagagcgg caacagccag      480
gaaagcgtca ccgagcagga cagcaaggac tccacctaca gcctgagcag caccctgacc      540
ctgagcaagg ccgactacga aagcacaag gtgtacgcct gcgaggtgac ccaccagggc      600
ctgtccagcc ccgtgaccaa gagcttcaac cggggcgagt gc                         642

<210> SEQ ID NO 49
<211> LENGTH: 1356
<212> TYPE: DNA
<213> ORGANISM: Artificial
<220> FEATURE:
<223> OTHER INFORMATION: 5G6 heavy chain with variable domain

<400> SEQUENCE: 49
caggtccagc tccagcaacc tggttctgtg ctggtgaggc ctggagcttc agtgaaggtg       60
tcctgcaagg cttctggcta caccttcacc agttcctgga tgcactgggc gaagcagagg      120
cctggacaag gccttgagtg gattggagag attcatccta atagtggtgg tactaactac      180
aatgagaagt tcaagggcaa ggccacactg actgtagaca tcctccag cacagcctac        240 gtggatctca gcagcctgac atctgaggac tctgcggtct attactgtgc aagagggat       300 tactacggct acgtctcctg gtttgcttac tggggccaag gactctggt cactgtctcc       360 tcagcctcca ccaagggccc cagcgtgttc cccctggccc ccagcagcaa gtctaccagc      420
ggcggcacag cagccctggg atgcctggtg aaggactact cccccagcc cgtgaccgtg       480 agctggaaca gcggagccct gacctccggc gtgcacacct tcccgccgt gctgcagagc       540 agcggcctgt acagcctgag cagcgtgtg accgtgccca gcagcctg gggacccag         600 acctacatct gcaacgtgaa ccacaagccc agcaacacca aggtggacaa gaaggtggag      660
cccaagagct gcgacaagac ccacacctgc cctccctgtc ctgctcctga gctgctcggc      720
ggaccctccg tgttcctgtt cccccccaag cccaaggaca ccctgatgat cagcaggacc      780
cccgaggtga cctgcgtggt ggtggacgtg agccacgagg acccagaggt gaagttcaac      840
tggtacgtgg acggcgtgga ggtgcacaac gccaagacca gcccagaga ggaacagtac      900 aacagcacct caggggtggt gtccgtgctg accgtgctgc accaggactg gctgaacggc      960
aaagagtaca agtgcaaggt ctccaacaag gccctgccag ccccccatcga gaaaaccatc      1020 agcaaggcca agggccagcc acgggagccc caggtgtaca ccctgccccc ctcccgcgag      1080
gagatgacca gaaccaggt gtccctgaca tgtctggtga aaggcttcta ccccagcgac      1140
atcgccgtgg agtgggagag caacggccag cccgagaaca actacaagac cacccccca       1200 gtgctggaca gcgacggcag cttcttcctg tacagcaagc tgaccgtgga caagagcagg      1260
tggcagcagg gcaacgtgtt cagctgcagc gtgatgcacg aggccctgca caaccactac      1320
acccagaaga gcctgagcct gtcccccggc aagtga                                1356

<210> SEQ ID NO 50
<211> LENGTH: 645
<212> TYPE: DNA
<213> ORGANISM: Artificial
<220> FEATURE:
```

<223> OTHER INFORMATION: 5G6 light chain with variable domain

<400> SEQUENCE: 50

```
gacatccaga tgaaccagtc tccatccagt ctgtctgcat cccttggaga cacaattacc      60
atcacttgcc atgccagtca gaacattaat gttttgttaa ctggtaccaa gcagaaacca     120
ggaaatattc ctaaactctt gatctataag gcttccaact tgcacacagg cgtcccatca     180
aggtttagtg gcagtggatc tggaacaggt ttcacattta ccatcagcag cctgcagcct     240
gaagacatcg ccacttacta ctgtcaacag ggtcaaagtt atccgtacac gttcggaggg     300
gggaccaagc tggaaataaa acggaccgtg gccgctccca gcgtgttcat cttcccccc      360
agcgacgagc agctgaagag cggcaccgcc tccgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag caccctgacc     540
ctgagcaagg ccgactacga gaagcacaag gtgtacgcct gcgaggtgac ccaccaggga     600
ctgtccagcc ccgtgaccaa gagcttcaac aggggcgagt gctga                     645
```

<210> SEQ ID NO 51
<211> LENGTH: 10
<212> TYPE: PRT
<213> ORGANISM: Mus musculus

<400> SEQUENCE: 51

Gly Tyr Thr Phe Thr Ser Ser Trp Met His
1               5                   10

<210> SEQ ID NO 52
<211> LENGTH: 8
<212> TYPE: PRT
<213> ORGANISM: Mus musculus

<400> SEQUENCE: 52

Ile His Pro Asn Ser Gly Gly Thr
1               5

<210> SEQ ID NO 53
<211> LENGTH: 14
<212> TYPE: PRT
<213> ORGANISM: Mus musculus

<400> SEQUENCE: 53

Ala Arg Gly Asp Tyr Tyr Gly Tyr Val Ser Trp Phe Ala Tyr
1               5                   10

<210> SEQ ID NO 54
<211> LENGTH: 6
<212> TYPE: PRT
<213> ORGANISM: Mus musculus

<400> SEQUENCE: 54

Gln Asn Ile Asn Val Leu
1               5

<210> SEQ ID NO 55
<211> LENGTH: 3
<212> TYPE: PRT
<213> ORGANISM: Mus musculus

<400> SEQUENCE: 55

Lys Ala Ser

```
<210> SEQ ID NO 56
<211> LENGTH: 9
<212> TYPE: PRT
<213> ORGANISM: Mus musculus

<400> SEQUENCE: 56

Gln Gln Gly Gln Ser Tyr Pro Tyr Thr
1               5

<210> SEQ ID NO 57
<211> LENGTH: 11
<212> TYPE: PRT
<213> ORGANISM: Artificial
<220> FEATURE:
<223> OTHER INFORMATION: heavy chain extended CDR1 VH5

<400> SEQUENCE: 57

Gly Tyr Thr Phe Thr Ser Ser Trp Met His Trp
1               5                   10

<210> SEQ ID NO 58
<211> LENGTH: 20
<212> TYPE: PRT
<213> ORGANISM: Artificial
<220> FEATURE:
<223> OTHER INFORMATION: heavy chain extended CDR2 VH5

<400> SEQUENCE: 58

Trp Met Gly Glu Ile His Pro Asn Ser Gly Gly Thr Asn Tyr Ala Gln
1               5                   10                  15

Lys Phe Gln Gly
            20

<210> SEQ ID NO 59
<211> LENGTH: 14
<212> TYPE: PRT
<213> ORGANISM: Artificial
<220> FEATURE:
<223> OTHER INFORMATION: heavy chain extended CDR3 VH5

<400> SEQUENCE: 59

Ala Arg Gly Asp Tyr Tyr Gly Tyr Val Ser Trp Phe Ala Tyr
1               5                   10

<210> SEQ ID NO 60
<211> LENGTH: 13
<212> TYPE: PRT
<213> ORGANISM: Artificial
<220> FEATURE:
<223> OTHER INFORMATION: light chain extended CDR1 VL1

<400> SEQUENCE: 60

Gln Ala Ser Gln Asn Ile Asn Val Leu Leu Asn Trp Tyr
1               5                   10

<210> SEQ ID NO 61
<211> LENGTH: 11
<212> TYPE: PRT
<213> ORGANISM: Artificial
<220> FEATURE:
<223> OTHER INFORMATION: light chain extended CDR2 VL1

<400> SEQUENCE: 61

Leu Leu Ile Tyr Lys Ala Ser Asn Leu His Thr
```

```
<210> SEQ ID NO 62
<211> LENGTH: 9
<212> TYPE: PRT
<213> ORGANISM: Artificial
<220> FEATURE:
<223> OTHER INFORMATION: light chain extended CDR3 VL1

<400> SEQUENCE: 62

Gln Gln Gly Gln Ser Tyr Pro Tyr Thr
1               5

<210> SEQ ID NO 63
<211> LENGTH: 363
<212> TYPE: DNA
<213> ORGANISM: Artificial
<220> FEATURE:
<223> OTHER INFORMATION: heavy chain variable domain 5G6

<400> SEQUENCE: 63
caggtccagc tccagcaacc tggttctgtg ctggtgaggc tggagcttc agtgaaggtg       60 tcctgcaagg cttctggcta caccttcacc agttcctgga tgcactgggc gaagcagagg      120
cctggacaag gccttgagtg gattggagag attcatccta atagtggtgg tactaactac      180
aatgagaagt tcaagggcaa ggccacactg actgtagaca catcctccag cacagcctac      240
gtggatctca gcagcctgac atctgaggac tctgcggtct attactgtgc aagaggggat      300
tactacggct acgtctcctg gtttgcttac tggggccaag gactctggt cactgtctcc      360 tca                                                                    363

<210> SEQ ID NO 64
<211> LENGTH: 321
<212> TYPE: DNA
<213> ORGANISM: Artificial
<220> FEATURE:
<223> OTHER INFORMATION: light chain variable domain 5G6

<400> SEQUENCE: 64
gacatccaga tgaaccagtc tccatccagt ctgtctgcat cccttggaga cacaattacc       60
atcacttgcc atgccagtca gaacattaat gttttgttaa gctggtacca gcagaaacca      120
ggaaatattc ctaaactctt gatctataag gcttccaact gcacacagg cgtcccatca       180 aggtttagtg gcagtggatc tggaacaggt tcacattta ccatcagcag cctgcagcct      240
gaagacatcg ccacttacta ctgtcaacag ggtcaaagtt atccgtacac gttcggaggg      300
gggaccaagc tggaaataaa a                                                321

<210> SEQ ID NO 65
<211> LENGTH: 41
<212> TYPE: DNA
<213> ORGANISM: Artificial
<220> FEATURE:
<223> OTHER INFORMATION: Primer Mix VH - back 1

<400> SEQUENCE: 65
gtgatcgcca tggcgtcgac cgakgtrmag cttcaggagt c                           41

<210> SEQ ID NO 66
<211> LENGTH: 41
<212> TYPE: DNA
<213> ORGANISM: Artificial
<220> FEATURE:
```

<223> OTHER INFORMATION: Primer Mix VH - back 2

<400> SEQUENCE: 66
gtgatcgcca tggcgtcgac cgaggtbcag ctbcagcagt c          41

<210> SEQ ID NO 67
<211> LENGTH: 41
<212> TYPE: DNA
<213> ORGANISM: Artificial
<220> FEATURE:
<223> OTHER INFORMATION: Primer Mix VH - back 3

<400> SEQUENCE: 67
gtgatcgcca tggcgtcgac ccaggtgcag ctgaagsart c          41

<210> SEQ ID NO 68
<211> LENGTH: 41
<212> TYPE: DNA
<213> ORGANISM: Artificial
<220> FEATURE:
<223> OTHER INFORMATION: Primer Mix VH - back 4

<400> SEQUENCE: 68
gtgatcgcca tggcgtcgac cgaggtccar ctgcaacart c          41

<210> SEQ ID NO 69
<211> LENGTH: 41
<212> TYPE: DNA
<213> ORGANISM: Artificial
<220> FEATURE:
<223> OTHER INFORMATION: Primer Mix VH - back 5

<400> SEQUENCE: 69
gtgatcgcca tggcgtcgac ccaggtycag ctbcagcart c          41

<210> SEQ ID NO 70
<211> LENGTH: 41
<212> TYPE: DNA
<213> ORGANISM: Artificial
<220> FEATURE:
<223> OTHER INFORMATION: Primer Mix VH - back 6

<400> SEQUENCE: 70
gtgatcgcca tggcgtcgac ccaggtycar ctgcagcart c          41

<210> SEQ ID NO 71
<211> LENGTH: 41
<212> TYPE: DNA
<213> ORGANISM: Artificial
<220> FEATURE:
<223> OTHER INFORMATION: Primer Mix VH - back 7

<400> SEQUENCE: 71
gtgatcgcca tggcgtcgac ccaggtccac gtgaagcart c          41

<210> SEQ ID NO 72
<211> LENGTH: 41
<212> TYPE: DNA
<213> ORGANISM: Artificial
<220> FEATURE:
<223> OTHER INFORMATION: Primer Mix VH - back 8

<400> SEQUENCE: 72
gtgatcgcca tggcgtcgac cgaggtgaas stggtggart c          41

<210> SEQ ID NO 73
<211> LENGTH: 41
<212> TYPE: DNA
<213> ORGANISM: Artificial
<220> FEATURE:
<223> OTHER INFORMATION: Primer Mix VH - back 9

<400> SEQUENCE: 73
gtgatcgcca tggcgtcgac cgavgtgawg stggtggagt c    41

<210> SEQ ID NO 74
<211> LENGTH: 41
<212> TYPE: DNA
<213> ORGANISM: Artificial
<220> FEATURE:
<223> OTHER INFORMATION: Primer Mix VH - back 10

<400> SEQUENCE: 74
gtgatcgcca tggcgtcgac cgaggtgcag stggtggart c    41

<210> SEQ ID NO 75
<211> LENGTH: 41
<212> TYPE: DNA
<213> ORGANISM: Artificial
<220> FEATURE:
<223> OTHER INFORMATION: Primer Mix VH - back 11

<400> SEQUENCE: 75
gtgatcgcca tggcgtcgac cgakgtgcam ctggtggart c    41

<210> SEQ ID NO 76
<211> LENGTH: 41
<212> TYPE: DNA
<213> ORGANISM: Artificial
<220> FEATURE:
<223> OTHER INFORMATION: Primer Mix VH - back 12

<400> SEQUENCE: 76
gtgatcgcca tggcgtcgac cgaggtgaag ctgatggart c    41

<210> SEQ ID NO 77
<211> LENGTH: 41
<212> TYPE: DNA
<213> ORGANISM: Artificial
<220> FEATURE:
<223> OTHER INFORMATION: Primer Mix VH - back 13

<400> SEQUENCE: 77
gtgatcgcca tggcgtcgac cgaggtgcar cttgttgart c    41

<210> SEQ ID NO 78
<211> LENGTH: 41
<212> TYPE: DNA
<213> ORGANISM: Artificial
<220> FEATURE:
<223> OTHER INFORMATION: Primer Mix VH - back 14

<400> SEQUENCE: 78
gtgatcgcca tggcgtcgac cgargtraag cttctcgart c    41

<210> SEQ ID NO 79
<211> LENGTH: 41
<212> TYPE: DNA
<213> ORGANISM: Artificial
<220> FEATURE:
<223> OTHER INFORMATION: Primer Mix VH - back 15

<400> SEQUENCE: 79
gtgatcgcca tggcgtcgac cgaagtgaar sttgaggart c            41

<210> SEQ ID NO 80
<211> LENGTH: 41
<212> TYPE: DNA
<213> ORGANISM: Artificial
<220> FEATURE:
<223> OTHER INFORMATION: Primer Mix VH - back 16

<400> SEQUENCE: 80
gtgatcgcca tggcgtcgac ccaggttact ctraaasart c            41

<210> SEQ ID NO 81
<211> LENGTH: 41
<212> TYPE: DNA
<213> ORGANISM: Artificial
<220> FEATURE:
<223> OTHER INFORMATION: Primer Mix VH - back 17

<400> SEQUENCE: 81
gtgatcgcca tggcgtcgac ccaggtccaa ctvcagcarc c            41

<210> SEQ ID NO 82
<211> LENGTH: 41
<212> TYPE: DNA
<213> ORGANISM: Artificial
<220> FEATURE:
<223> OTHER INFORMATION: Primer Mix VH - back 18

<400> SEQUENCE: 82
gtgatcgcca tggcgtcgac cgatgtgaac ttggaasart c            41

<210> SEQ ID NO 83
<211> LENGTH: 41
<212> TYPE: DNA
<213> ORGANISM: Artificial
<220> FEATURE:
<223> OTHER INFORMATION: Primer Mix VH - back 19

<400> SEQUENCE: 83
gtgatcgcca tggcgtcgac cgaggtgaag gtcatcgart c            41

<210> SEQ ID NO 84
<211> LENGTH: 38
<212> TYPE: DNA
<213> ORGANISM: Artificial
<220> FEATURE:
<223> OTHER INFORMATION: Primer Mix VH - forward 1

<400> SEQUENCE: 84
cctccaccac tcgagcccga ggaaacggtg accgtggt            38

<210> SEQ ID NO 85
<211> LENGTH: 38
<212> TYPE: DNA
<213> ORGANISM: Artificial
<220> FEATURE:
<223> OTHER INFORMATION: Primer Mix VH - forward 2

<400> SEQUENCE: 85
cctccaccac tcgagcccga ggagactgtg agagtggt            38

<210> SEQ ID NO 86
<211> LENGTH: 38

```
<212> TYPE: DNA
<213> ORGANISM: Artificial
<220> FEATURE:
<223> OTHER INFORMATION: Primer Mix VH - forward 3

<400> SEQUENCE: 86
cctccaccac tcgagcccgc agagacagtg accagagt                                   38

<210> SEQ ID NO 87
<211> LENGTH: 38
<212> TYPE: DNA
<213> ORGANISM: Artificial
<220> FEATURE:
<223> OTHER INFORMATION: Primer Mix VH - forward 4

<400> SEQUENCE: 87
cctccaccac tcgagcccga ggagacggtg actgaggt                                   38

<210> SEQ ID NO 88
<211> LENGTH: 35
<212> TYPE: DNA
<213> ORGANISM: Artificial
<220> FEATURE:
<223> OTHER INFORMATION: Primer Mix VL - back 1

<400> SEQUENCE: 88
ggcggtggcg ctagcgayat ccagctgact cagcc                                      35

<210> SEQ ID NO 89
<211> LENGTH: 35
<212> TYPE: DNA
<213> ORGANISM: Artificial
<220> FEATURE:
<223> OTHER INFORMATION: Primer Mix VL - back 2

<400> SEQUENCE: 89
ggcggtggcg ctagccaaat tgttctcacc cagtc                                      35

<210> SEQ ID NO 90
<211> LENGTH: 35
<212> TYPE: DNA
<213> ORGANISM: Artificial
<220> FEATURE:
<223> OTHER INFORMATION: Primer Mix VL - back 3

<400> SEQUENCE: 90
ggcggtggcg ctagcgayat tgtgmtmact cagtc                                      35

<210> SEQ ID NO 91
<211> LENGTH: 35
<212> TYPE: DNA
<213> ORGANISM: Artificial
<220> FEATURE:
<223> OTHER INFORMATION: Primer Mix VL - back 4

<400> SEQUENCE: 91
ggcggtggcg ctagcgayat tgtgytraca cagtc                                      35

<210> SEQ ID NO 92
<211> LENGTH: 35
<212> TYPE: DNA
<213> ORGANISM: Artificial
<220> FEATURE:
<223> OTHER INFORMATION: Primer Mix VL - back 5

<400> SEQUENCE: 92
```

```
ggcggtggcg ctagcgayat tgtratgacm cagtc                                       35

<210> SEQ ID NO 93
<211> LENGTH: 35
<212> TYPE: DNA
<213> ORGANISM: Artificial
<220> FEATURE:
<223> OTHER INFORMATION: Primer Mix VL - back 6

<400> SEQUENCE: 93
ggcggtggcg ctagcgayat tmagatramc cagtc                                       35

<210> SEQ ID NO 94
<211> LENGTH: 35
<212> TYPE: DNA
<213> ORGANISM: Artificial
<220> FEATURE:
<223> OTHER INFORMATION: Primer Mix VL - back 7

<400> SEQUENCE: 94
ggcggtggcg ctagcgayat tcagatgayd cagtc                                       35

<210> SEQ ID NO 95
<211> LENGTH: 35
<212> TYPE: DNA
<213> ORGANISM: Artificial
<220> FEATURE:
<223> OTHER INFORMATION: Primer Mix VL - back 8

<400> SEQUENCE: 95
ggcggtggcg ctagcgayat ycagatgaca cagac                                       35

<210> SEQ ID NO 96
<211> LENGTH: 35
<212> TYPE: DNA
<213> ORGANISM: Artificial
<220> FEATURE:
<223> OTHER INFORMATION: Primer Mix VL - back 9

<400> SEQUENCE: 96
ggcggtggcg ctagcgayat tgttctcawc cagtc                                       35

<210> SEQ ID NO 97
<211> LENGTH: 35
<212> TYPE: DNA
<213> ORGANISM: Artificial
<220> FEATURE:
<223> OTHER INFORMATION: Primer Mix VL - back 10

<400> SEQUENCE: 97
ggcggtggcg ctagcgayat tgwgctsacc caatc                                       35

<210> SEQ ID NO 98
<211> LENGTH: 35
<212> TYPE: DNA
<213> ORGANISM: Artificial
<220> FEATURE:
<223> OTHER INFORMATION: Primer Mix VL - back 11

<400> SEQUENCE: 98
ggcggtggcg ctagcgayat tstratgacc cartc                                       35

<210> SEQ ID NO 99
<211> LENGTH: 35
<212> TYPE: DNA
<213> ORGANISM: Artificial
```

```
<220> FEATURE:
<223> OTHER INFORMATION: Primer Mix VL - back 12

<400> SEQUENCE: 99
ggcggtggcg ctagcgayrt tktgatgacc carac                                35

<210> SEQ ID NO 100
<211> LENGTH: 35
<212> TYPE: DNA
<213> ORGANISM: Artificial
<220> FEATURE:
<223> OTHER INFORMATION: Primer Mix VL - back 13

<400> SEQUENCE: 100
ggcggtggcg ctagcgayat tgtgatgacb cagkc                                35

<210> SEQ ID NO 101
<211> LENGTH: 35
<212> TYPE: DNA
<213> ORGANISM: Artificial
<220> FEATURE:
<223> OTHER INFORMATION: Primer Mix VL - back 14

<400> SEQUENCE: 101
ggcggtggcg ctagcgayat tgtgataacy cagga                                35

<210> SEQ ID NO 102
<211> LENGTH: 35
<212> TYPE: DNA
<213> ORGANISM: Artificial
<220> FEATURE:
<223> OTHER INFORMATION: Primer Mix VL - back 15

<400> SEQUENCE: 102
ggcggtggcg ctagcgayat tgtgatgacc cagwt                                35

<210> SEQ ID NO 103
<211> LENGTH: 35
<212> TYPE: DNA
<213> ORGANISM: Artificial
<220> FEATURE:
<223> OTHER INFORMATION: Primer Mix VL - back 16

<400> SEQUENCE: 103
ggcggtggcg ctagcgayat tgtgatgaca caacc                                35

<210> SEQ ID NO 104
<211> LENGTH: 35
<212> TYPE: DNA
<213> ORGANISM: Artificial
<220> FEATURE:
<223> OTHER INFORMATION: Primer Mix VL - back 17

<400> SEQUENCE: 104
ggcggtggcg ctagcgayat tttgctgact cagtc                                35

<210> SEQ ID NO 105
<211> LENGTH: 35
<212> TYPE: DNA
<213> ORGANISM: Artificial
<220> FEATURE:
<223> OTHER INFORMATION: Primer Mix VL - back 18

<400> SEQUENCE: 105
ggcggtggcg ctagcgaaac aactgtgacc cagtc                                35
```

```
<210> SEQ ID NO 106
<211> LENGTH: 35
<212> TYPE: DNA
<213> ORGANISM: Artificial
<220> FEATURE:
<223> OTHER INFORMATION: Primer Mix VL - back 19

<400> SEQUENCE: 106
ggcggtggcg ctagcgaaaa tgtkctsacc cagtc                              35

<210> SEQ ID NO 107
<211> LENGTH: 38
<212> TYPE: DNA
<213> ORGANISM: Artificial
<220> FEATURE:
<223> OTHER INFORMATION: Primer Mix VL - back 20

<400> SEQUENCE: 107
ggcggtggcg ctagccaggc tgttgtgact caggaatc                           38

<210> SEQ ID NO 108
<211> LENGTH: 36
<212> TYPE: DNA
<213> ORGANISM: Artificial
<220> FEATURE:
<223> OTHER INFORMATION: Primer Mix VL - forward 1

<400> SEQUENCE: 108
atgctgacgc ggccgcacgt ttkatttcca gcttgg                             36

<210> SEQ ID NO 109
<211> LENGTH: 36
<212> TYPE: DNA
<213> ORGANISM: Artificial
<220> FEATURE:
<223> OTHER INFORMATION: Primer Mix VL - forward 2

<400> SEQUENCE: 109
atgctgacgc ggccgcacgt tttatttcca actttg                             36

<210> SEQ ID NO 110
<211> LENGTH: 36
<212> TYPE: DNA
<213> ORGANISM: Artificial
<220> FEATURE:
<223> OTHER INFORMATION: Primer Mix VL - forward 3

<400> SEQUENCE: 110
atgctgacgc ggccgcacgt ttcagctcca gcttgg                             36

<210> SEQ ID NO 111
<211> LENGTH: 36
<212> TYPE: DNA
<213> ORGANISM: Artificial
<220> FEATURE:
<223> OTHER INFORMATION: Primer Mix VL - forward 4

<400> SEQUENCE: 111
atgctgacgc ggccgcacct aggacagtca gtttgg                             36

<210> SEQ ID NO 112
<211> LENGTH: 17
<212> TYPE: DNA
<213> ORGANISM: Artificial
<220> FEATURE:
<223> OTHER INFORMATION: primer M13-Fwd
```

```
<400> SEQUENCE: 112
gtaaaacgac ggccagt                                                     17

<210> SEQ ID NO 113
<211> LENGTH: 16
<212> TYPE: DNA
<213> ORGANISM: Artificial
<220> FEATURE:
<223> OTHER INFORMATION: primer M13-Rev

<400> SEQUENCE: 113
aacagctatg accatg                                                      16

<210> SEQ ID NO 114
<211> LENGTH: 19
<212> TYPE: DNA
<213> ORGANISM: Artificial
<220> FEATURE:
<223> OTHER INFORMATION: primer T7

<400> SEQUENCE: 114
taatacgact cactatagg                                                   19

<210> SEQ ID NO 115
<211> LENGTH: 19
<212> TYPE: DNA
<213> ORGANISM: Artificial
<220> FEATURE:
<223> OTHER INFORMATION: primer SP6

<400> SEQUENCE: 115
gatttaggtg acactatag                                                   19

<210> SEQ ID NO 116
<211> LENGTH: 540
<212> TYPE: DNA
<213> ORGANISM: homo sapiens

<400> SEQUENCE: 116
ctaaaaggac aggagtttgc accttcacat cagcaagttt atgcacctct tagagcagac      60
ggagataagc caagggcaca cctgacagtt gtgagacaaa ctcccacaca gcactttaaa     120
aatcagttcc cagctctgca ctgggaacat gaactaggcc tggccttcac caagaaccga     180
atgaactata ccaacaaatt cctgctgatc ccagagtcgg gagactactt catttactcc     240
caggtcacat tccgtgggat gacctctgag tgcagtgaaa tcagacaagc aggccgacca     300
aacaagccag actccatcac tgtggtcatc accaaggtaa cagacagcta ccctgagcca     360
acccagctcc tcatggggac caagtctgta tgcgaagtag tagcaactg gttccagccc     420 atctacctcg gagccatgtt ctccttgcaa gaagggggaca agctaatggt gaacgtcagt     480
gacatctctt tggtggatta cacaaaagaa gataaaacct tctttggagc cttcttacta     540

<210> SEQ ID NO 117
<211> LENGTH: 1293
<212> TYPE: DNA
<213> ORGANISM: artificial
<220> FEATURE:
<223> OTHER INFORMATION: TL1A Fc fusion expression construct

<400> SEQUENCE: 117
atggagacag acacactcct gctatgggta ctgctgctct gggttccagg atccaccggc      60
```

```
ctaaaaggac aggagtttgc accttcacat cagcaagttt atgcacctct tagagcagac    120
ggagataagc caagggcaca cctgacagtt gtgagacaaa ctcccacaca gcactttaaa    180
aatcagttcc cagctctgca ctgggaacat gaactaggcc tggccttcac caagaaccga    240
atgaactata ccaacaaatt cctgctgatc ccagagtcgg gagactactt catttactcc    300
caggtcacat tccgtgggat gacctctgag tgcagtgaaa tcagacaagc aggccgacca    360
aacaagccag actccatcac tgtggtcatc accaaggtaa cagacagcta ccctgagcca    420
acccagctcc tcatggggac caagtctgta tgcgaagtag gtagcaactg gttccagccc    480
atctacctcg gagccatgtt ctccttgcaa aaggggaca agctaatggt gaacgtcagt    540
gacatctctt tggtggatta cacaaaagaa gataaaacct tctttggagc cttcttacta    600
caagcttctg gtggtaccca cacctgcccc cctgccctg ccctgagct gctgggcgga    660 cccagcgtgt tcctgttccc ccccaagccc aaggacaccc tgatgatcag ccggaccccc    720
gaggtgacct gcgtggtggt ggacgtgagc cacgaggacc ctgaggtcaa gttcaattgg    780
tacgtggacg gcgtggaggt gcacaacgcc aagaccaagc ccggaggga gcagtacaac    840 tccacctacc gggtggtgtc cgtgctgacc gtgctgcacc aggactggct gaacggcaag    900
gaatacaagt gcaaggtgtc caacaaggcc ctgcctgccc ccatcgaaaa gaccatcagc    960
aaggccaagg gccagcccag ggagccccag gtgtacaccc tgcccccag ccgggaggag   1020 atgaccaaga accaggtgtc cctgacctgc ctggtgaagg gcttctaccc cagcgacatc   1080
gccgtggagt gggagagcaa cggccagccc gagaacaact acaagaccac ccccctgtg   1140 ctggacagcg acggcagctt cttcctgtac agcaagctga ccgtggacaa gagcaggtgg   1200
cagcagggca acgtgttcag ctgcagcgtg atgcacgagg ccctgcacaa ccactacacc   1260
cagaagagcc tgagcctgtc ccccggcaag tga                               1293

<210> SEQ ID NO 118
<211> LENGTH: 618
<212> TYPE: DNA
<213> ORGANISM: artificial
<220> FEATURE:
<223> OTHER INFORMATION: secreted TL1A with N-terminal his-tag

<400> SEQUENCE: 118
atggagacag acacactcct gctatgggta ctgctgctct ggttccagg atccaccggc     60 catcaccatc atcaccatct aaaaggacag gagtttgcac cttcacatca gcaagtttat    120
gcacctctta gagcagacgg agataagcca agggcacacc tgacagttgt gagacaaact    180
cccacacagc actttaaaaa tcagttccca gctctgcact gggaacatga actaggcctg    240
gccttcacca gaaccgaat gaactatacc aacaaattcc tgctgatccc agagtcggga    300
gactacttca tttactccca ggtcacattc cgtgggatga cctctgagtg cagtgaaatc    360
agacaagcag gccgaccaaa caagccagac tccatcactg tggtcatcac caaggtaaca    420
gacagctacc ctgagccaac ccagctcctc atggggacca agtctgtatg cgaagtaggt    480
agcaactggt tccagcccat ctacctcgga gccatgttct ccttgcaaga aggggacaag    540
ctaatggtga acgtcagtga catctctttg gtggattaca caaaagaaga taaaaccttc    600
tttggagcct tcttacta                                                 618

<210> SEQ ID NO 119
<211> LENGTH: 38
```

-continued

<210> SEQ ID NO 119
<211> LENGTH: 38
<212> TYPE: DNA
<213> ORGANISM: Artificial
<220> FEATURE:
<223> OTHER INFORMATION: Primer GlnPr994

<400> SEQUENCE: 119
gttccaggat ccaccggcct aaaaggacag gagtttgc                                    38

<210> SEQ ID NO 120
<211> LENGTH: 33
<212> TYPE: DNA
<213> ORGANISM: Artificial
<220> FEATURE:
<223> OTHER INFORMATION: Primer GlnPr995

<400> SEQUENCE: 120
caccagaagc ttgtagtaag aaggctccaa aga                                         33

<210> SEQ ID NO 121
<211> LENGTH: 70
<212> TYPE: DNA
<213> ORGANISM: Artificial
<220> FEATURE:
<223> OTHER INFORMATION: Primer GlnPr1542

<400> SEQUENCE: 121
ctgctgctct gggttccagg atccaccggc caccatcatc atcaccatct aaaaggacag            60
gagtttgcac                                                                   70

<210> SEQ ID NO 122
<211> LENGTH: 36
<212> TYPE: DNA
<213> ORGANISM: Artificial
<220> FEATURE:
<223> OTHER INFORMATION: Primer GlnPr1543

<400> SEQUENCE: 122
gatcctcgag ctattatagt aagaaggctc caaaga                                      36

<210> SEQ ID NO 123
<211> LENGTH: 70
<212> TYPE: DNA
<213> ORGANISM: Artificial
<220> FEATURE:
<223> OTHER INFORMATION: Primer GlnPr1544

<400> SEQUENCE: 123
gatcgctagc caccatggag acagacacac tcctgctatg ggtactgctg ctctgggttc            60
caggatccac                                                                   70

<210> SEQ ID NO 124
<211> LENGTH: 448
<212> TYPE: PRT
<213> ORGANISM: Artificial Sequence
<220> FEATURE:
<223> OTHER INFORMATION: heavy chain with VH5 variable domain IgG4 hinge
      stabilized

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

-continued

```
Trp Met His Trp Ala Arg Gln Ala Pro Gly Gln Gly Leu Glu Trp Met
        35                  40                  45
Gly Glu Ile His Pro Asn Ser Gly Gly Thr Asn Tyr Ala Gln Lys Phe
 50                  55                  60
Gln Gly Arg Val Thr Met Thr Val Asp Thr Ser Ile Ser Thr Ala Tyr
 65                  70                  75                  80
Met Glu Leu Ser Arg Leu Arg Ser Asp Thr Ala Val Tyr Tyr Cys
                 85                  90                  95
Ala Arg Gly Asp Tyr Tyr Gly Tyr Val Ser Trp Phe Ala Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Cys Ser Arg Ser Thr Ser Glu Ser Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Lys Thr Tyr Thr Cys Asn Val Asp His
                195                 200                 205
Lys Pro Ser Asn Thr Lys Val Asp Lys Arg Val Glu Ser Lys Tyr Gly
        210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
                260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
                420                 425                 430
Leu His Asn His Tyr Thr Gln Lys Ser Leu Ser Leu Ser Leu Gly Lys
        435                 440                 445
```